United States Patent [19]
Zook et al.

[11] Patent Number: 6,153,757
[45] Date of Patent: Nov. 28, 2000

[54] METALLOPROTEINASE INHIBITORS AND INTERMEDIATES USEFUL FOR THEIR PREPARATION

[75] Inventors: Scott E. Zook, Del Mar; Raymond Dagnino, Jr., San Diego; Michael E. Deason, Poway; Steven L. Bender, Oceanside; Michael J. Melnick, San Diego, all of Calif.

[73] Assignee: Agouron Pharmaceuticals, Inc., La Jolla, Calif.

[21] Appl. No.: 09/011,971

[22] PCT Filed: Dec. 5, 1996

[86] PCT No.: PCT/US96/19328

§ 371 Date: Jun. 29, 1998

§ 102(e) Date: Jun. 29, 1998

[87] PCT Pub. No.: WO97/20824

PCT Pub. Date: Jun. 12, 1997

Related U.S. Application Data

[63] Continuation-in-part of application No. 08/759,713, Dec. 6, 1996, Pat. No. 5,753,653.
[60] Provisional application No. 60/041,496, Dec. 8, 1995.

[51] Int. Cl.$^7$ ................ C07D 213/68; C07D 213/70
[52] U.S. Cl. .............. 546/301; 546/302; 546/339; 548/342.5; 548/377.1; 549/78; 549/497; 562/833
[58] Field of Search .................. 546/301, 307, 546/339; 562/833; 548/342.5, 377.1; 549/78, 497

[56] References Cited

U.S. PATENT DOCUMENTS

| | | | |
|---|---|---|---|
| 4,032,639 | 6/1977 | Freed et al. | 424/251 |
| 5,183,900 | 2/1993 | Galardy et al. | 548/495 |
| 5,189,178 | 2/1993 | Galardy et al. | 548/495 |
| 5,256,657 | 10/1993 | Singh et al. | 514/228.2 |
| 5,455,258 | 10/1995 | MacPherson et al. | 514/357 |
| 5,506,242 | 4/1996 | MacPherson et al. | 514/336 |
| 5,552,419 | 9/1996 | MacPherson et al. | 514/357 |
| 5,569,665 | 10/1996 | Porter et al. | 514/357 |
| 5,753,653 | 5/1998 | Bender et al. | 514/227.5 |
| 5,929,097 | 7/1999 | Levin et al. | 514/351 |
| 5,932,595 | 8/1999 | Bender et al. | 514/317 |
| 5,985,900 | 11/1999 | Bender et al. | 514/336 |

FOREIGN PATENT DOCUMENTS

| | | |
|---|---|---|
| 276436 | 8/1988 | European Pat. Off. . |
| 438223 | 7/1991 | European Pat. Off. . |
| 0489577 | 6/1992 | European Pat. Off. . |
| 0489579 | 6/1992 | European Pat. Off. . |
| 606046 | 7/1994 | European Pat. Off. . |
| 757037 | 2/1997 | European Pat. Off. . |
| 757984 | 2/1997 | European Pat. Off. . |
| 0 780 386 | 6/1997 | European Pat. Off. . |
| 195 42 189 | 5/1997 | Germany . |

(List continued on next page.)

OTHER PUBLICATIONS

Robinson, et al., "Inhibitors of MMP–1: An Examination of P1' Cα Gem–Disubstitution in the Succinamide Hydroxamate Series," *Bioorganic & Medicinal Chemistry Letters*, vol. 6, No. 14 (1996), pp. 1719–1724.

Firestone, et al., "Total Synthesis of β–Lactam Antibiotics. IV. Epimerization of 6(7)–Aminopenicillins and–cephalosporins from α to β1," *Journal of Organic Chemistry*, vol. 39, No. 4 (1974), pp. 437–440.

Walker, "Vinylogous Amides of 2–Methylaminoethanol and Their Behavior with Lithium Aluminum Hydride. Vinylagous Urethanes of Ethanolamides and Their Acetylation," *Journal of Organic Chemistry*, vol. 27 (1962), pp. 4227–4231.

Cumberbatch, et al., "The Synthesis and Conformational Analysis of a Pair of Diastereoisomeric Cyclic Peptides with cis and trans Amide Bonds, Respectively," *Journal of the Chemical Society, Chemical Communications*, No. 7 (1993), pp. 641–642.

Capps, et al., "Novel Catalytic Rearrangements of 2–Vinyl–1,3–Thiazetidines," *Tetrahedron Letters*, vol. 25, No. 37 (1984), pp. 4157–4160.

Sakai, et al., "Convenient Synthesis of 1,4–Thiazane–3–Carboxylic Acid Derivatives," *Chemical and Pharmaceutical Bulletin*, vol. 29, No. 6 (1981), pp. 1554–1560.

(List continued on next page.)

*Primary Examiner*—Richard L. Raymond

[57] ABSTRACT

The invention relates to compounds of formula (1)

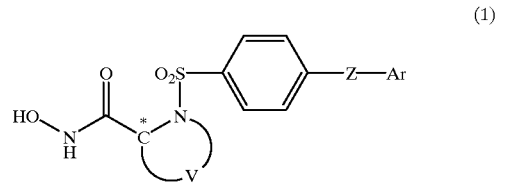

(1)

wherein: Z is O or S; V is a divalent radical which together with C* and N forms a ring having six ring atoms, where each of said ring atoms other than C* and N independently is unsubstituted or substituted by a suitable substituent, and at least one of said other ring atoms is a heteroatom selected from O, N and S, and the remainder is carbon atoms; and Ar is an aryl or heteroaryl group; and pharmaceutically acceptable prodrugs, salts and solvates thereof. The invention further relates to pharmaceutically acceptable prodrugs, salts and solvates of these compounds. The invention also relates to methods of inhibiting the activity of metalloproteinases by administering a compound of formula (1) or a prodrug, salt or solvate thereof. The invention further relates to pharmaceutical compositions comprising an effective amount of these compounds, prodrugs, salts, and solvates. The invention still further relates to methods and intermediates useful for preparing these compounds, prodrugs, salts, and solvates.

4 Claims, No Drawings

FOREIGN PATENT DOCUMENTS

| | | |
|---|---|---|
| WO 92/06966 | 4/1992 | WIPO . |
| WO 92/09563 | 6/1992 | WIPO . |
| WO 92/21360 | 12/1992 | WIPO . |
| WO 93/24449 | 12/1993 | WIPO . |
| WO 93/24475 | 12/1993 | WIPO . |
| WO 94/02466 | 2/1994 | WIPO . |
| WO 94/12169 | 6/1994 | WIPO . |
| WO 94/24140 | 10/1994 | WIPO . |
| WO 94/25435 | 11/1994 | WIPO . |
| WO 95/04735 | 2/1995 | WIPO . |
| WO 95/12603 | 5/1995 | WIPO . |
| WO 95/19961 | 7/1995 | WIPO . |
| WO 95/22966 | 8/1995 | WIPO . |
| WO 95/32944 | 12/1995 | WIPO . |
| WO 95/35275 | 12/1995 | WIPO . |
| WO 95/35276 | 12/1995 | WIPO . |
| WO 96/00214 | 1/1996 | WIPO . |
| WO 96/06074 | 2/1996 | WIPO . |
| WO 96/16027 | 5/1996 | WIPO . |
| WO 96/16931 | 6/1996 | WIPO . |
| WO 96/23791 | 8/1996 | WIPO . |
| WO 96/27583 | 9/1996 | WIPO . |
| WO 96/33172 | 10/1996 | WIPO . |
| WO 97/18194 | 5/1997 | WIPO . |
| WO 97/19068 | 5/1997 | WIPO . |
| WO 97/20824 | 6/1997 | WIPO . |
| WO 97/22587 | 6/1997 | WIPO . |
| WO 97/23459 | 7/1997 | WIPO . |
| WO 97/25969 | 7/1997 | WIPO . |
| WO 97/27174 | 7/1997 | WIPO . |
| WO 98/07697 | 2/1998 | WIPO . |
| WO 98/08815 | 3/1998 | WIPO . |
| WO 98/08825 | 3/1998 | WIPO . |

OTHER PUBLICATIONS

Woessner, Jr., "Matrix metalloproteinases and their inhibitors in connective tissue remodeling", The FASEB Journal, vol. 5, No. 8 (1991), pp. 2145–2154.

Freije et al., "Molecular Cloning and Expression of Collagenase–3, a Novel Human Matrix Metalloproteinase Produced by Breast Carcinomas", The Journal of Biological Chemistry, vol. 269, No. 24 (1994), pp. 16766–16773.

Mitchell et al., "Cloning, Expression, and Type II Collagenolytic Activity of Matrix Metalloproteinase–13 from Human Osteoarthritic Cartilage", The Journal of Clinical Investigation, vol. 97, No. 3 (1996), pp. 761–768.

Ray et al., "Matrix metalloproteinases and malignant disease: recent developments", Expert Opinion on Investigational Drugs, vol. 5, No. 3 (1996), pp. 323–335.

Birkedal–Hansen, "Host–Mediated Extracellular Matrix Destruction by Metalloproteinases", Molecular Pathogenesis of Periodontal Disease (1994), pp. 191–202.

Gijbels et al., "Gelatinase in the cerebrospinal fluid of patients with multiple sclerosis and other inflammatory neurological disorders", Journal of Neuroimmunology, 41 (1992), pp. 29–34.

O'Day et al., "Differences in Response in Vivo to Amphotericin B Among Candida albicans Strains", Investigative Ophthalmology & Visual Science, vol. 32, No. 5 (1991), pp. 1569–1572.

Rosenberg et al., "Tumor necrosis factor–α–induced gelatinase B causes delayed opening of the blood–brain barrier: an expanded therapeutic window", Brain Research, vol. 703, Nos. 1–2 (1995), pp. 151–155.

Rosenberg et al., "Proteolytic Cascade Enzymes Increase in Focal Cerebral Ischemia in Rat", Journal of Cerebral Blood Flow and Metabolism, vol. 16, No. 3 (1996), pp. 360–366.

Fisher et al., "Molecular basis of sun–induced premature skin ageing and retinoid antagonism", Nature, vol. 379, No. 6563 (1996), pp. 335–339.

Saarialho–Kere et al., "Distinct Populations of Basal Keratinocytes Express Stromelysin–1 and Stromelysin–2 in Chronic Wounds", The Journal of Clinical Investigation, vol. 94 (1994), p. 79–88.

Newby et al., "Extracellular matrix degrading metalloproteinases in the pathogenesis of arteriosclerosis", Arteriosclerosis, Supplement to Basic Research in Cardiology, vol. 89, Supl. 1 (1994), pp. 59–70.

McMillan et al., "Characterization of a Glomerular Epithelial Cell Metalloproteinase as Matrix Metalloproteinase–9 with Enhanced Expression in a Model of Membranous Nephropathy", The Journal of Clinical Investigation, vol. 97, No. 4 (1996), pp. 1094–1101.

Belaaouaj et al., "Human Macrophage Metalloelastase", The Journal of Biological Chemistry, vol. 270, No. 24 (1995), pp. 14568–14575.

Martin, "Synthesis of Aldehydes, Ketones, and Carboxylic Acids from Lower Carbonyl Compounds by C—C Coupling Reactions", Synthesis, No. 9 (1979), pp. 633–655.

Yabroff et al., "The Relative Strengths of Some Hydrocarbon Derivatives of Boric Acid", The Journal of the American Chemical Society, vol. 56 (1934), pp. 1850–1857.

Malon et al., "Chiroptical Properties and Conformation of N–Acetyl–L–Amino Acids N'–Methylamides with Aliphatic Side Chains", Collection Czechoslovak Chem. Commun., vol. 48 (1983), pp. 2844–2861.

Pridgen et al., "Regiospecific Synthesis of Arylfurans Employing a Nickel(II)–Phosphine Complex as a Catalyst in the Homolytic Cross–Coupling of Grignard Reagents to Halofurans", J. Org. Chem., vol. 47, No. 8 (1982), pp. 1590–1592.

Yang et al., "Regiospecific Synthesis of 3,4–Disubstituted Furans and 3–Substituted Furans Using 3,4–Bis(tri–n–butylstannyl)furan and 3–(Tri–n–butylstannyl)furan as Building Blocks", Tetrahedron, vol. 50, No. 32 (1994), pp. 9583–9608.

Ribereau et al., "Synthesis and physical properties of the six furylpyridines", Canadian Journal of Chemistry, vol. 61, No. 2 (1983), pp. 334–342.

Ishikura et al., "A Novel Synthesis of 4–Aryl– and 4–Heteroarylpyridines via Diethyl(4–pyridyl)borane", Chem. Pharm. Bull., vol. 33, No. 11 (1985), pp. 4755–4763.

Delacotte et al., "Synthesis of Tritiated Threonine with a High Specific Activity", Journal of Labelled Compounds and Radiopharmaceuticals, vol. 29, No. 10 (1991), pp. 1141–1146.

Friedrich–Bochnitschek et al., "Allyl Esters as Carboxy Protecting Groups in the Synthesis of O–Glycopeptides", J. Org. Chem. (1989), pp. 751–756.

Belshaw et al., "Chlorotrimethylsilane Mediates Formation of ω–Allyl Esters of Aspartic and Glutamic Acids", Synthetic Communications, vol. 20, No. 20 (1990), pp. 3157–3160.

McNamara et al., "Synthesis of 4–Cyano–4'–halobiphenyls", J. Org. Chem., vol. 41, No. 6 (1976), p. 1071.

Amatore et al., "Efficient palladium–catalyzed synthesis of unsymmetrical donor–acceptor biaryls and polyaryls", *Journal of Organometallic Chemistry*, vol. 390, No. 3 (1990), pp. 389–398.

Boy et al., "Electrosynthesis of Unsymmetrical Donor–Acceptor Polyaryls", *Tetrahedon Letters*, vol. 33, No. 4 (1992), pp. 491–494.

Pospíšek et al., "Tert–Leucine and Its Simple Peptides", *Collection Czechoslov. Chem. Commun.*, vol. 42 (1977), pp. 1069–1076.

Carpino et al., "Tetramethylfluoroformamidinium Hexafluorophosphate: A Rapid–Acting Peptide Coupling Reagent for Solution and Solid Phase Peptide Synthesis", *J. Am. Chem. Soc.*, vol. 117, No. 19 (1995), pp. 5401–5402.

Freskos, "Use of R–Pantolactone in the Synthesis of L–Tert Leucine Derivatives", *Synthetic Communications*, vol. 24, No. 4 (1994), pp. 557–563.

Abdel–Meguid et al., "An Orally Bioavailable HIV–1 Protease Inhibitor Containing an Imidazole–Derived Peptide Bond Replacement: Crystallographic and Pharmacokinetic Analysis", *Biochemistry*, vol. 33, No. 39 (1994), pp. 11671–11677.

Mathias, "Esterification and Alkylation Reactions Employing Isoureas", *International Journal of Methods in Synthetic Organic Chemistry*, No. 8 (1979), pp. 561–576.

Boger et al., "Total Synthesis of Azafluoranthene Alkaloids: Rufescine and Imeluteine", *J. Org. Chem.* (1984), vol. 49, No. 21, pp. 4050–4055.

Ellis et al., "Antifungal activity of some imidazole derivatives", *J. Pharm. Pharmacol.* (1964), vol. 16, pp. 400–407.

Von E. Felder et al., Helv. Chim. Acta, vol. 43, No. 117 (1960), p. 888–894.

Aebischer et al., "Synthesis and NMDA Antagonistic Properties of the Enantiomers of 4–(3–Phosphonopropyl)piperazine–2–carboxylic Acid (CPP) and of the Unsaturated Analogue (E)–4(3–Phosphonoprop–2–enyl)piperazine–2–carboxylic Acid (CPP–end)," Helvetica Chimica Acta, vol. 72 (1989), p. 1043–1051.

Brunwin et al., "Total Synthesis of Nuclear Analogues of 7–Methylcephalosporin," J.C.S. Perkin I (1973), p. 1321–1328.

Knight et al., "A novel coumarin–labelled peptide for sensitive continuous assays of the matrix metalloproteinases," FEBS, vol. 296, No. 3 (1992), p. 263–266.

Menegatti et al., "Inhibition of Serine Proteinases by Tetra–p–Amidinophenoxy–neo–Pentane: Thermodynamic and Molecular Modeling Study," J. Enzyme Inhibition, vol. 2 (1987), p. 23–30.

Johnson, "Collagenase Inhibitors," DN&P, vol. 3, No. 8 (1990), p. 453–458.

Henderson et al., "Design of Inhibitors of Articular Cartilage Destruction," Drugs of the Future, vol. 15, No. 5 (1990), p. 495–508.

Harrison et al., "A Semicontinuous, High–Performance Liquid Chromatography–Based Assay for Stromelysin," Analytical Biochemistry, vol. 180 (1989), p. 110–113.

Shinmei et al., "The Mechanism of Cartilage Degradation in Osteoarthritic Joints," Seminars in Arthritis and Rheumatism, vol. 19, No. 4, Suppl. 1 (1990), p. 16–20.

Weingarten et al., "Spectrophotometric Assay for Vertebrate Collegenase," Analytical Biochemistry, vol. 147 (1985), p. 437–440.

Davies et al., "A Synthetic Matrix Metalloproteinase Inhibitor Decreases Tumor Burden and Prolongs Survival of Mice Bearing Human Ovarian Carcinoma Xenografts," Cancer Research, vol. 53 (1993), p. 2087–2091.

Brinckerhoff, "Joint Destruction in Arthritis: Metalloproteinases in the Spotlight," Arthritis & Rheumatism, vol. 34, No. 9 (1991), p. 1073–1075.

Morrison, "Kinetics of the Reversible Inhibition of Enzyme– Catalysed Reactions by Tight–Binding Inhibitors," Biochem. Biophys. Acta, vol. 185 (1969), p. 269–286.

Lohmander et al., "Metalloproteinases, Tissue Inhibitor, and Proteoglycan Fragments in Knee Synovial Fluid in Human Osteoarthritis," Arthritis & Rheumatism, vol. 36, No. 2 (1993), p. 181–187.

Schwartz et al., "Synthetic Inhibitors of Bacterial and Mammalian Interstitial Collagenases," Progress in Medicinal Chemistry, vol. 29 (1992), p. 271–334.

Johnson et al., "Collagenase Inhibitors: Their Design and Potential Therapeutic Use", *J. Enzyme Inhibition*, vol. 2, (1987), p. 1–22.

Morphy et al., "Matrix Metalloproteinase Inhibitors: Current Status," *Current Medicinal Chemistry*, (1995), 2, pp. 743–762.

Porter et al., "Recent developments in matrix metalloproteinase inhibitors," *Exp. Opin. Ther. Patents* (1995) 5(12), pp. 1287–1296.

Beckett et al., "Recent advances in matrix metalloproteinase inhibitor research," *DDT*, vol. 1, No. 1 (Jan. 1996), pp. 16–26.

Greenstein, *Chemistry of the Amino Acids*, (1984), p. 886–889.

Smith et al., "A Superior Synthesis of Diaryl Ethers by the Use of Ultrasound in the Ullmann Reaction," *J. Chem. Soc. Perkin Trans. I*, (1992), p. 407–408.

Sammes et al., "A Novel, Simple Method for the Preparation of Hindered Diphenyl Ethers," *J. Chem. Soc. Perkin Trans. I*, (1988), p. 3229–3231.

Hassner et al., "Aminopyridines as Acylation Catalysts for Tertiary Alcohols," *Tetrahedron*, vol. 34 (1978), pp. 2069–2076.

Sprague et al., "Studies in the Cyanine Dye Series. IX. 4,4'–Pyridocyanines and 4–Pyrido–4'–cyanines," *Journal of the American Chemical Society*, Vo. 59, No. 12 (1937), p. 2697–2699.

Shao et al., "An Enantiomeric Synthesis of allo–Threonines and β–Hydroxyvalines," *J. Org. Chem.*, vol. 61, No. 8 (1996), pp. 2582–2583.

Thompson et al., "A General Synthesis of 5–Arylnicotinates," *J. Org. Chem.*, vol.49, No. 26 (1984), pp. 5237–5243.

Gehring et al., "Characterization of the Phe–81 and Val–82 Human Fibroblast Collagenase Catalytic Domain Purified from *Escherichia coli,*" The Journal of Biological Chemistry, vol. 270, No. 38 (1995), pp. 22507–22513.

Marcy et al., "Human Fibroblast Stromelysin Catalytic Domain: Expression, Purification, and Characterization of a C–Terminally Truncated Form," *Biochemistry*, vol. 30, No. 26 (1991), p. 6476–6483.

Bender et al., "Metalloprotease of Matrix Inhibitors (CASE RAN 4070/106)," *Industrial Property Gazette*, pp. 241, (1995).

Tamura et al., "Highly Selective and Orally Active Inhibitors of Type IV Collagenase (MMP–9 and MMP–2): N–Sulfonylamino Acid Derivatives", J. Med. Chem. (1998), 41(4), pp. 640–649.

METALLOPROTEINASE INHIBITORS AND INTERMEDIATES USEFUL FOR THEIR PREPARATION

This application is a national phase filing under 35 U.S.C. §371 of International Patent Application No. PCT/US96/19328, filed Dec. 5, 1996, and a continuation-in-part of U.S. patent application Ser. No. 08/759,713, filed Dec. 6, 1996, now U.S. Pat. No. 5,753,653, which bases priority on U.S. Provisional Application No. 60/041,496, filed on Dec. 8, 1995, abandoned.

The present invention relates to compounds that inhibit metalloproteinases, particularly matrix metalloproteinases and tumor necrosis factor-α convertase, and their pharmaceutically acceptable salts and pharmaceutically acceptable prodrugs. The invention further relates to the uses of these compounds, salts and prodrugs for the therapeutic treatment of humans or animals.

Matrix metalloproteinases ("MMPs") are a family of enzymes, including, but not limited to, collagenases, gelatinases, matrilysin, and stromelysins, which are involved in the degradation and remodelling of connective tissues. These enzymes are found in a number of cell types that are found in or associated with connective tissue, such as fibroblasts, monocytes, macrophages, endothelial cells and metastatic tumor cells. They also share a number of properties, including zinc and calcium dependence, secretion as zymogens, and 40–50% amino acid sequence homology.

Matrix metalloproteinases degrade the protein components of the extracellular matrix, i.e. the protein components found in the linings of joints, interstitial connective tissue, basement membranes, cartilage and the like. These proteins include collagen, proteoglycan, fibronectin and lamanin.

Collagen is the major structural protein of mammalian tissue, comprising one-third of the total protein in mammalian organisms, and is an essential component of many matrix tissues, including cartilage, bone, tendons and skin. Interstitial collagenases catalyze the initial (rate-limiting) cleavage of native collagen types I, II, III and X. These enzymes cleave collagen into two fragments which spontaneously denature at physiological temperature. Denaturation of collagen involves conversion of the rigidly coiled helix to a random coil referred to as gelatin. These gelatin (denatured collagen) fragments are then subject to further cleavage and degradation by less specific enzymes. The net result of collagenase cleavage is thus the loss of structural integrity in the matrix tissue (collagen collapse), an essentially irreversible process.

The gelatinases include two distinct yet highly related enzymes: a 72-kiloDalton (kDa) enzyme and a 92-kiloDalton enzyme. The former is released by fibroblasts while the latter is released by mononuclear phagocytes, neutrophils, corneal epithelial cells, tumor cells, cytotrophoblasts and keratinocytes. Both enzymes degrade gelatins (denatured collagens), collagen types IV (basement membrane) and V, fibronectins (high molecular weight multifunctional glycoproteins found in soft connective tissue and basement membranes) and insoluble elastin (highly cross-linked hydrophobic proteins found in load bearing fibers of mammalian connective tissue).

Stromelysins (1 and 2) cleave a broad range of matrix substrates, including lamanin, fibronectins, proteoglycans and collagen types IV and IX (non-helical).

Matrilysin (putative metalloproteinase or PUMP) also degrades a wide variety of matrix substrates, including proteoglycans, gelatins, fibronectins, elastins and lamanin. Matrilysin has been found in mononuclear phagocytes, rat uterine explants and tumor cells.

In normal tissues, the activity of matrix metalloproteinases is tightly regulated. As a result, the breakdown of connective tissue mediated by these enzymes is generally in a dynamic equilibrium with synthesis of new matrix tissue.

In a number of pathological disease conditions, however, deregulation of matrix metalloproteinase activity leads to the uncontrolled breakdown of extracellular matrix. These disease conditions include arthritis (e.g., rheumatoid arthritis and osteoarthritis), periodontal disease, aberrant angiogenesis, tumor metastasis and invasion, tissue ulceration (e.g., corneal ulceration, gastric ulceration or epidermal ulceration), bone disease, HIV-infection and complications from diabetes.

Administration of matrix metalloproteinase inhibitors has been found to reduce the rate of connective tissue degradation, thereby leading to a favorable therapeutic effect. For example, in *Cancer Res.*, vol. 53, p. 2087 (1993), a synthetic matrix metalloproteinase inhibitor was shown to have in vivo efficacy in a murine model for ovarian cancer with an apparent mode of action consistent with inhibition of matrix remodelling. The design and uses of MMP inhibitors are reviewed, for example, in *J. Enzyme Inhibition*, 2, 1–22 (1987); *Progress in Medicinal Chemistry* 29, 271–334 (1992); *Current Medicinal Chemistry*, 2, 743–762 (1995); *Exp. Opin. Ther. Patents*, 5, 1287–1296 (1995); and *Drug Discovery Today*, 1, 16–26 (1996).

Matrix metalloproteinase inhibitors are also the subject of numerous patents and patent applications, including: U.S. Pat. Nos. 5,189,178; 5,183,900; 5,506,242; 5,552,419; 5,455,258; European Patent Application No. 0 438 223; European Patent Application No. 0 276 436; WIPO International Publication No. WO 92/21360; WIPO International Publication No. WO 92/06966; WIPO International Publication No. WO 92/09563; WIPO International Publication No. WO 96/00214; WIPO International Publication No. 95/35276; and WIPO International Publication No. WO 96/27583, the disclosures of each of which are incorporated herein by reference.

Tumor necrosis factor- ("TNF-α") is a cytokine which is produced as a 28-kDa precursor and released in an active 17-kDa form. This active form can mediate a large number of deleterious effects in vivo, including inflammation, fever, cardiovascular effects, haemorrhage, coagulation and acute phase responses, similar to those seen during acute infections and shock states. Chronic administration of TNF-α can cause cachexia and anorexia; accumulation of excess of TNF-α can be fatal.

TNF-α convertase is a metalloproteinase involved in the biosynthesis of TNF-α. Inhibition of TNF-α convertase inhibits production of TNF-α.

Since excessive TNF-α production has been noted in several disease conditions characterized by MMP-mediated tissue degradation, including multiple sclerosis, arthritis and cancer, compounds which inhibit both MMPs and TNF-α convertase are especially advantageous for the treatment or prophylaxis of disease conditions in which both mechanisms are involved. Although compounds that both inhibit MMPs activity and TNF-α production have been disclosed in WIPO International Publication Nos. WO 94/24140 and WO 94/02466, the disclosures of which are herein incorporated by reference, there is still a need for effective MMP and/or TNF-α convertase inhibiting agents.

Because of their beneficial therapeutic effects, there is a need for effective inhibitors of metalloproteinase activity. The present invention is therefore directed to certain compounds that inhibit metalloproteinases, such as MMPs and TNF-α convertase, their pharmaceutically acceptable prodrugs, salts and solvates, pharmaceutical compositions containing the same and methods of using the same, as well as to method and intermediates useful in their preparation. Additional features and advantages of the invention will be set forth in the description which follows, and in part will be apparent from the description or may be learned from practice of the invention.

To achieve these and other advantages, the present invention provides a compound of formula 1:

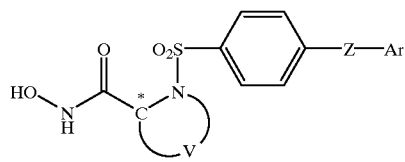

wherein Z is O or S; V is a divalent radical which together with C* and N forms a ring having six ring atoms, where each of said ring atoms other than C* and N independently is unsubstituted or substituted by a suitable substituent, and at least one of said other ring atoms is a heteroatom selected from O, N and S, and the remainder are carbon atoms; and Ar is an aryl or heteroaryl group; or a pharmaceutically acceptable prodrug, salt or solvate thereof.

Preferred compounds of the formula 1 include those having the formula 1-a:

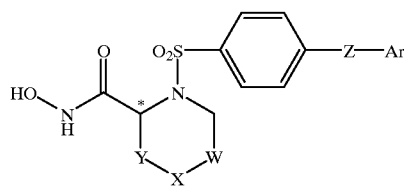

wherein

W, X and Y are each, independently of one another, $CR_1R_2$, C=O, S, S=O, $SO_2$, O, N—$R_3$, or $N^+(O^-)$—$R_4$, where $R_1$ and $R_2$ are independently selected from H and a suitable organic moiety, or wherein $R_1$ and $R_2$ together form a cycloalkyl group or a heterocycloalkyl group, $R_3$ is hydrogen or a suitable organic moiety, and $R_4$ is an alkyl group, with the proviso that at least one, but not all, of W, X, and Y are selected from $CR_1R_2$ and C=O, or a pharmaceutically acceptable prodrug, salt, or solvate thereof.

The invention is also directed to a method of inhibiting the activity of a metalloproteinase, such as an MMP or TNF-α convertase, by administering a compound of the formula 1 or 1-a, or a pharmaceutically acceptable prodrug, salt or solvate thereof. The invention is further directed to a pharmaceutical composition comprising an effective amount of a compound of the formula 1 or 1-a or a pharmaceutically acceptable prodrug, salt or solvate thereof.

The invention is still further directed to a method for making compounds of the formula 1 or 1-a involving one or more reactions as follows, wherein the variables in the formulas below are defined beginning at page 11:

(1) converting a compound of formula 2:

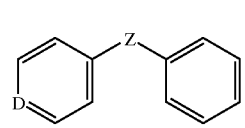

or a salt or solvate thereof, to a compound of formula 3:

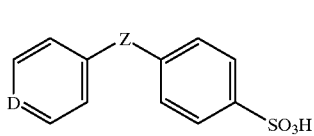

or a salt or solvate thereof, under conditions sufficient to form a compound of formula 3;

(2) converting a compound of formula 3 above, or a salt or solvate thereof, to a compound of formula 4:

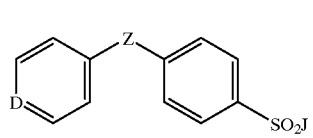

or a salt or solvate thereof, under conditions sufficient to form a compound of formula 4, or a salt or solvate thereof;

(3) converting a compound of formula 2 above, or a salt or solvate thereof, to a compound of formula 4 above, or a salt or solvate thereof, under conditions sufficient to form a compound of formula 4, or a salt or solvate thereof;

(4) converting a compound of formula 5:

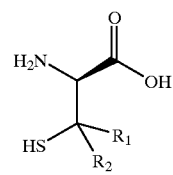

or a salt or solvate thereof, to a compound of formula 6:

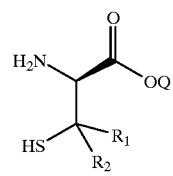

or a salt or solvate thereof, under conditions sufficient to form a compound of formula 6, or a salt or solvate thereof;

(5) converting a compound of formula 6 above, or a salt or solvate thereof, to a compound of formula 7:

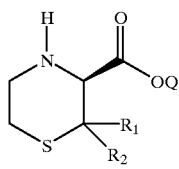

(7)

or a salt or solvate thereof, under conditions sufficient to form a compound of formula 7, or a salt or solvate thereof;

(6) converting a compound of formula 11:

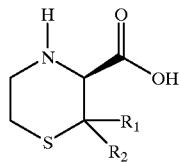

(11)

or a salt or solvate thereof, to a compound of formula 7 above, or a salt or solvate thereof, under conditions sufficient to form said compound of formula 7, or a salt or solvate thereof;

(7) converting a compound of formula 5 above, or a salt or solvate thereof, to a compound of formula 11 above, or a salt or solvate thereof, under conditions sufficient to form said compound of formula 11, or a salt or solvate thereof;

(8) reacting a compound of formula 7 above, or a salt or solvate thereof, or a compound of formula 11 above, or a salt or solvate thereof, with a compound of formula 4 above, or a salt of solvate thereof, under conditions sufficient to form a compound of formula 8:

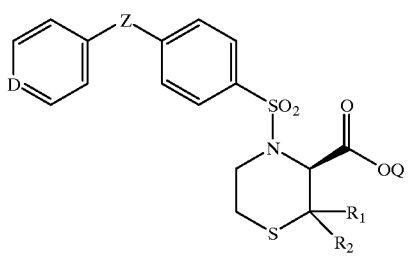

(8)

or a salt or solvate thereof;

(9) converting a compound of formula 8 above, or a salt or solvate thereof, to a compound of formula 9:

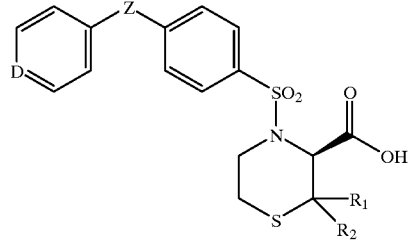

(9)

or a salt or solvate thereof, under conditions sufficient to form a compound of formula 9, or a salt or solvate thereof;

(10) converting a compound of formula 4 above, or a salt or solvate thereof, to a compound of formula 9 above, or a salt or solvate thereof, under conditions sufficient to form a compound of formula 9, or a salt or solvate thereof;

(11) converting a compound of formula 7 above, or a salt or solvate thereof, to a compound of formula 9 above, or a salt or solvate thereof, under conditions sufficient to form a compound of formula 9, or a salt or solvate thereof;

(12) converting a compound of formula 9 above, or a salt or solvate thereof, to a compound of formula 10:

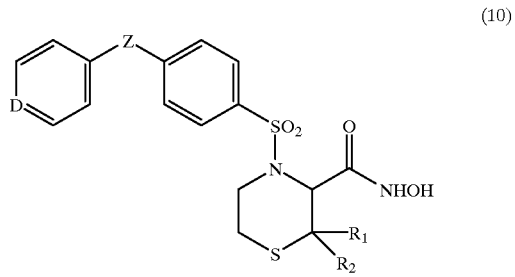

(10)

or a salt or solvate thereof, under conditions sufficient to form a compound of formula 10, or a salt or solvate thereof; and

(13) converting a compound of formula 7 above, or a salt or solvate thereof, to a compound of formula 10 above, or a salt or solvate thereof, under conditions sufficient to form a compound of formula 10, or a salt or solvate thereof.

In the above-described conversions and reactions, the following definitions apply:

D is N or C—$R_{16}$, wherein $R_{16}$ is an alkyl group, a cycloalkyl group, a heterocycloalkyl group, an aryl group, or a heteroaryl group, Z is O or S, J is a halogen, 1,2,4-triazolyl, benzotriazolyl or imidazol-1-yl, $R_1$ and $R_2$ are as defined above, and Q is a cycloalkyl group, an aryl group, a heteroaryl group, a heterocycloalkyl group, or a group of formula

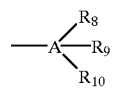

where in A is C or Si, and $R_8$, $R_9$, and $R_{10}$ are independently selected from H and any suitable organic moieity, or a salt or solvate thereof, with the provisos that:

for conversion (1) above, when D is C—$R_{16}$, $R_{16}$ is a heteroaryl group, and for conversion (4) above, the compound, salt or solvate of formula 6 is not a diester and Q is not methyl, ethyl, isopropyl, n-butyl, —CH$_2$-phenyl,

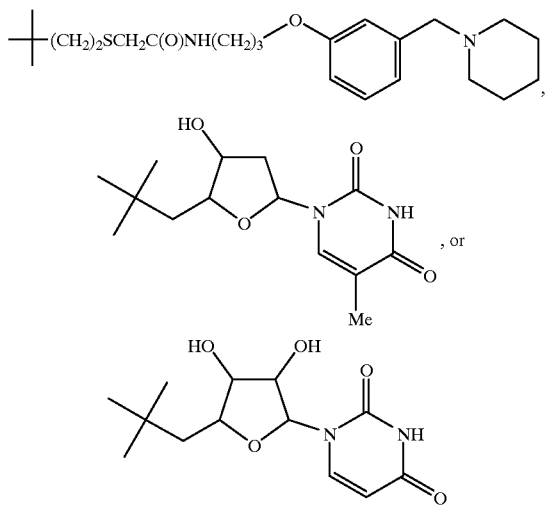

Additionally, the present invention is directed to compounds of formulas 3, 4, 6, 7, 8, and 9 above. For the compounds, salts and solvates of formula 3 above, when D is C—$R_{16}$, $R_{16}$ is a heteroaryl group. Further, the compound, salt or solvate of formula 6 is not a diester. Additionally, for the compounds, salts, and solvates of formula 6, Q is not methyl, ethyl, isopropyl, n-butyl, —CH$_2$-phenyl,

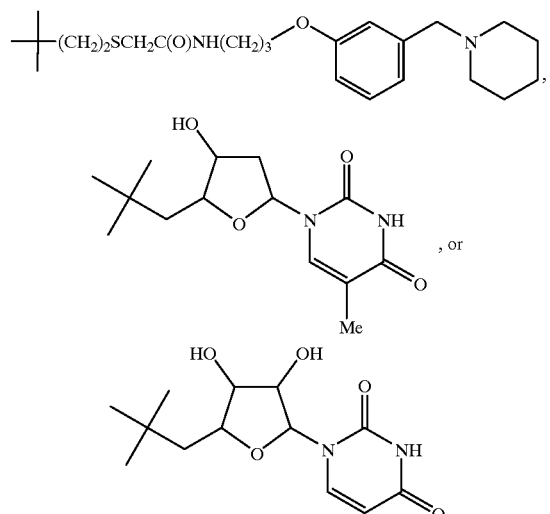

Preferred embodiments of the above-identified compounds, compositions, and methods are discussed in more detail below following the definitions.

As used in the present application, the following definitions apply, unless otherwise indicated:

An "alkyl group" is intended to mean a straight or branched chain monovalent radical of saturated and/or unsaturated carbon atoms and hydrogen atoms, such as methyl, ethyl, propyl, isopropyl, butyl, isobutyl, t-butyl, ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable substituents as defined below.

An "O-alkyl group" or "alkoxy group" is intended to mean an oxygen bonded to an alkyl group, wherein the alkyl group is as defined above.

A "cycloalkyl group" is intended to mean a non-aromatic, monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more suitable substituents. Illustrative examples of cycloalkyl groups include, but are not limited to, cyclopropyl, cyclobutyl, cyclopentyl, cyclopentenyl, cyclohexyl, cyclohexenyl, cycloheptyl, cyclooctyl, bicyclo[2.2.1.]heptyl, bicyclo[2.2.1.]hept-2-en-5-yl, bicyclo[2.2.2]octyl, bicyclo[3.2.1.]nonyl, bicyclo[4.3.0]nonyl, bicyclo[4.4.0]decyl, indan-1-yl, indan-2-yl, tetralin-1-yl, tetralin-2-yl, adamantyl, and the like.

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen and sulfur, wherein the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like.

An "aryl group" is intended to mean an aromatic, monovalent monocyclic, bicyclic, or tricyclic radical containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, phenyl, naphthyl, fluoren-2-yl, indan-5-yl, and the like.

A "heteroaryl group" is intended to mean an aromatic monovalent monocyclic, bicyclic, or tricyclic radical containing 5, 6, 7, 8, 9, 10, 11, 12, 13, 14, 15, 16, 17, or 18 ring atoms, including 1, 2, 3, 4, or 5 heteroatoms selected from nitrogen, oxygen and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include, but are not limited to, pyrrolyl, imidazolyl, pyrazolyl, furyl, thienyl, thiazolyl, oxazolyl, isoxazolyl, isothiazolyl, oxadiazolyl, triazolyl, tetrazolyl, pyrazinyl, pyridyl, pyrimidyl, pyridazinyl, indolyl, isoindolyl, benzimidazolyl, benzofuryl, isobenzofuryl, benzothienyl, quinolyl, isoquinolyl, phthalazinyl, carbazolyl, purinyl, pteridinyl, acridinyl, phenanthrolinyl, phenoxazinyl, phenothiazinyl, and the like, An "acyl group" is intended to mean a —C(O)—R— radical, wherein R is any suitable substituent as defined below.

A "sulfonyl group" is intended to mean a —S(O)(O)—R— radical, wherein R is any suitable substituent as defined below.

The term "suitable substituent" is intended to mean any of the substituents recognizable to those skilled in the art as not adversely affecting the inhibitory activity of the inventive compounds. Illustrative examples of suitable substituents include, but are not limited to, oxo groups, alkyl groups, hydroxy groups, halo groups, cyano groups, nitro groups, cycloalkyl groups, heterocycloalkyl groups, aryl groups, heteroaryl groups, trialkylsilyl groups, groups of formula (A)

(A)

wherein $R_a$ is hydrogen, an alkyl group, a cycloalkyl group, a heterocycloalkyl group, an aryl group, or a heteroaryl group, groups of formula (B)

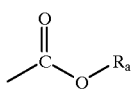

(B)

wherein $R_a$ is hydrogen, an alkyl group, a cycloalkyl group, a heterocycloalkyl group, an aryl group, or a heteroaryl group, groups of formula (C)

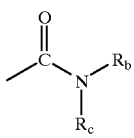

(C)

wherein $R_b$ and $R_c$ are independently hydrogen, an alkyl group, a cycloalkyl group, a heterocycloalkyl group, an aryl group, or a heteroaryl group, groups of formula (D)

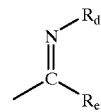

(D)

wherein $R_d$ is hydrogen, an alkyl group, a cycloalkyl group, a heterocycloalkyl group, an aryl group, a heteroaryl group, a hydroxy group, an alkoxy group, an amino group, an alkylamino group, a dialkylamino group, or an acylamino group; and $R_e$ is hydrogen, an alkyl group, a cycloalkyl group, a heterocycloalkyl group, an aryl group, a heteroaryl group, an amino group, an alkylamino group, or a dialkylamino group, groups of formula (E)

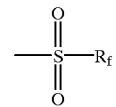

(E)

wherein $R_f$ is an alkyl group, a cycloalkyl group, a heterocycloalkyl group, an aryl group, or a heteroaryl group, groups of formula (F)

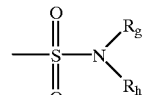

(F)

wherein $R_g$ and $R_h$ are independently hydrogen, an alkyl group, a cycloalkyl group, a heterocycloalkyl group, an aryl group, or a heteroaryl group, groups of formula (G)

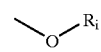

(G)

wherein $R_i$ is an alkyl group, a cycloalkyl group, a heterocycloalkyl group, an aryl group, a heteroaryl group, or a group of formula (A), formula (B), formula (C), formula (H), or formula (K), groups of formula (H)

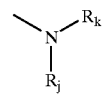

(H)

wherein $R_j$ is hydrogen, an alkyl group, a cycloalkyl group, a heterocycloalkyl group, an aryl group, a heteroaryl group, a hydroxy group, an alkoxy group, an amino group, or a group of formula (A), formula (B), formula (C) or formula (D); and wherein $R_k$ is hydrogen, an alkyl group, a cycloalkyl group, a heterocycloalkyl group, an aryl group, a heteroaryl group, or a group of formula (A), formula (B), formula (C), formula (D), formula (E), or formula (F), groups of formula (J)

wherein $R_l$ is hydrogen, an alkyl group, a cycloalkyl group, a heterocycloalkyl group, an aryl group, a heteroaryl group, or a group of formula (C), and groups of formula (K)

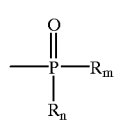

wherein $R_m$ and $R_n$ are independently an alkyl group, a cycloalkyl group, a heterocycloalkyl group, an aryl group, a heteroaryl group, a hydroxy group, an alkoxy group, an amino group, an alkylamino group, or a dialkylamino group.

The term "suitable organic moiety" is intended to mean any organic moiety recognizable to those skilled in the art as not adversely affecting the inhibitory activity of the inventive compounds. Illustrative examples of suitable organic moieties include, but are not limited to oxo groups, alkyl groups, hydroxy groups, halo groups, cyano groups, nitro groups, cycloalkyl groups, heterocycloalkyl groups, aryl groups, heteroaryl groups, trialkylsilyl groups, and groups of formulas (A), (B), (C), (D), (E), (F), (G), (H), (J), and (K), as defined above.

A "hydroxy group" is intended to mean the radical —OH.

An "oxo group" is intended to mean the divalent radical =O.

A "halo group" or is intended to mean any of the radicals —F, —Cl, —Br, or —I.

A "cyano group" is intended to mean the radical —C≡N.

A "nitro group" is intended to mean the radical —NO$_2$.

A "trialkylsilyl group" is intended to mean the radical —SiR$_p$R$_q$R$_s$, where R$_p$, R$_q$, and R$_s$ are each independently an alkyl group.

A "carboxy group" is intended to mean a group of formula (B) wherein $R_t$ is hydrogen.

A "alkoxycarbonyl group" is intended to mean a group of formula (B) wherein $R_t$ is an alkyl group as defined above.

A "carbamoyl group" is intended to mean a group of formula (C) wherein $R_t$ and $R_t$ are both hydrogen.

An "amino group" is intended to mean the radical —NH$_2$.

An "alkylamino group" is intended to mean the radical —NHR$_u$, wherein $R_u$ is an alkyl group as defined above.

A "dialkylamino group" is intended to mean the radical —NR$_u$R$_v$, wherein $R_u$ and $R_v$, which are the same or different, are each an alkyl group as defined above.

A "pharmaceutically acceptable prodrug" is intended to mean a compound that is converted under physiological conditions or by solvolysis to a compound of the formula 1 or 1-a.

A "pharmaceutically acceptable solvate" is intended to mean a solvate that retains the biological effectiveness and properties of the biologically active components of compounds of formula 1 or 1-a.

Examples of pharmaceutically acceptable solvates include, but are not limited to, compounds of formula 1 or 1-a in combination with water, isopropanol, ethanol, methanol, DMSO, ethyl acetate, acetic acid, or ethanolamine.

In the case of solid formulations, it is understood that the inventive compounds may exist in different forms, such as stable and metastable crystalline forms and isotropic and amorphous forms, all of which are intended to be within the scope of the present invention.

A "pharmaceutically acceptable salt" is intended to mean those salts that retain the biological effectiveness and properties of the free acids and bases and that are not biologically or otherwise undesirable.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If the inventive compound is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

Additionally preferred is a compound of the formula 1-f:

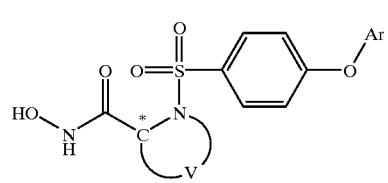

wherein V is as defined above and Ar is a monocyclic aryl group or monocyclic heteroaryl group, or a pharmaceutically acceptable prodrug or a pharmaceutically acceptable salt thereof. More preferred is a compound having the formula 1-g

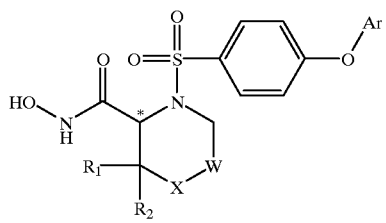

1-g wherein W and X are independently selected from $CH_2$, C=O, S, S=O, O, N—$R_3$, and $N^+(O^-)$—$R_4$, where $R_3$ is a hydrogen atom or a suitable substituent, and $R_4$ is a $C_1$–$C_7$ alkyl group, wherein the alkyl group is a straight or branched chain monovalent radical of carbon and hydrogen atoms having no unsaturation, which is optionally substituted by one or more suitable substituents, provided that when W is $CH_2$ or C=O, X is not $CH_2$ or C=O; and $R_1$ and $R_2$ are independently selected from a hydrogen atom, a $C_1$–$C_7$ alkyl group, a —C(O)O$R_{17}$ group, or a —C(O)N$R_{17}R_{18}$ group, wherein $R_{17}$ and $R_{18}$ are independently selected from hydrogen and an alkyl group, and wherein the alkyl group is a straight or branched chain monovalent radical of carbon and hydrogen atoms having no unsaturation, which is optionally substituted by one or more suitable substituents, or $R_1$ and $R_2$ together form a monocyclic cycloalkyl group or a monocyclic heterocycloalkyl group; or a pharmaceutically acceptable prodrug thereof or a pharmaceutically acceptable salt thereof.

Preferably, in the above formulas 1, 1-a, 1-f, and 1-g, Ar is a monocyclic aryl group or a monocyclic heteroaryl group. When Ar is a monocyclic aryl group, preferably it is unsubstituted or substituted at the meta position and/or the para position with a suitable substituent. Preferably, the substituent is a halogen atom, an aryl or heteroaryl group, an alkoxy group, or an alkyl group, wherein the alkyl group is a straight or branched chain monovalent radical of carbon and hydrogen atoms having no unsaturation, which is optionally substituted by one or more suitable substitutents. Even more preferably, Ar is an aryl group that is substituted at the para position with a halogen atom, an alkoxy group or a monocyclic heteroaryl group. Particularly preferred embodiments of the present invention include those where Ar is 4-fluorophenyl, 4-chlorophenyl, 4-methoxyphenyl 4-(imidazol-1-yl)phenyl or 4-(imidazol-2-yl)phenyl. Preferably when Ar is a monocyclic heteroaryl group, Ar is a pyrid-4-yl group.

In formula 1-a, preferably Y is $CR_1R_2$, where $R_1$ and $R_2$ are independently selected from H and any suitable organic moiety. Preferably $R_1$ and $R_2$ are independently selected from H, an alkyl group, a cycloalkyl group, a heterocycloalkyl group, an aryl group, a heteroaryl group, $OR_5$, $SR_5$, $NR_5R_6$, and $C(O)R_7$, where $R_5$ is an alkyl group, a cycloalkyl group, a heterocycloalkyl group, an aryl group, a heteroaryl group, or $C(O)NR_{13}R_{14}$, where $R_{13}$ and $R_{14}$ are independently selected from H, an alkyl group, a cycloalkyl group, a heterocycloalkyl group, an aryl group, and a heteroaryl group, or $R_{13}$ and $R_{14}$, together with the nitrogen atom to which they are attached form a heterocycloalkyl group, $R_6$ is H, an alkyl group, a cycloalkyl group, a heterocycloalkyl group, an aryl group, a heteroaryl group, C(O)O—$R_{15}$, C(O)S—$R_{15}$, or $SO_2$—$R_{15}$, wherein $R_{15}$ is an alkyl group, a cycloalkyl group, a heterocycloalkyl group, an aryl group, or a heteroaryl group, $R_7$ is OH, an alkyl group, a cycloalkyl group, a heterocyclolalkyl group, an aryl group, a heteroaryl group, an O-alkyl group, $NR_{13}R_{14}$, or O—$R_{15}$, wherein $R_{13}$, $R_{14}$, and $R_{15}$ are independently as defined above, or $R_1$ and $R_2$ together form a cycloalkyl group or a heterocycloalkyl group. More preferably $R_1$ and $R_2$ are each a methyl group.

In formulas 1-a and 1-g, preferably $R_3$ is hydrogen, an alkyl group, a cycloalkyl group, a heterocycloalkyl group, an aryl group, a heteroaryl group, C(O)—$NR_{13}R_{14}$, C(O)—$OR_{15}$, C(O)—$SR_{15}$, $SO_2$—$R_{15}$, or C(O)—$R_{13}$ where $R_{13}$ and $R_{14}$ are independently selected from H, an alkyl group, a cycloalkyl group, a heterocycloalkyl group, an aryl group, and a heteroaryl group, or $R_{13}$ and $R_{14}$, together with the nitrogen atom to which they are attached form a heterocycloalkyl group, and $R_{15}$ is an alkyl group, a cycloalkyl group, a heterocycloalkyl group, an aryl group, or a heteroaryl group.

Preferably, when W is $CH_2$ or N—$R_3$, X is S, S=O, O, N—$R_3$, $N^+(O)$—$R_4$ or C=O. More preferably, when W is $CH_2$, X is O, S=O or N—$R_3$, and $R_3$ is a suitable substituent, preferably a hydrogen atom, an alkyl group, wherein said alkyl group is a straight or branched chain monovalent radical of carbon and hydrogen atoms having no unsaturation, which is optionally substituted by one or more suitable substituents, a C(O)—$R_{17}$ group, a C(O)O—$R_{17}$ group, a C(O)NH—$R_{17}$ group, a $C(O)NR_{17}R_{18}$ group, an $SO_2$—$R_{19}$ group, wherein $R_{17}$ and $R_{18}$ are each independently an alkyl group wherein said alkyl group is a straight or branched chain monovalent radical of carbon and hydrogen atoms having no unsaturation, which is optionally substituted by one or more suitable substituents, and wherein $R_{19}$ is a monocyclic aryl group or an alkyl group as defined above. More preferably, $R_3$ is a hydrogen atom, a $C_1$–$C_7$ alkyl group, or a $SO_2$—$R_{19}$ group, wherein $R_{19}$ is an alkyl group. Most preferably, when W is $CH_2$, X is O, S, S=O, N—H, N—($SO_2CH_3$) or N—($C_1$–$C_7$ alkyl).

Alternatively, when W is N—$R_3$, X is preferably C=O and $R_3$ is preferably a hydrogen atom or an alkyl group, more preferably a hydrogen atom.

Particularly preferred embodiments of the present invention include those compounds of the formula 1-a and 1-g where X is S, S=O, O, N—$R_3$ or $N^+(O^-)$—$R_4$ and W is $CH_2$; or X is S, O or N—$R_3$ and W is C=O; or X is C=O and W is N—$R_3$; or X is $CH_2$ and W is O, S or N—$R_3$, where $R_3$ is a C(O)—$R_{17}$ group, where $R_{17}$ is as defined above. According to these preferred embodiments of the present invention, $R_1$ and $R_2$ are preferably, independently of one another, a hydrogen atom or a methyl group, and Ar is preferably an aryl group which is unsubstituted or substituted in the para position with a suitable substituent, preferably a halogen atom, an alkoxy group or a heteroaryl group. More preferably, $R_1$ and $R_2$ are the same and Ar is an aryl group substituted in the para position with a fluorine atom, a chlorine atom, a methoxy group or an imidazolyl group.

Illustrative examples of compounds according to these preferred embodiments of the present invention include, but are not limited to, 3(S)-N-hydroxy-2,2-dimethyl-4-(4-(4-(imidazol-2-yl)phenoxy)benzenesulfonyl)-tetrahydro-2H-1,4-thiazine-3-carboxamide and 3(S)-N-hydroxy-2,2-dimethyl-4-(4-((pyrid-4-yl)oxy)benzenesulfonyl)-tetrahydro-2H-1,4-thiazine-3-carboxamide.

Other preferred embodiments of the present invention include those compounds where Y is N—$R_3$, where $R_3$ is a C(O)—$R_{17}$ group, a C(O)O—$R_{17}$ group, a C(O)NH—$R_{17}$ group, a C(O)NR$_{17}$R$_{18}$ group, an SO$_2$—$R_{19}$ group, wherein $R_{17}$ and $R_{18}$ are each independently an alkyl group wherein said alkyl group is a straight or branched chain monovalent radical of carbon and hydrogen atoms having no unsaturation, which is optionally substituted by one or more suitable substituents, and wherein $R_{19}$ is a monocyclic aryl group or an aryl group as defined above.

Also, according to the preferred embodiments of the present invention where X is N—$R_3$, $R_3$ is a hydrogen atom, an alkyl group or an alkylsulfonyl group, more preferably a hydrogen atom, a methyl group or a methanesulfonyl group. Illustrative examples of compounds according to these preferred embodiments of the present invention include, but are not limited to, (R)-N-hydroxy-1-(4-(4-chlorophenoxy)benzenesulfonyl)-4-(methanesulfonyl)-piperazine-2-carboxamide, (R)-N-hydroxy-1-(4-(4-fluorophenoxy)benzenesulfonyl)-4-(methanesulfonyl)-piperazine-2-carboxamide, (R)-N-hydroxy-1-(4-(4-methoxyphenoxy)benzenesulfonyl)4-(methanesulfonyl)-piperazine-2-carboxamide, (R)-N-hydroxy-1-(4-(4-chlorophenoxy)benzene-sulfonyl)-4-methylpiperazine-2-carboxamide, (R)-N-hydroxy-1-(4-(4-fluorophenoxy)-benzenesulfonyl)-4-methylpiperazine-2-carboxamide, (R)-N-hydroxy-1-(4-(4-chlorophenoxy)benzenesulfonyl)-piperazine-2-carboxamide, (R)-N-hydroxy-1-(4-(4-fluorophenoxy)benzene-sulfonyl)-piperazine-2-carboxamide, 3(S)-N-hydroxyl-4-(4-(4-chlorophenoxy)benzenesulfonyl-2,2-dimethyl-tetrahydro-2H-thiazine-3-carboxamide, 2(R)-3,3-dimethyl-N-hydroxy-1-(4-(4-chlorophenoxyl)benzenesulfonyl)-piperazine-2-carboxamide, 2(R)-3,3-dimethyl-N-hydroxy-1-(4-(4-fluorophenoxyl)benzenesulfonyl)-piperazine-2-carboxamide, 2(R)-3,3-dimethyl-N-hydroxy-1-(4-(4-bromophenoxyl)benzenesulfonyl)-piperazine-2-carboxamide, 2(R)-1-(4-(4-(chlorophenoxybenzenesulfonyl)-N-hydroxy-3,3,4-trimethylpiperazine-2-carboxamide, 2(R)-1-(4-(4-(fluorophenoxybenzenesulfonyl)-N-hydroxy-3,3,4-trimethylpiperazine-2-carboxamide, 3(S)-N-hydroxyl-4-(4-(4-chlorophenylsulfanyl)benzenesulfonyl-2,2-dimethyl-tetrahydro-2H-thiazine-3-carboxamide, 3(S)-N-hydroxyl-4-(4-(4-fluorophenylsulfanyl)benzenesulfonyl-2,2-dimethyl-tetrahydro-2H-thiazine-3-carboxamide, 2(R)-3,3-dimethyl-N-hydroxy-1-(4-(4-fluorophenylsulfanyl)benzenesulfonyl)-piperazine-2-carboxamide, 2(R)-3,3-dimethyl-N-hydroxy-1-(4-(4-chlorophenylsulfanyl)benzenesulfonyl)-piperazine-2-carboxamide, 2(R)-1-(4-(4-(fluorophenylsulfanyl)benzenesulfonyl)-N-hydroxy-3,3,4-trimethylpiperazine-2-carboxamide, 2(R)-1-(4-(4-(chlorophenylsulfanyl)benzenesulfonyl)-N-hydroxy-3,3,4-trimethylpiperazine-2-carboxamide, 2(R),3(S)-N-hydroxyl-4-(4-(pyrid-4-yl)oxy)benzenesulfonyl)-2-methyl-tetrahydro-2H-thiazine-3-carboxamide, 2(R),3(S)-N-hydroxyl-4-(4-(pyrid-4-yl)sulfanyl)benzenesulfonyl)-2-methyl-tetrahydro-2H-thiazine-3-carboxamide, and a compound of formula:

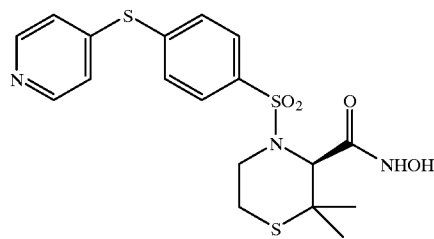

The inventive compounds may exist as single stereoisomers, racemates and/or mixtures of enantiomers and/or diastereomers. All such single stereoisomers, racemates and mixtures thereof are intended to be within the scope of the present invention.

Preferably, the hydroxamate-bearing carbon, i.e., the carbon atom designated with "*" in formulas 1-a and 1-g, is in the "R" configuration when X is CH$_2$, C=O, O, N—$R_3$, or N$^+$(O$^-$)—$R_4$ and in the "S" configuration when X is S or S=O. It is understood by those skilled in the art that this difference in designating configuration is a consequence of the sequence rules of the Cahn-Ingold-Prelog system. When X is S=O, the sulfur atom is also preferably in the "R" configuration in relation to the preferred "S" configuration at the hydroxamate-bearing carbon atom. Thus a preferred compound is a compound of the formula:

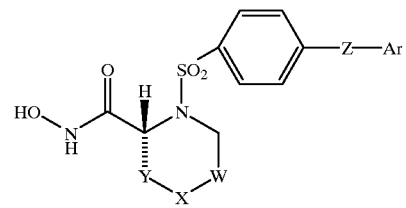

wherein X, W, Y, Z, and Ar are as defined above for formula 1-a. As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

In the above described methods and intermediates, for conversions 1, 2, and 8–12 and for compounds 3, 4, 8, 9, and 10 preferably D is N. For conversions 2, 8, and 10 and for compound 4, preferably J is Cl. Particularly preferred intermediates of formula 4 useful in conversions 2, 8, and 10 are salts of formulas 4a and 4b:

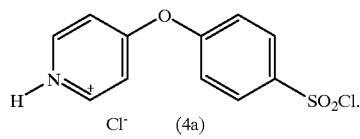

-continued

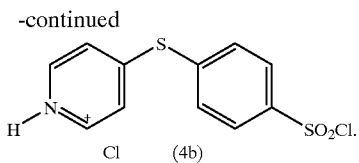

For conversions 5 and 6 and 8–13 and for compounds 7, 8, and 9, when Q is a group of formula:

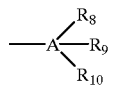

and A is C, preferably $R_8$ is H, an alkyl group, an O-alkyl group, an S-alkyl group, a cycloalkyl group, a heterocycloalkyl group, an aryl group, a heteroaryl group, C=N, or $C(O)R_{11}$, wherein $R_{11}$ is an alkyl group, an aryl group, a cycloalkyl group, a heteroaryl group, or a heterocycloalkyl group, and $R_9$ and $R_{10}$ are independently selected from H, an alkyl group and an aryl group. For these same conversions and compounds, when A is Si, preferably $R_8$, $R_9$ and $R_{10}$ are independently selected from an alkyl group, a cycloalkyl group, and an aryl group. More preferably, for these conversions and compounds Q is $CH_3$, $CH_2CH_3$, $CH(CH_3)_2$, $C(CH_3)_3$, $CH_2$—CH=$CH_2$, $CH_2C$=N, or a group of the formula:

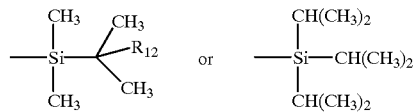

wherein $R_{12}$ is $CH_3$ or $CH(CH_3)_2$.

For conversion 4 and for compound 6, preferred embodiments of the inventive methods and compounds are those such that when Q is an $A(R_8)(R_9)(R_{10})$ group as shown above and A is C, preferably $R_8$ is H, an alkyl group, an O-alkyl group, an S-alkyl group, a cycloalkyl group, a heterocycloalkyl group, an aryl group, a heteroaryl group, C=N, or $C(O)R_{11}$, wherein $R_{11}$ is an alkyl group, an aryl group, a cycloalkyl group, a heteroaryl group, or a heterocycloalkyl group, and $R_9$ and $R_{10}$ are independently selected from H, an alkyl group and an aryl group. For this same conversion and compound, when A is Si, preferably $R_8$, $R_9$ and $R_{10}$ are independently selected from an alkyl group, a cycloalkyl group, and an aryl group. More preferably, for this conversion and compound, Q is $CH_3$, $CH_2CH_3$, $CH(CH_3)_2$, $C(CH_3)_3$, $CH_2$—CH=$CH_2$, $CH_2C$=N, or a group of the formula:

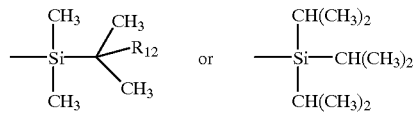

wherein $R_{12}$ is $CH_3$ or $CH(CH_3)_2$.

For conversions 3–13 and for intermediates 6, 7, 8, and 9, preferably $R_1$ and $R_2$ are each a methyl group.

Particularly preferred compounds of formula 8, useful in conversions 8 and 9, are those of formula 8a, where D is N, $R_1$ and $R_2$ are each a methyl group, and Z is O, and of formula 8b, where D is N, $R_1$ and $R_2$ are each a methyl group, and Z is S. For compounds 9 and 10, preferably D is N and $R_1$ and $R_2$ are each a methyl group.

The present invention is further directed to methods of inhibiting metalloproteinase activity, for example in mammalian tissue, by administering a compound of the formula 1, 1-a, 1-f or 1-g, or a pharmaceutically acceptable prodrug, salt or solvate thereof. The activity of the inventive compounds as inhibitors of metalloproteinase activity, such as the activity of MMPs (including stromelysins, collagenases, gelatinases and/or matrilysin) and/or TNF- convertase, may be measured by any of the methods available to those skilled in the art, including in vivo and/or in vitro assays. Examples of suitable assays for activity measurements include those described in *Anal. Biochem.*, vol. 147, p. 437 (1985), *Anal Biochem.*, vol. 180, p. 110 (1989), *FEBS*, vol. 96, p. 263 (1992) and European Patent Application No. 0 606 046.

Administration of the compounds of the formula 1, 1-a, 1-f or 1-g, or their pharmaceutically acceptable prodrugs, salts or solvates, may be performed according to any of the accepted modes of administration available to those skilled in the art. Illustrative examples of suitable modes of administration include oral, nasal, parenteral, topical, transdermal and rectal. Preferably, the mode of administration is oral.

The inventive compounds of the formula 1, 1-a, 1-f or 1-g, or their pharmaceutically acceptable prodrugs, salts or solvates, may be administered as a pharmaceutical composition in any suitable pharmaceutical form recognizable to the skilled artisan. Suitable pharmaceutical forms include, but are not limited to, solid, semisolid, liquid or lyophilized formulations, such as tablets, powders, capsules, suppositories, suspensions and aerosols. Preferably, the pharmaceutical form is a tablet or capsule for oral administration. The pharmaceutical composition may also include suitable excipients, diluents, vehicles and carriers as well as other pharmaceutically active agents, depending upon the intended use.

Acceptable methods of preparing suitable pharmaceutical forms of the pharmaceutical compositions are known to those skilled in the art. For example, pharmaceutical preparations may be prepared following conventional techniques of the pharmaceutical chemist involving steps such as mixing, granulating and compressing when necessary for tablet forms, or mixing, filling, and dissolving the ingredients as appropriate, to give the desired products for oral, parenteral, topical, intravaginal, intranasal, intrabronchial, intraocular, intraaural and/or rectal administration. Illustrative examples of such methods include those described in *Remington's Pharmaceutical Sciences*, 18th edition (1990).

Solid or liquid pharmaceutically acceptable carriers, diluents, vehicles or excipients may be employed in the pharmaceutical compositions. Illustrative solid carriers include starch, lactose, calcium sulphate dihydrate, terra alba, sucrose, talc, gelatin, agar, pectin, acacia, magnesium stearate and stearic acid. Illustrative liquid carriers include syrup, peanut oil, olive oil, saline solution and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), or a nonaqueous or aqueous liquid suspension.

A dose of the pharmaceutical composition contains at least a therapeutically effective amount of the active compound (i.e., a compound of the formula 1, 1-a, 1-f or 1-g, or their pharmaceutically acceptable prodrugs, salts or solvates) and preferably is made up of one or more pharmaceutical dosage units. An exemplary dosage unit for a mammalian host contains an amount of from 0.1 milligram up to 500 milligrams of active compound per kilogram body weight of the host, preferably 0.1 to 200 milligrams, more preferably 50 milligrams or less, and even more preferably about 10 milligrams or less, per kilogram of the host weight.

The selected dose may be administered to a mammal, for example, a human patient in need of treatment mediated by inhibition of metalloproteinase activity, by any known method of administrating the dose including: topically, for example, as an ointment or cream; orally; rectally, for example, as a suppository; parenterally by injection; or continuously by intravaginal, intranasal, intrabronchial, intraaural or intraocular infusion.

The amount of the inventive compounds, salts, solvates and/or prodrugs to be administered will vary based upon a number of factors, including the specific metalloproteinase to be inhibited, the degree of inhibition desired, the characteristics of the mammalian tissue in which inhibition is desired, the metabolic stability and activity of the particular inventive compound employed, and the mode of administration. One skilled in the art may readily determine a suitable dosage according to methods known to the art. Preferably, the amount of inventive compound of the formula 1, 1-a, 1-f or 1-g, or their pharmaceutically acceptable prodrugs, salts or solvates, administered is between 0.1 mg/kg body weight and 100 mg/kg body weight per day.

The inventive compounds, and the salts, solvates, and prodrugs thereof, may be prepared by employing the techniques available in the art using starting materials that are readily available. Exemplary methods of preparing the inventive compounds are described below. In the following schemes, unless otherwise indicated, W, X, Y, Z, Ar, $R_1$ and $R_2$ are as previously defined herein.

The inventive compounds of the formula 1-a preferably can be prepared by reacting a compound of the formula 12-a (where M is a hydroxy group) with hydroxylamine in the presence of a suitable peptide coupling reagent. Illustrative examples of suitable peptide coupling agents include 1,1'-carbonyldiimidazole, N-(dimethylaminopropyl)-N'-ethyl carbodiimide ("EDC"), benzotriazol-1-yloxy-tris(dimethylamino) phosphonium hexafluorophosphate, or propanephosphonic anhydride in an inert polar solvent, such as dimethylformamide ("DMF").

tetrahydrofuran ("THF")-dichloromethane, preferably at 0 to 25° C., to give hydroxamates of the formula 1-a.

Compounds of the formula 12-b are preferably prepared in a form that is directly useful for further reaction without isolation. For example, such compounds can be prepared by allowing compounds of the formula 12-a to react with a suitable halogenating agent, such as thionyl chloride or oxalyl chloride, preferably in the presence of a catalytic amount of dimethylformamide, and preferably in a suitable solvent such as dichloromethane at a temperature from 0° C. to room temperature.

Alternatively, the coupling reactions described above can be carried out with compounds of the formula 12-a or 12-b and oxygen-protected compounds of hydroxylamine (i.e., where Pg is a suitable protecting group known to those skilled in the art, such as benzyl, t-butyl, t-butyldimethylsilyl, or t-butyldiphenylsilyl, and/or described in T. W. Greene and P. G. M. Wuts, *Protective Groups in Organic Synthesis* (1991), the disclosure of which is incorporated herein by reference) to give compounds of formula 13. Deprotection of compounds of the formula 13 provides compounds of formula 1-a. Suitable methods of deprotecting compounds of the formula 13 are known in the art, for example, as described in T. W. Greene and P. G. M. Wuts, *Protective Groups in Organic Synthesis* (1991).

Compounds of the formula 12-a can be prepared by alkaline hydrolysis of the corresponding ester 12-c (where M=OQ, and Q is a suitable protecting group such as methyl, ethyl, allyl, benzyl or t-butyl) using a suitable aqueous base, such as lithium hydroxide, sodium hydroxide, or potassium hydroxide, preferably in a homogeneous aqueous-organic solvent mixture at a temperature from 0° C. to 25° C. Alternatively, these compounds can also be prepared by acidic hydrolysis of the corresponding ester using a suitable aqueous acid, such as hydrochloric acid in aqueous dioxane, at a suitable temperature, preferably from 50° C. to 100° C. Other methods recognizable by those skilled in the art as

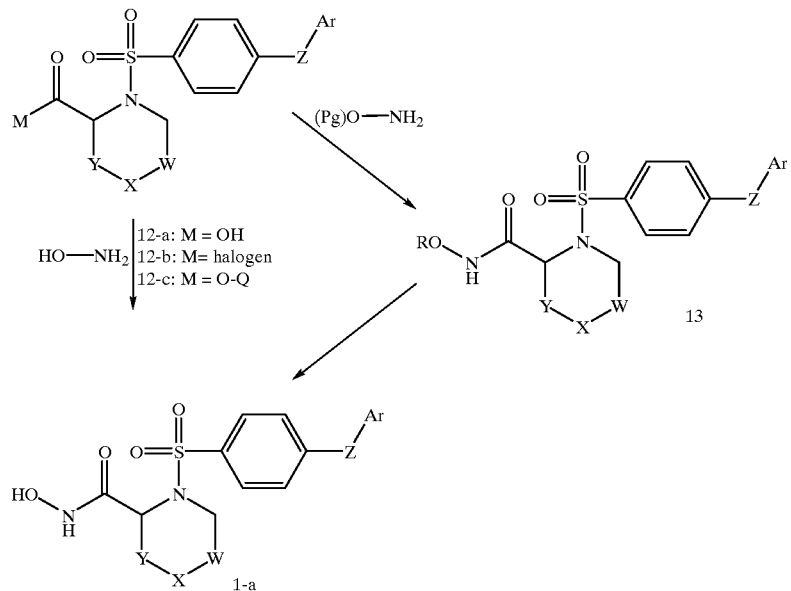

Alternatively, a compound of the formula 12-b (where M is a halogen such as chlorine) can be reacted with hydroxylamine in a suitable solvent mixture such as tert-butanolsuitable for converting esters to acids can also be employed, such as hydrogenolysis of benzyl esters using hydrogen and palladium on carbon, acid-promoted cleavage of t-butyl esters under anhydrous conditions, and palladium-catalyzed cleavage of allyl esters.

Compounds of the formula 1-c (i.e., 1-a, where W is $CH_2$ and Y is $CR_1R_2$ and X is N—$R_3$) in which $R_3$ is an alkyl group, can be prepared directly from compounds of the formula 1-b, for example by treatment with a suitable alkylating agent, such as an alkyl halide or alkyl sulfonate ester, in a suitable solvent at an appropriate temperature, such as THF at a temperature from 0° C. to 50° C.

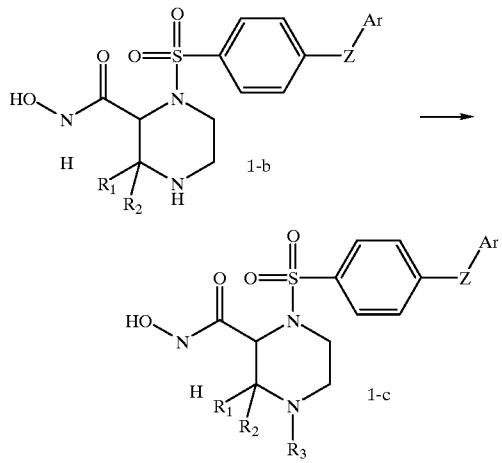

Compounds of the formula 1-c where $R_3$ is an alkylsulfonyl group or an arylsulfonyl group can also be prepared directly from compounds of the formula 1-b. For example, treatment compunds of formula 1-b with 2 equivalents of trimethylchlorosilane in the presence of an excess of a tertiary base, such as 4-methylmorpholine, in an aprotic solvent, such as dichloromethane, at 25° C., followed by treatment with an alkylsulfonyl chloride or an arylsulfonyl chloride at a temperature from 0° C. to 25° C. leads to, after a conventional aqueous work-up, compounds of formula 1-c where $R_3$ is alkylsulfonyl or arylsulfonyl. In a similar manner, compounds of formula 1-b can be reacted with the appropriate electrophilic carbonyl reagents to provide compounds of formula 1-c where $R_3$ is CO—$R_3'$, where $R_3'$ is any suitable organic moiety.

Compounds of formula 16 (i.e., 12-a where W and Y are $CH_2$ and X is N—$R_3$) can be prepared according to the following scheme.

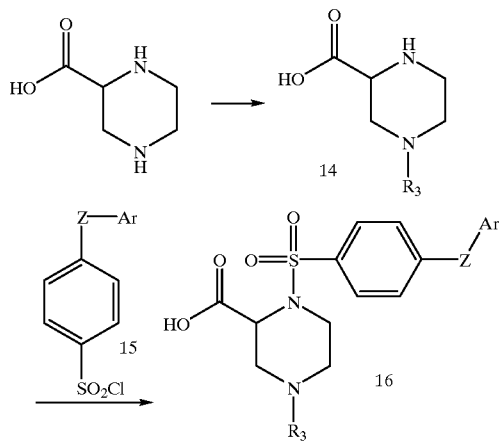

Preferably, commercially available racemic piperazine-2-carboxylic acid is allowed to react with a suitable electrophilic reagent $R_3$-Lg, where Lg is any suitable leaving group, under conditions such that the reaction takes place predominantly at the N-4 position to give compounds of the formula 14. More preferably, the reaction takes place in aqueous-organic solvent, such as acetonitrile-water, at a temperature from −20° C. to 25° C., and in the presence of excess base such as triethylamine.

For the preparation of enantiomerically pure compounds of the formula 16, racemic piperazine-2-carboxylic acid can be first resolved according to known methods, such as those described in *Helv. Chim. Acta,* vol. 43, p. 888 (1960), and *Helv. Chim. Acta,* vol. 72, p. 1043 (1989), the disclosures of which are incorporated herein by reference.

Examples of suitable electrophilic reagents $R_3$-Lg with suitable regioselectivity include BOC-ON, di-t-butyl dicarbonate, N-(benzyloxycarboxy)succinimide, and acetic anhydride. The intermediate of the formula 14 is then preferably further reacted, without isolation, under the same conditions with a sulfonyl chloride of the formula 15 to give compounds of the formula 16.

Alternatively, the intermediate of the formula 14 can be isolated and then allowed to react with trimethylsilyl chloride and a suitable tertiary amine base, such as triethylamine or 4-methylmorpholine. Without isolation, the resulting material is then reacted with a sulfonyl chloride 15 in a suitable solvent such as dichloromethane at 25° C. to provide, after conventional acid workup, a compound of the formula 16.

The intermediate of the formula 14 can also be prepared by treating the copper (II) complex of piperazine-2-carboxylate, prepared according to the method described in U.S. Pat. No. 4,032,639, the disclosure of which is herein incorporated by reference, with $R_3$-Lg, followed by decomplexation by acidification and ion-exchange chromatography using DOWEX 50 resin. With this procedure, a broad range of electrophilic reagents $R_3$-Lg can be employed.

Compounds of formula 15 can be preferably prepared by treatment of the corresponding aryl/heteroaryl phenyl ether or aryl/heteroaryl phenyl thioether, which are commercially available or can be prepared by methods known to those skilled in the art, with an excess of chlorosulfonic acid in dichloromethane solution at a temperature from 0° C. to 25° C.

Alternatively, the aryl phenyl ether can be treated with between 0.9 and 1.2 molar equivalents of chlorosulfonic acid at −20° C. to 25° C. The resulting sulfonic acid, with or without isolation, can be subsequently converted to the sulfonyl chloride 15 with an excess of a chlorinating reagent, such as oxalyl chloride or thionyl chloride, in the presence of a catalytic amount of dimethylformamide ("DMF") in a suitable solvent, such as dichloromethane, 1,2-dichloroethane, or acetonitrile, at 25° C. to 80° C.

Alternatively, compounds of the formula 16-a, where Pg is a suitable protecting group as described above, are first converted to the corresponding methyl esters 17 by conventional methods, such as treatment with trimethylsilyl diazomethane in a suitable solvent such as methanol-dichloromethane at room temperature as shown in the following scheme.

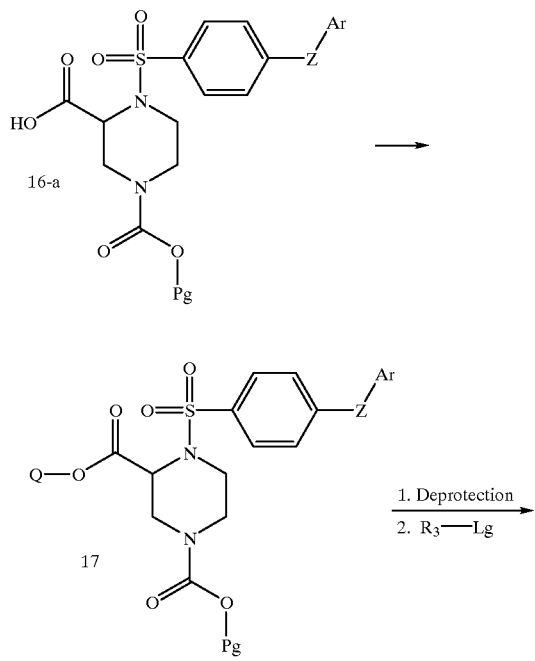

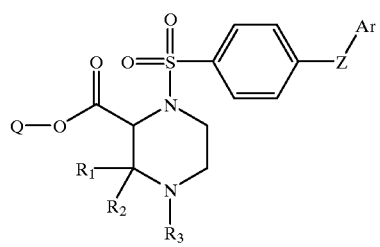

18-a: $R_1 = R_2 = R_3 = H$
18-b: $R_1$ and $R_2 = H$
   & $R_3$ is not H

Suitable protecting groups, Pg, for this type of reaction are recognizable to those skilled in the art and include, but are not limited to, t-butyl groups and benzyl groups. Removal of the protecting group by known methods provides compounds of formula 18-a where $R_3$ is hydrogen, which can be further reacted with reagents having the formula $R_3$-Lg, wherein Lg is any suitable leaving group, to give compounds of the formula 18-b where $R_3$ is not hydrogen. Illustrative examples of suitable $R_3$-Lg reagents include methanesulfonyl chloride, methyl iodide, methyl isocyanate, ethyl bromoacetate, dimethylcarbamoyl chloride, and methoxyacetic anhydride.

Compounds of formula 18 (i.e., 12-c where W is $CH_2$, Y is $CR_1R_2$, and X is $NR_3$) can be prepared as illustrated in the scheme below.

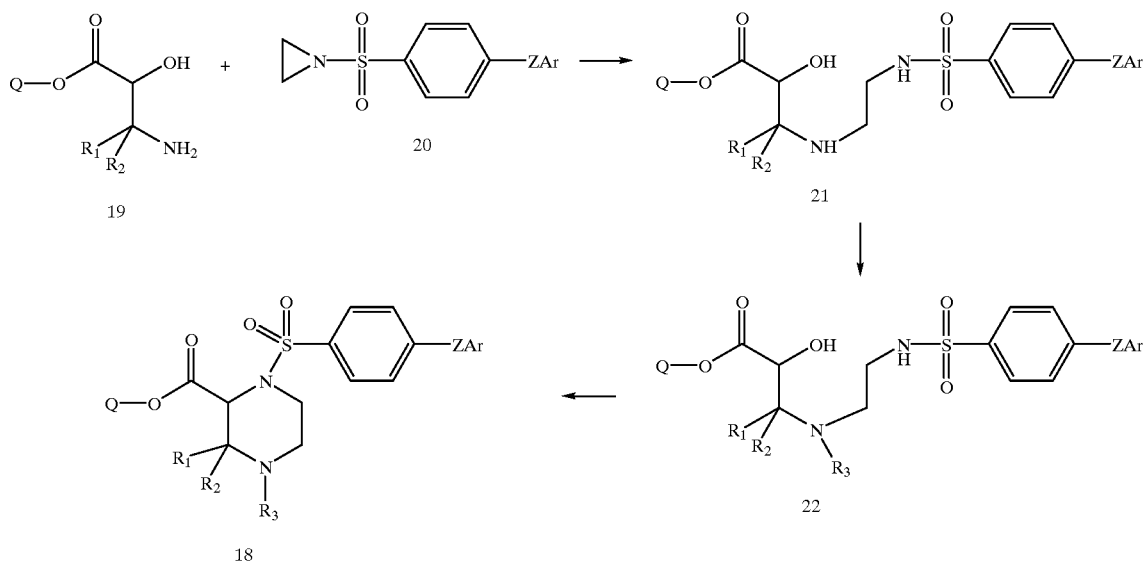

1e;2qβAmino-α-hydroxy esters of formula 19 and aziridines of formula 20 are allowed to react in inert solvent such as dichloroethane or preferably dioxane at elevated temperature, 60 to 100° C., to give adducts 21. Derivization of the amine function of 21 to provide compounds of formula 22 can be effected by conventional methods known to those skilled in the art. Cyclization of compounds of formula 22 under Mitsunobu-type conditions (see *J. Org. Chem.* 1991, 56, 3900–3905, the disclosure of which is incorporated herein by reference) provides the piperazines 18.

Compounds of formula 19 where $R_1$ is H and $R_2$ is alkyl can be prepared according to literature methods known to those skilled in the art. Where $R_1$ and $R_2$ are both methyl, the amino alcohols 19 are available from a nitronate alkylation as described in *Bull. Chem. Soc. Jpn.* 1976, 49, 3181–3184, the disclosure of which is incorporated herein by reference.

The aziridines 20 can be prepared by treatment of sulfonyl chlorides of formula 15 with excess ethanolamine in THF at −20° C. to 25° C., followed by cyclization of the resulting β-hydroxyethyl sulfonamides with DEAD and triphenylphosphine in THF. Compounds of formula 15 can be prepared as described above.

Compounds of formula 28 (i.e., 12-c where X is NH, W is C═O, and Y is $CR_1R_2$) can be prepared according to the following scheme.

Treatment of compounds of formula 23 (prepared as described in *Angew. Chem. Int. Ed. Engl.* 1994, 33, 998–999, the disclosure of which is incorporated herein by reference) with sulfonyl chlorides of formula 15, as described above, give compounds of formula 24. Alkylation of compounds of formula 24 with ethyl bromoacetate proceeds in the presence of a suitable base, such as potessium carbonate, in a suitable solvent, such as DMF, at 25° C. to 80° C. for a period of 1 to 48 hours to provide compounds of formula 25. Oxidation of alkenes 25 to compounds of formula 26 proceeds under suitable oxidizing conditions, such as excess sodium periodate in the presence of catalytic ruthenium trichloride in acetonitrile:carbon tetrachloride:water (2:2:3) solvent at 25° C. for 1 to 18 hours. Treatment of compounds of formula 26 with diphenylphosphoryl azide ("DPPA") in the presence of a suitable base, such as triethylamine, in an inert solvent, such as benzene, at 70–100° C. for 1–12 hours gives an intermediate isocyanate, which upon addition of a suitable alcohol, such as benzyl alcohol, provides compounds of formula 27, where Pg is a corresponding protecting such as benzyloxycarbonyl protecting group. Removal of the protecting group from compounds of formula 27 under conventional conditions leads to spontaneous lactamization to provide compounds of formula 28.

An alternative sequence making use of the intermediates of formula 24 is shown below.

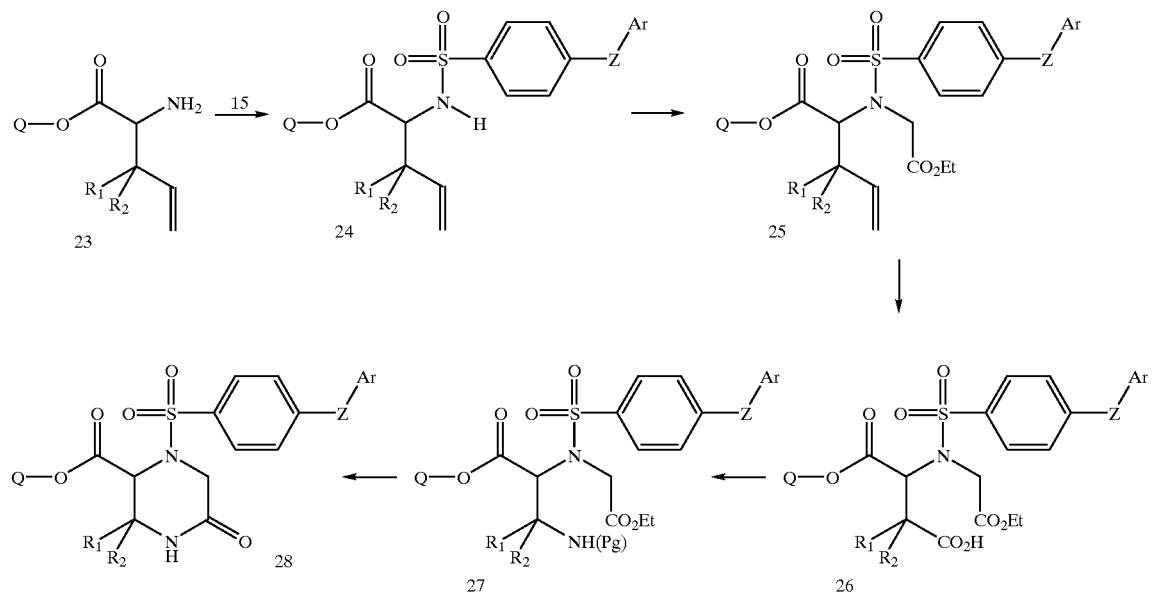

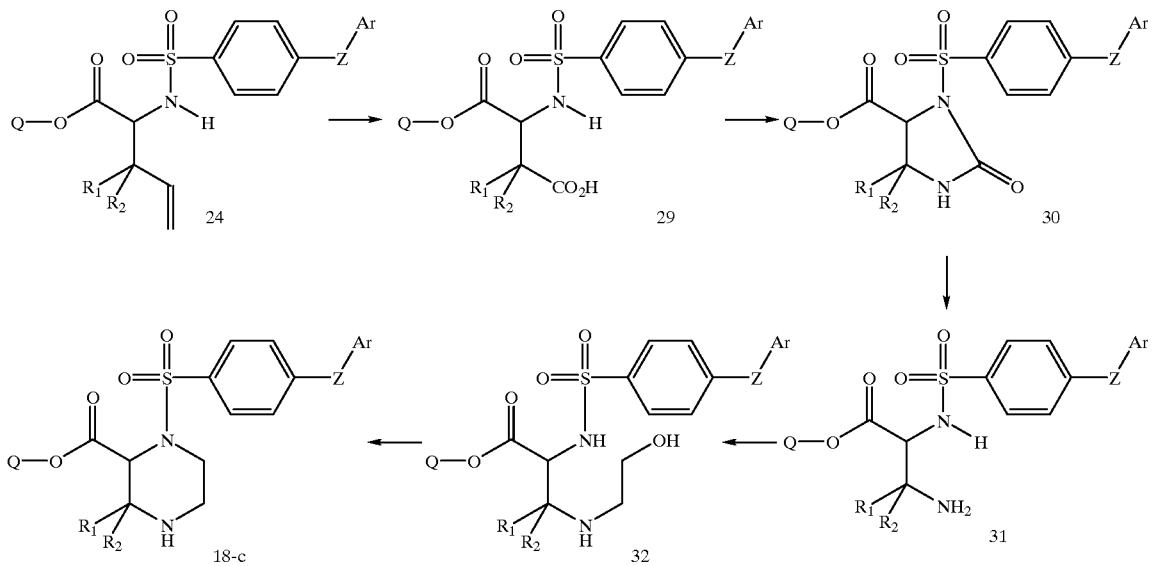

Oxidation of compounds of formula 24 under the conditions described in the preceeding paragragh for the oxidation of compounds of formula 25 gives compounds of formula 29. Curtius rearrangement of acids 29, as described for the conversion of 26 to 27 above except in the absence of added alcohol, leads to formation of compounds of formula 30. Mild basic hydrolysis of compounds of formula 30 with, for example, 1 molar equivalent of lithium hydroxide in THF-water at 0° C. for 0.5 to 18 hours leads to compounds of formula 31. Reaction of amines of formula 31 with excess ethylene oxide in alcoholic solvent at 25° C. to 75° C. for 1 to 18 hours provides compounds of formula 32, which upon treatment with DEAD and triphenylphosphine in THF at 25° C. yields compounds of formula 18-c. It will be appreciated by those skilled in the art that utilization of enantiomerically-enriched compounds of formula 24, which are accessible utilizing the methods reported in the literature and known to those skilled in the art, will yield enantiomerically-enriched compounds of formula 28 and 18-c.

Alternatively, the intermediate compounds of formula 29 can be prepared in enantiomerically-enriched form according to the following scheme.

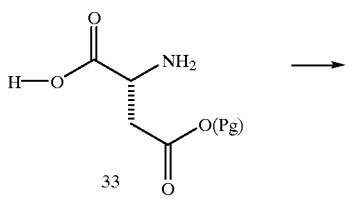

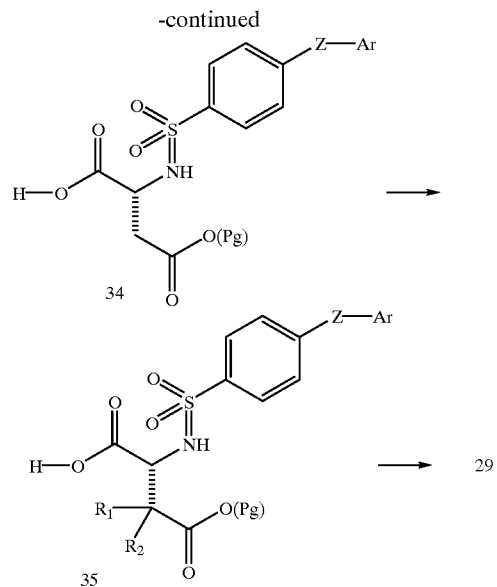

Treatment of compounds of formula 33, which are readily derived from D-aspartic acid by methods known to those skilled in the art, with trimethylsilyl chloride and triethylamine in dichloromethane at 25° C. for approximately 1 hour provides the trimethylsilyl esters, which, without isolation, are further reacted with aryl sulfonyl chlorides of the formula 15 in the presence of additional base to provide, after conventional work-up, the corresponding sulfonamides of the formula 34. Treatment of a sulfonamide 34 with approximately 3 molar equivalents of a strong base, such as lithium diisopropylamide ("LDA"), at a temperature between −78° C. and 0° C. in an inert solvent such as THF, followed with 1 equivalent of an appropriate lower alkyl halide of the formula $R_1$-X, preferably at a temperature between 0° C. and −78° C., gives a mono-alkylated product of formula 35 where $R_2$ is H. Without isolation, the reaction mixture is treated with an additional equivalent of base, and then allowed to react with a second alkyl halide of the formula $R_2$-X, where $R_1$ and $R_2$ are preferably the same, but can be different, to give, after acidic work-up, a sulfonamide of the formula 35. Following esterification of the carboxylic acid function of 35, the protecting group Pg is removed to provide the acid 29.

Alternatively, compounds of the formula 18-c can be prepared according the following scheme.

sulfonamide 36 with an α-keto ester of the formula 37 in the presence of an acid catalyst, such as p-toluenesulfonic acid, provides a compound of the formula 38. Conversion of a compound of the formula 38 to the corresponding compound of the formula 18-c is effected by cyclization in the presence of catalytic base, such as potassium carbonate, in a suitable solvent, such as DMF, followed by removal of the protecting group Pg.

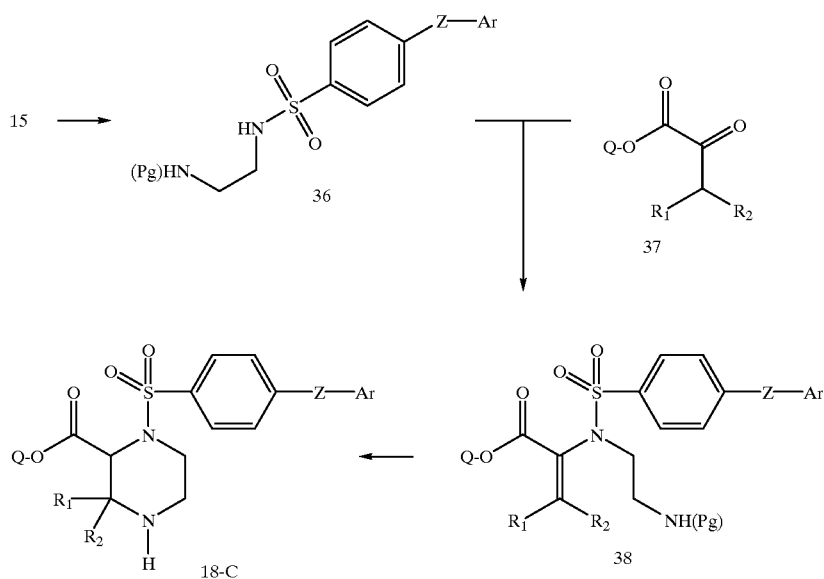

Arylsulfonyl chlorides of formula 15 can be converted to sulfonamides of formula 36 by reaction with monoprotected derivatives of ethylenediamine. Condensation of a Additionally, compounds of the formula 42 (i.e., 12-a where X is N—$R_3$, W is $CH_2$, and Y is $CR_1R_2$ can be prepared according to the following scheme.

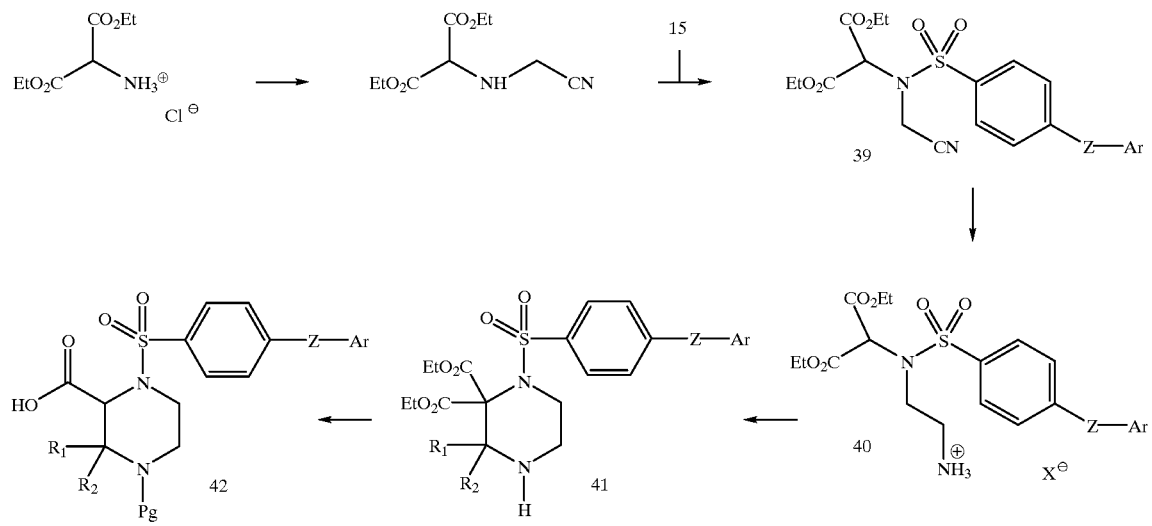

Treatment of diethyl aminomalonate, which is commerically available, with chloroacetonitrile or bromoacetonitrile in the presence of diisopropylethyl amine in ethyl alcohol provides diethyl (cyanomethyl)aminomalonate, which is further reacted with an arylsulfonyl chloride of the formula 15 to give a compound of the formula 39. Nitriles of the formula 39 are reduced to corresponding amine salts of the formula 40 by hydrogenation over a suitable metal catalyst, such as palladium or platinum, in the presence of acid in alcohol solution. Reaction of a amine salt of the formula 40 with an excess of a ketone $R_1$—CO—$R_2$ gives a piperazine derivative of the formula 41. After protection of the amine function by conventional methods known to those skilled in the art, basic hydrolysis of the ethyl esters followed by decarboxylation under acid conditions provides a compound of the formula 42.

Compounds of the formula 44 (i.e., 12-a where where W is N—H, X is C=O, and Y is CH) can be prepared according to the following scheme.

Preferably, a warm aqueous solution of D-asparagine, which is commercially available, is treated with formalin to provide, after cooling to 0° C., 6(R)-carboxy-tetrahydropyrimidin-4-one (43). Treatment of 6(R)-carboxy-tetrahydropyrimidin-4-one with trimethylsilylchloride in a suitable base, such as N-methylmorpholine or diisopropylethylamine, in a polar aprotic solvent, such as DMF, generates the corresponding trimethylsilyl ester. This ester can be treated, without isolation, with a sulfonyl chloride 15 in the presence of additional base for several hours at 25° C. to provide, after aqueous work-up, a compound of the formula 44. Alternatively, the compound of the formula 44 can be prepared directly by treating a solution of 6(R)-carboxy-tetrahydropyrimidin-4-one and a base, such as N-methyl-morpholine, in a suitable aqueous:organic mixed solvent, such as water:dioxane, with a sulfonyl chloride of the formula 15 at 25° C. for several hours followed by aqueous acid work-up.

Compounds of formula 48 (i.e., compounds of formula 12-c where W and X are $CH_2$ and Y is N—$R_3$) can be prepared according to the following scheme.

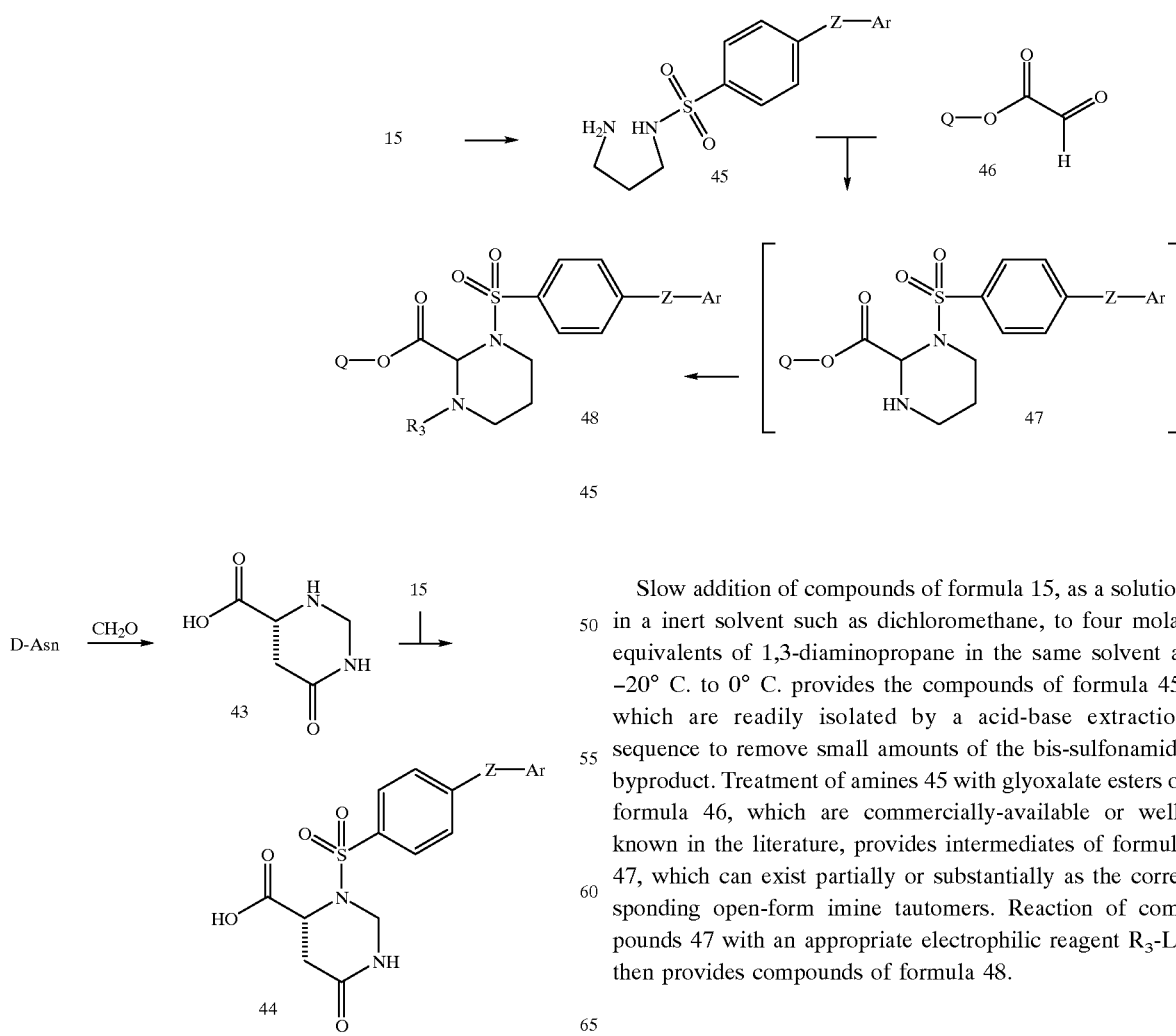

Slow addition of compounds of formula 15, as a solution in a inert solvent such as dichloromethane, to four molar equivalents of 1,3-diaminopropane in the same solvent at −20° C. to 0° C. provides the compounds of formula 45, which are readily isolated by a acid-base extraction sequence to remove small amounts of the bis-sulfonamide byproduct. Treatment of amines 45 with glyoxalate esters of formula 46, which are commercially-available or well-known in the literature, provides intermediates of formula 47, which can exist partially or substantially as the corresponding open-form imine tautomers. Reaction of compounds 47 with an appropriate electrophilic reagent $R_3$-Lg then provides compounds of formula 48.

A method for preparing compounds of formula 54, where X is O or S, is shown in the scheme below.

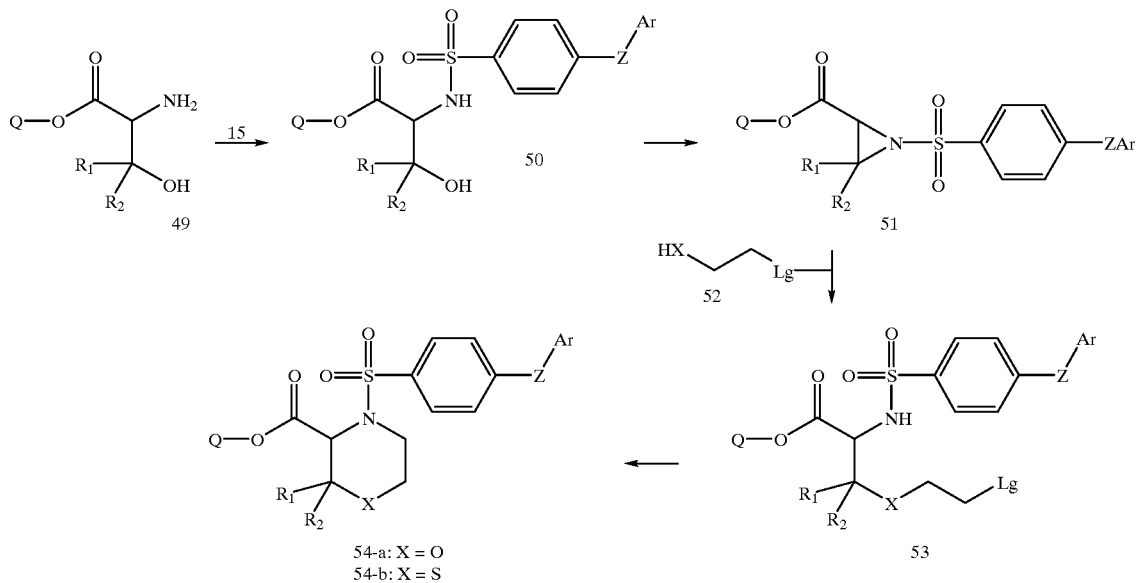

The starting β-hydroxy α-amino esters 49 are either commercially available for example serine, threonine, and allothreonine esters, or can be prepared by methods described in the literature (see, for example, *J. Org. Chem.*, 1996, 61, 2582–2583, the disclosure of which is incorporated herein by reference). Compounds of formula 49 are treated with an sulfonyl chloride having the formula 15 in the presence of a suitable tertiary amine base, such as N-methylmorpholine, in an aprotic solvent, such as DMF-dichloromethane, at 0° C. to 25° C. to provide the β-hydroxy α-sulfonylamino esters having the formula 50.

Treatment of compounds of the formula 50 with suitable dehydrating reagents, for instance triphenylphosphine and DEAD in THF solution at 25° C., provide the sulfonylaziridines of formula 51. Treatment of aziridines of formula 51 with a thiol (X=S) or alcohol (X=O) of formula 52, where Lg is any suitable leaving group (or a precursor, such as hydroxyl, to such a leaving group) in the presence of a Lewis acid, such as boron trifluoride etherate, at 0° C. to 25° C., either without additional solvent or in a suitable inert solvent such as dichloromethane, yields compounds of formula 53. Subsequent treatment of the compounds having the formula 53 with a base such as potassium carbonate in an aprotic solvent such as DMF then provides compounds of formula 54. In the case where Lg is hydroxyl, cyclization of 53 to give 54 is effected with triphenylphosphine and DEAD in THF solution at 25° C.

Alternatively, compounds of formula 54-a can be prepared from amino esters 49 by the sequence shown below.

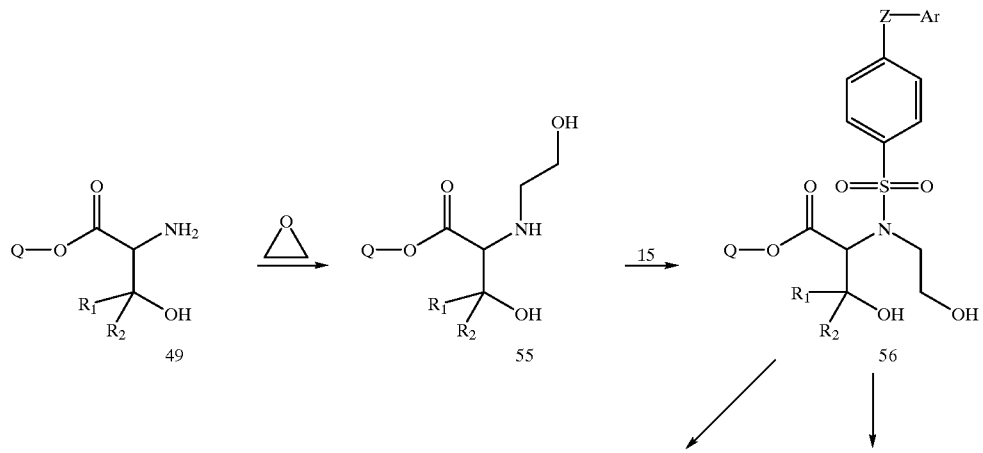

-continued

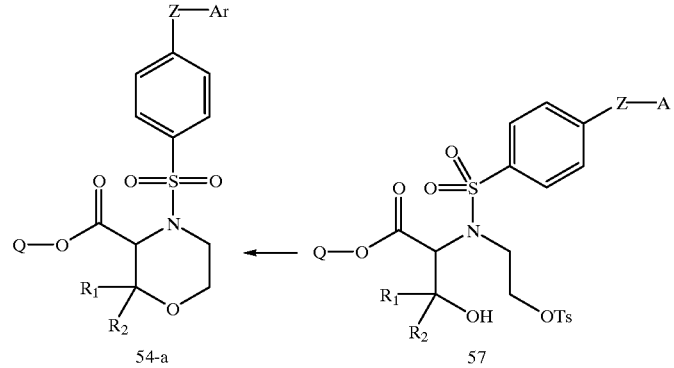

Hydroxyethylation of amino esters 49 can be effected with ethylene oxide in alcholic solvent at 25° C. to 70° C. to provide compounds of formula 55, which can be converted to compounds of formula 56 by treatment with sulfonyl chlorides 15. Diol 56 can be cyclized with the Mitsunobu protocol (see Holladay, M. W.; Nadzan, A. M. *J. Org. Chem.* 1991, 56, 3900–3905), or in traditional Williamson-style via the tosylate 57 and base to give compound of formula 54-a.

Alternatively, compounds of the formula 54-c (i.e., 54-b where Q is tert-butyl, X is S and $R_1$ and $R_2$ are both hydrogen) can be prepared according to the following scheme.

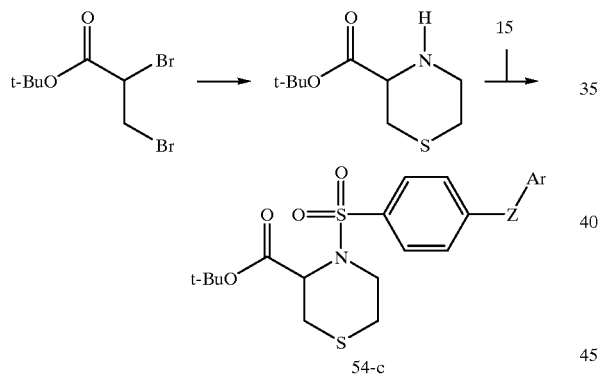

Preferably, t-butyl 2,3-dibromopropionate (prepared according to the method described in *J. Perkin Trans I*, p. 1321 (1973), the dislosure of which is incorporated herein by reference) is treated with 2-mercaptoethylamine and triethylamine in a suitable solvent, such as a mixture of chloroform and benzene, to provide t-butyl tetrahydro-1,4-thiazine-3-carboxylate, which upon reaction with a compound of the formula 15 under suitable conditions, such as in the presence of triethylamine in dichloromethane solution at 25° C., provides compounds of the formula 54-c.

As shown in the scheme below, oxidation of tetrahydrothiazines of formula 54-b to the corresponding sulfoxides of formula 54-d can be carried out under suitable oxidizing conditions, such as m-chloroperbenzoic acid in dichloromethane at −78° C. to 0° C. or sodium perborate in acetic acid at 25° C. to 50° C. It is to be understood that such oxidations can also be carried out at other intermediate stages in the synthesis of compounds of formula 1-a where X is S=O, and also to directly convert compounds of formula 1-a where X is S to compounds of formula 1-a where X is S=O.

Compounds of the formula 54-b can be prepared according to

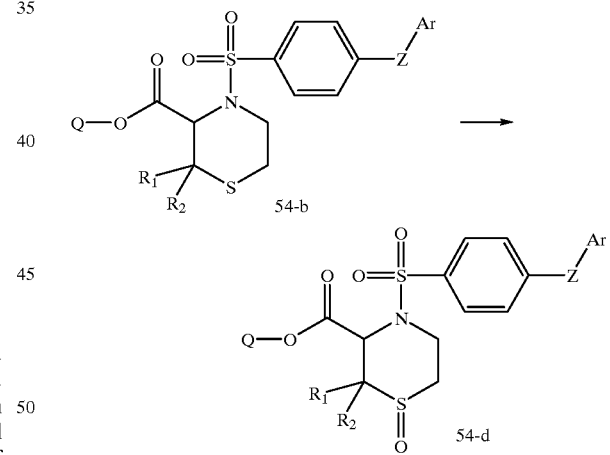

the following scheme.

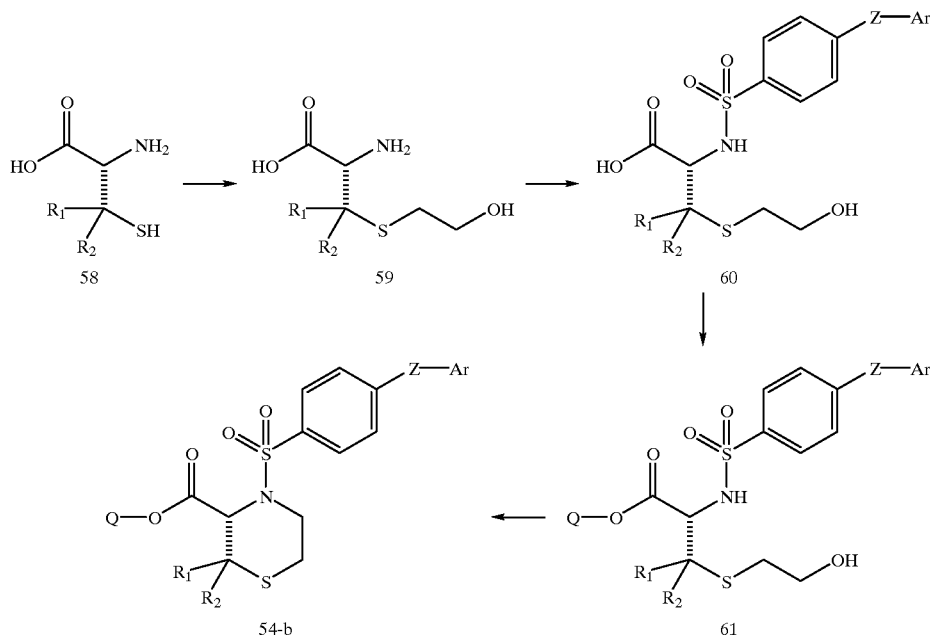

First, β-mercapto-α-amino acids of formula 58, such as D-penicillamine or D-cysteine, both of which are commercially available, are treated with 2-bromoethanol in the presence of a base, such as sodium hydroxide, to provide 2-hydroxyethyl sulfides of formula 59. Intermediates of formula 59 are then reacted directly with compounds of the formula 15 in the presence of a suitable base, such as sodium carbonate, in an appropriate solvent system, such as DMF/water to provide the N-sulfonyl derivatives 60. The acid function of compounds of formula 60 is then protected as a suitable ester group Q, for example, the t-butyl ester which is prepared by reaction of 60 with t-butyl bromide in the presence of a suitable base, such as potassium carbonate, and a suitable catalyst, such as benzyltriethylammonium chloride ("BTEAC") in dimethylacetamide at a temperature between 50° C. and 60° C. Cyclization of the compound of the formula 61 can be effected using triphenylphosphine and DEAD in a suitable solvent, such as THF, to yield a compound of the formula 54-b.

More preferably, compounds of the formula 1-d (e.g., 1-a where W is $CH_2$, X is S, and Y is $CR_1R_2$) can be prepared according to the following scheme.

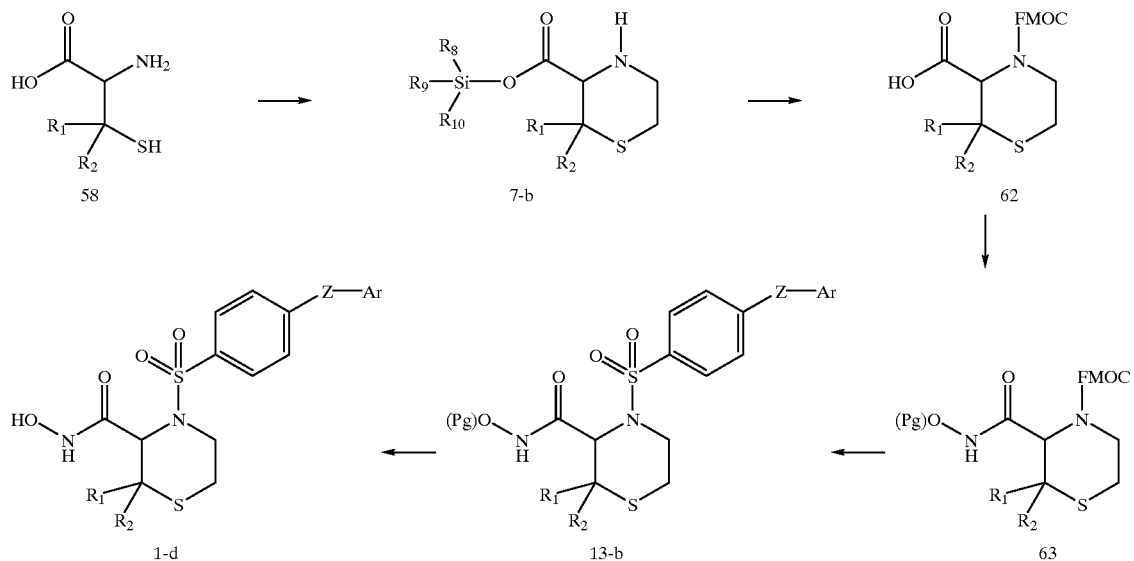

Treatment of compounds of formula 58 with a trialkylsilyl chloride, such as trimethylsilyl chloride, in the presence of a tertiary amine base, such as diisopropylethylamine, in an aprotic solvent, such as DMF, provides the corresponding trialkylsilyl ester, which upon reaction with 1,2-dichloroethane or 1,2-dibromoethane in the presence of DBU at 25° C. gives the intermediate tetrahydrothiazine of the formula 7-b. Without isolation, this intermediate is further reacted with 9-fluorenylmethyl chloroformate ("FMOC-Cl") in the presence of additional base, such as N-methyl morpholine, to provide, after aqueous acidic workup, the free carboxylic acid of the formula 62. This acid can then be coupled to an O-protected hydroxylamine, for example where Pg is t-butyldiphenylsilyl, with conventional peptide coupling reagents, such as EDC, to give the protected hydroxamate of the formula 63. Removal of the FMOC protecting group with conventional methods, such as piperidine in DMF, followed by reaction with a sulfonyl chloride of the formula 15 in the presence of base, such as N-methyl morpholine, in a suitable solvent, such as dichloromethane, provides compounds of the formula 13-b. Removal of the protecting group Pg affords compounds of the formula 1-d.

Particularly preferred compounds of this invention are compounds of formula 10. The preparation of compounds of formula 64-b described above can be applied to the synthesis of compounds of formula 10. More preferably, however, compounds of the formula 10 are prepared according to the process described below.

SUMMARY OF THE PROCESS

One aspect of the present invention is a process for the synthesis of certain matrix metalloprotease inhibitors, represented by the formula 10.

The reaction scheme can be summarized as involving the following steps:

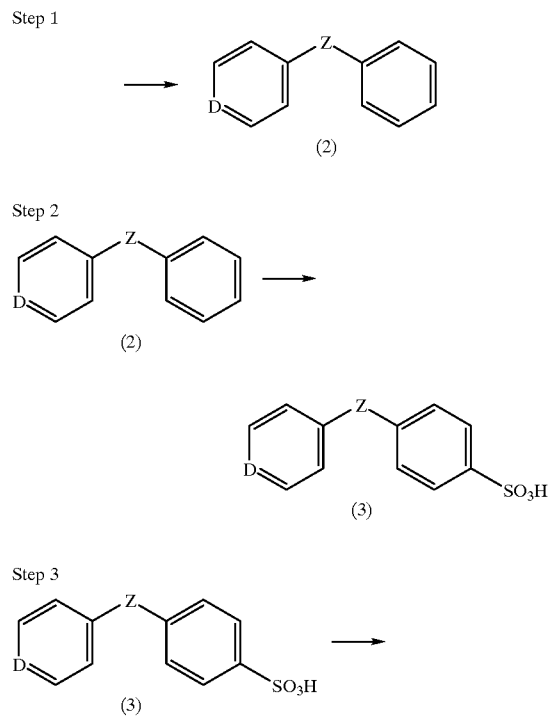

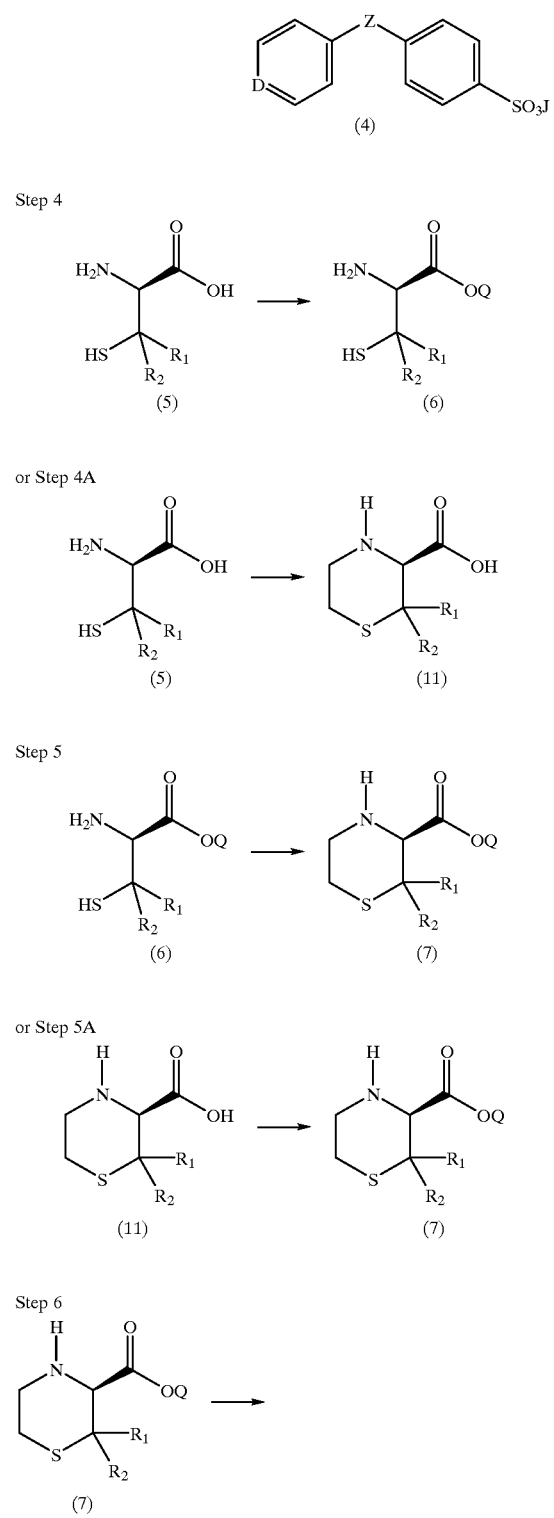

41

-continued

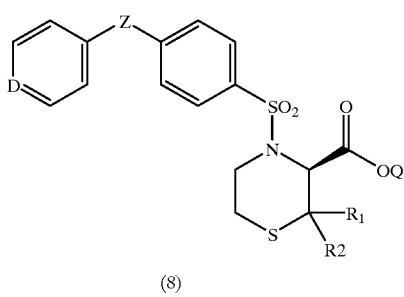

(8)

Step 7

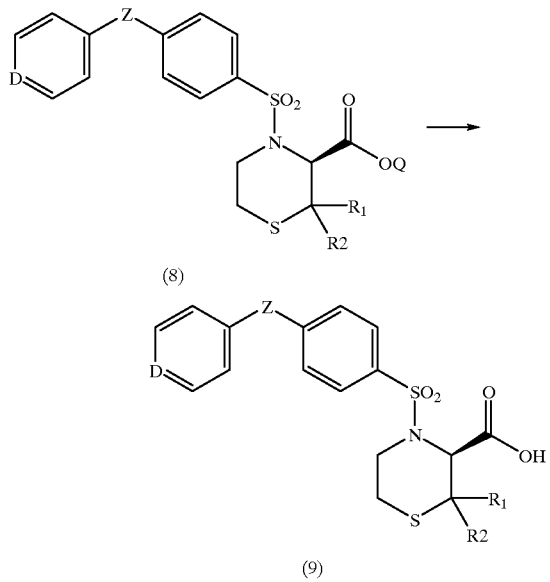

Step 8

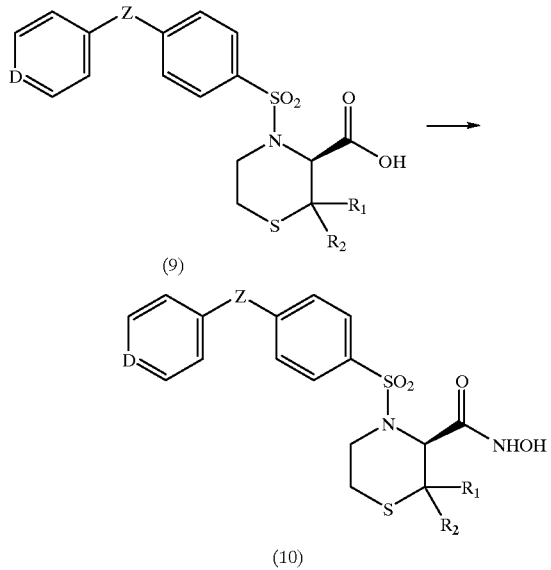

The process comprises combining a suitably activated two-carbon piece with the amino acid 5 to form a tetrahydro-2H-1,4-thiazine derivative 11 or with a suitable ester 6 to form a tetrahydro-2H-1,4-thiazine derivative 7. A compound of formula 7 is treated with an activated sulfonic acid derivative 4 to give the corresponding sulfonamide 8. The ester functionality Q in compound 8 is deprotected to give compound 9, which is then activated by formation of an acid chloride or other suitable activating group. The activating group is displaced by hydroxylamine or a suitable salt or derivative of hydroxylamine to give the hydroxamic acid 10. The activated diarylether sulfonic acid derivative 4 can be prepared from the diaryl ether 2 by chlorosulfonation directly to the sulfonyl chloride or by a stepwise process of sulfonation to the sulfonic acid 3, followed by conversion to the sulfonyl chloride or other suitably activated sulfonic acid derivative.

DETAILED DESCRIPTION OF THE PROCESS

A number of diarylethers 2 are commercially available. In cases where the diarylether is not commercially available, the first step of the process involves preparing the diarylether 2. In the case where D is nitrogen, compounds 2 can be made by combining either 4-chloropyridine hydrochloride or 1-(4-pyridyl)pyridinium chloride hydrochloride with phenol or thiophenol at or above 100° C. either neat or in water, toluene, xylenes, or other suitable solvent.

In Step 2 of the process, the diaryl ether is treated with chlorosulfonic acid, sulfuric acid, sulfur trioxide, or other suitable sulfonating agent to give the sulfonic acid 3, which is used directly or isolated by water quench followed by solvent removal or extraction into a suitable water immiscible organic solvent. In some cases, a quaternary ammonium salt such as tetrabutylammonium bromide can be used to increase the solubility of the sulfonic acid 3 in organic solvents.

Step 3 of the process involves adding thionyl chloride, oxalyl chloride, chlorosulfonic acid, phosphorus pentachloride, or another suitable chlorinating reagent to the sulfonic acid 3 in acetonitrile, dichloromethane, 1,2-dichloroethane, or another suitable organic solvent. The resulting sulfonyl chloride 4 can be isolated by solvent removal or water quench followed by filtration or extraction. Alternatively, the sulfonic acid 3 can be converted to the sulfonyl fluoride with fluorosulfonic acid or sulfonyl bromide with thionyl bromide. If desired, the sulfonyl chloride, sulfonyl fluoride, and sulfonyl bromide compounds can be converted to the more stable triazolide or benzotriazolide derivatives by treatment with 1,2,4-triazole or benzotriazole respectively.

In Step 4, compound 5 is converted to a suitable silyl or carbon ester. In the cases where a silyl ester is utilized, trimethylsilyl chloride, tert-butyldimethylsilyl chloride, dimethylthexylsilyl chloride, triisopropylsilyl chloride, or another suitable silylating reagent is added to a mixture of compound 5 and 1,8-diazabicyclo[5.4.0]undec-7-ene, triethylamine, diisopropylethylamine, 4-methylmorpholine, pyridine, or other suitable tertiary amine base in N,N-dimethylformamide, acetonitrile, dichloroethane, or other suitable aprotic solvent. The resulting mixture of the silyl ester 6 can be used directly in Step 5, or the silyl ester can be isolated by aqueous work-up, extraction, and solvent removal.

In the cases where a carbon ester is utilized, a mixture of compound 5 and sulfuric acid, hydrogen chloride, p-toluenesulfonic acid, or another suitable organic or mineral acid in methanol, ethanol, isopropanol, 1-butanol, tert-butanol, allyl alcohol, or other suitable alcohol solvent is heated at reflux for 4 to 60 hours. The resulting ester is isolated as either the free base or amine salt by solvent removal and/or aqueous work-up, followed by extraction with an appropriate solvent and finally solvent removal or salt formation by addition of an appropriate acid.

Alternatively, the tert-butyl ester can be prepared by maintaining a mixture of compound 5 in liquid isobutylene, a suitable organic solvent such as 1,4-dioxane, and a suitable mineral acid or organic acid such as sulfuric acid, hydrogen chloride, or p-toluenesulfonic acid at reflux for 4 to 60 hours.

In Step 4A, compound 5 is mixed with 1,8-diazabicyclo[5.4.0]undec-7-ene, sodium hydroxide, potassium hydroxide, or other suitable organic or inorganic base, and 1,2-dichloroethane, 1,2-dibromoethane, or other suitable activitated two carbon moiety in 1,2-dichloroethane, N,N-dimethylformamide, methanol, ethyl acetate, tetrahydrofuran, acetonitrile, water or other appropriate solvent. The resulting tetrahydro-2H-1,4-thiazine derivative 11 is isolated by precipitation, followed by filtration or by solvent removal. Alternatively, the carboxylic acid functionality of compound 5 can be protected in-situ by addition of trimethylsilyl chloride and 1,8-diazabicyclo[5.4.0]undec-7-ene. The resulting silyl ester is treated with 1,2-dichloroethane, 1,2-dibromoethane, or another suitable activated two carbon moiety and 1,8-diazabicyclo[5.4.0]undec-7-ene or another suitable tertiary amine base in 1,2-dichloroethane, N,N-dimethylformamide, or other suitable aprotic solvent. The silyl ester is deprotected in-situ by addition of methanol, 2-propanol, or another alcoholic solvent and the resulting tetrahydro-2H-1,4-thiazine derivative 11 is isolated by precipitation and filtration.

In Step 5, the ester 6 is treated with 1,8-diazabicyclo[5.4.0]undec-7-ene, sodium hydroxide, potassium hydroxide, or other suitable organic or inorganic base, and 1,2-dichloroethane, 1,2-dibromoethane, or other suitable activitated two carbon moiety in 1,2-dichloroethane, N,N-dimethylformamide, methanol, ethyl acetate, tetrahydrofuran, acetonitrile, or other appropriate solvent. The resulting tetrahydro-2H-1,4-thiazine derivative 7 is isolated by precipitation or aqueous work-up followed by extraction with an organic solvent and solvent removal.

In Step 5A, compound 11 is converted to a suitable silyl or carbon ester. In the cases where a silyl ester is utilized, trimethylsilyl chloride, tert-butyldimethylsilyl chloride, dimethylthexylsilyl chloride, triisopropylsilyl chloride, or another suitable silylating reagent is added to a mixture of compound 11 and 1,8-diazabicyclo[5.4.0]undec-7-ene, triethylamine, diisopropylethylamine, 4-methylmorpholine, pyridine, or other suitable tertiary amine base in N,N-dimethylformamide, acetonitrile, dichloroethane, or other suitable aprotic solvent. The resulting mixture of the silyl ester 7 can be used directly in Step 6, or the silyl ester can be isolated by aqueous work-up, extraction, and solvent removal.

In the cases where a carbon ester is utilized, a mixture of compound 11 and sulfuric acid, hydrogen chloride, p-toluenesulfonic acid, or another suitable organic or mineral acid in methanol, ethanol, isopropanol, 1-butanol, tert-butanol, allyl alcohol, or other suitable alcohol solvent is heated at reflux. The resulting ester is isolated as either the free base or amine salt by solvent removal and/or aqueous work-up, followed by extraction with an appropriate solvent, and finally solvent removal or salt formation by addition of an appropriate acid. Alternatively, the tert-butyl ester can be prepared by maintaining a mixture of compound 11 in 1,4-dioxane or other suitable solvent, liquid isobutylene, and sulfuric acid, hydrogen chloride, p-toluenesulfonic acid, or another suitable mineral acid or organic acid at reflux.

Alternatively, the tetrahydro-2H-1,4-thiazine derivative 11 can be left unprotected and used directly in Step 6. In this case, Step 5A is simply omitted.

In Step 6, the tetrahydro-2H-1,4-thiazine derivative 7 or 11 and the activated diarylether sulfonic acid derivative 4 are combined in dichloromethane, 1,2-dichloroethane, acetonitrile, N,N-dimethylformamide, ethyl acetate, toluene, tert-butyl methyl ether, or another suitable solvent in the presence of 4-methylmorpholine, pyridine, triethylamine, diisopropylethylamine, potassium carbonate, or another suitable organic tertiary amine base or inorganic base. The resulting sulfonamide derivative 8 is isolated by aqueous work-up, extraction into an appropriate organic solvent, and solvent removal.

Step 7 involves the deprotection of the ester protecting group of compound 8 to give carboxylic acid 9. In the cases where a silyl ester is utilized, deprotection is accomplished by maintaining a mixture of the ester and methanol, ethanol, isopropanol, or another alcohol solvent at 20° C. to reflux and isolating the product by filtration or solvent removal. Alternatively, silyl esters can be deprotected by treatment with mineral acid or acetic acid in either organic or aqueous solution or by treatment with fluoride ion in organic solution.

In the cases where a carbon ester is utilized, the ester can by removed by heating a mixture of compound 8 and hydrogen chloride, sulfuric acid, or other mineral in water, dioxane or another suitable organic solvent at reflux. Alternatively, the ester can be removed by treatment with sodium hydroxide, lithium hydroxide, potassium hydroxide, or another suitable inorganic base in water or a combination of water and methanol, tetrahydrofuran, or another suitable organic solvent. In the case where Q is allyl, the ester can be removed by treatment with N-methylaniline, morpholine, or another suitable secondary amine and tetrakis(triphenylphosphine)palladium(0) or another suitable palladium(0) catalyst in ethyl acetate, acetonitrile, or another suitable organic solvent. In the case where Q is benzyl, the ester can be removed by catalytic hydrogenation.

The final step of the process is a two-step procedure involving in-situ activation of the carboxyl functionality of compound 9 and subsequent displacement with hydroxylamine or a suitable salt or derivative of hydroxylamine. The activation is accomplished by reaction of compound 9 with oxalyl chloride or thionyl chloride with or without N,N-dimethylformamide present as catalyst in dichloromethane, acetonitrile, or other suitable solvent to give the corresponding acid chloride. Alternatively, the carboxyl can be activated by addition of methanesulfonyl chloride, isobutylchloroformate or various other chloroformate reagents, 1,3-dicyclohexylcarbodiimide or other carbodiimide reagents. The activated compound is added to hydroxylamine or a suitable salt or derivative of hydroxylamine and an appropriate organic or inorganic base, if necessary, in water, tetrahydrofuran, dioxane, dimethoxyethane, tert-butyl alcohol, dichloromethane, or other suitable solvent or solvent combinations. The resulting hydroxamic acid 10 can be isolated by solvent removal or by dissolution in aqueous hydroxide, adjusting the pH to 5 to 10 range, and collecting the precipitate by filtration.

A preferred compound is 3(S)-N-hydroxy-4-(4-((pyrid-4-yl)oxy)benzenesulfonyl)-2,2-dimethyl-tetrahydro-2H-1,4-thiazine-3-carboxamide, illustrated by the structural formula:

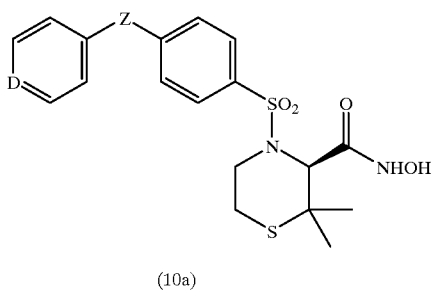

(10a)

A preferred carboxylic acid protecting group, Q, is dimethylthexylsilyl, where A is silicon, $R_8$ and $R_9$ are both $CH_3$, and $R_{10}$ is $(CH_3)_2CHC(CH_3)_2$, illustrated by the following structural formula:

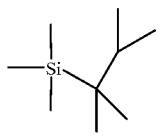

Other compounds of the formula 1 may be prepared by methods known to those skilled in the art in a manner analagous to the general procedures described above. Specific examples of methods used to prepare the inventive compounds are described below along with illustrative preferred embodiments of the inventive compounds of the formula 1, 1-a, 1-f or 1-g, or their pharmaceutically acceptable prodrugs, salts or solvates.

The following specific examples are intended to be illustrative of the invention and should not be construed as limiting the scope of the invention as defined by the appended claims. These examples include preferred embodiments of the inventive compounds.

EXAMPLE 1

Process for the preparation of 3(S)-N-hydroxy-4-(4-((pyrid-4-yl)oxy)benzenesulfonyl)-2,2-dimethyl-tetrahydro-2H-1,4-thiazine-3-carboxamide 1(a) Via the intermediate 3(S)-dimethylthexylsilyl 2,2-dimethyl-tetrahydro-2H-1,4-thiazine-3-carboxylate Step 1. Preparation of 4-Phenoxypyridine Phenol (2.82 kg, 30.0 mol) was heated to 50° C. and 4-chloropyridine hydrochloride (1.5 kg, 10.0 mol) was added. The resulting solution was heated at 150° C. for 15 hours. The dark amber solution was cooled to 25° C. then poured into 3 M aqueous sodium hydroxide (16 L). The aqueous was extracted with dichloromethane (3×4 L). The combined organic was washed with 1 M sodium hydroxide (2×4 L), water (4 L), and brine (4 L) then dried over sodium sulfate and filtered. The solvent was removed under vacuum and the residual oil was dissolved in hexanes (6 L). The mixture was cooled to −60° C. with stirring and the resulting solid was collected by filtration and dried to give 1.1 kg of 4-phenoxypyridine (64% yield). mp 46–49° C. $^1$H NMR (300 MHz, CDCl3) δ8.45 (dd, J=1.5, 8 Hz, 2H), 7.41 (dd, J=12, 12 Hz, 2H), 7.28 (dd, J=12, 1H), 7.06 (d, J=12 Hz, 2H), 6.84 (dd, J=1.5, 8 Hz, 2H).

Step 2. Preparation of 4-[(Pyrid-4-yl)oxy]benzenesulfonic acid 3a

To a vigorously stirred solution of 4-phenoxypyridine (1 kg) in dry 1,2-dichloroethane (3 L) at −10° C. under a stream of argon, chlorosulfonic acid (974 mL) was added slowly. The addition rate of the chlorosulfonic acid was adjusted to keep the reaction temperature below 0° C. After half of the chlorosulfonic acid was added, the exotherm stopped. The cooling bath was removed and the addition of chlorosulfonic acid continued over 3 hours while the reaction solution warmed to room temperature. While continually purging with inert gas, the vigorously stirred reaction mixture was heated to 45° C. By thin layer chromatography analysis, no more starting material remained after 20 hours.

The reaction mixture was cooled to room temperature and slowly poured into ice cold water (5 L) while stirring. Potassium phosphate tribasic (212 g) was added as a solid to the mixture and this was stirred for 10 minutes followed by addition of sodium hydroxide (2M) to pH 2. After stirring for 1 hour, the pH was changed to 7 by the addition of sodium hydroxide (2M). Agitation was continued for 5 minutes then the organic layer was drained off and discarded. The mixture was extracted a second time with dichloromethane (2L), the mixture agitated for 5 minutes, and the organic layer drained off and discarded. The remaining aqueous mixture was extracted by addition of dichloromethane (6 L), tetrabutylammonium bromide (940 g), and sodium hydroxide (2M) to pH 7. The mixture was agitated for 5 minutes and the organic layer (bottom) drained into a flask. The extraction procedure was repeated twice. The combined organic was dried over magnesium sulfate, filtered, and the solution was concentrated under vacuum to an oil. The residual oil was diluted with 20% ethanol in ethyl acetate (8 L, dry), and hydrogen chloride gas added to a pH of 1. The solid was filtered off and the filter cake rinsed with 20% ethanol in ethyl acetate (2L). The solid was dried under vacuum at 45° C. for 15 hours to yield 4-[(pyrid-4-yl)oxy]benzenesulfonic acid 3a (1.3 kg) as a white powdery solid.
mp dec. >275° C.

Anal. calc. for $C_{11}H_9NO_4S$: C, 52.58; H, 3.61; N, 5.57; S, 12.76. Found: C, 52.50; H, 3.69; N, 5.51; S, 12.67.

1H NMR (300 MHz, DMSO-d6): δ8.86 (dd, J=1.5, 7.4 Hz, 2H), 7.84 (dd, J=1.5, 7 Hz, 2H)7.54 (dd, J=1.5, 7.4 Hz, 2H), 7.35 (dd, J=1.5, 7 Hz, 2H).

Step 3. Preparation of 4-[(pyrid-4-yl)oxy]benzenesulfonyl chloride hydrochloride 4a To a suspension of 4-[(pyrid-4-yl)oxy]benzenesulfonic acid 3a (1.3 kg) in acetonitrile (8 L), was added N,N-dimethylformamide (12.35 mL) and the viscous reaction mixture was heated to 75° C. Thionyl chloride (756 mL) was added to the reaction mixture over 30 minutes. The reaction mixture slowly became less viscous and became homogeneous after 45 minutes, which indicated the reaction was complete. A portion of the solvent (4 L) was evaporated under vacuum and tert-butyl methyl ether (4 L) was added. The resulting slurry was filtered under inert atmosphere. The filter cake was rinsed with tert-butyl methyl ether (2 L) and the solid dried under vacuum to yield 4-[(pyrid-4-yl)oxy]benzenesulfonyl chloride hydrochloride 4a (1.35 kg) as a fluffy off-white solid of pearlescent flakes: mp 182° C.; $^1$H NMR (300 MHz, CDCl13): δ8.87 (d, J=7 Hz, 2H), 8.24 (d, J=8.5 Hz, 2H), 7.50 (d, J=8.5 Hz, 2H), 7.43 (d, J=7 Hz, 2H).

Steps 4 and 5. Preparation of 3(S)-dimethylthexylsilyl 2,2-dimethyl-tetrahydro-2H-1,4-thiazine-3-carboxylate Under argon atmosphere, D-penicillamine (375 g, 2.51 mol) was suspended in dry N,N-dimethylformamide (3.8 L)

and 1,8-diazabicyclo [5.4.0]undec-7-ene (413 mL, 2.76 mol) was added, forming a clear solution. While the temperature was kept between 20–30° C., dimethylthexylsilyl chloride (543 mL, 2.76 mol) was added dropwise. After stirring for 1.5 hours, 1,2-dichloroethane (593 mL, 7.53 mol) was added in one portion. 1,8-diazabicyclo [5.4.0]undec-7-ene (788 mL, 5.27 mol) was added over 1 hour, keeping the temperature between 25–30° C. The resulting mixture was stirred at 20° C. for 3 hours then quenched into a 0C mixture of water (8 L), tert-butyl methyl ether (2 L), and hexanes (2 L). After stirring 5 minutes, the phases were separated and the aqueous was extracted with additional tert-butyl methyl ether (2 L) and hexanes (2 L) mixture. The combined organic layers were dried over magnesium sulfate, filtered, and the solvent removed under vacuum to give 878 g (110% yield) of crude 3(S)-dimethylthexylsilyl 2,2-dimethyl-tetrahydro-2H-1,4-thiazine-3-carboxylate as a thick, yellow oil. $^1$H NMR (300 MHz, CDCl$_3$) δ3.65 (s, 1H), 3.42–3.37 (m, 1H), 2.98–2.83 (m, 2H), 2.30–2.22 (m, 1H), 1.69–1.58 (m, 1H), 1.42 (s, 3H), 1.31 (s, 3H), 0.92–0.86 (m, 12H), 0.34 (s, 3H), 0.30 (s, 3H).

Steps 6 and 7. Preparation of 3(S)-4-(4-((pyrid-4-yl)oxy)benzenesulfonyl)-2,2-dimethyl-tetrahydro-2H-1,4-thiazine-3-carboxy acid Crude 3(S)-dimethylthexylsilyl 2,2-dimethyl-tetrahydro-2H-1,4-thiazine-3-carboxylate (878 g, 2.51 mol) and 4-methylmorpholine (547 mL, 4.98 mol) were dissolved in dry dichloromethane (14 L) and the solution cooled to −20° C. 4-[(pyrid-4-yl)oxy]benzenesulfonyl chloride hydrochloride 4a (690 g, 2.26 mol) was added and the mixture was warmed slowly to 20° C. and maintained at 20° C. for 12 hours. The resulting red suspension was poured into water (8 L). The phases were separated and the organic layer dried over sodium sulfate, filtered, and the solvent removed under vacuum, giving 1.4 kg (117% yield) of 3(S)-dimethylthexylsilyl 4-(4-((pyrid-4-yl)oxy) benzenesulfonyl)-2,2-dimethyl-tetrahydro-2H-1,4-thiazine-3-carboxylate as a red oil which was used without purification or characterization.

The residual red oil was dissolved in methanol (14 L) and the solution was heated at reflux for 1 hour, forming a precipitate. The mixture was cooled to 4° C. and the precipitate was collected by filtration, washed with methanol, and dried to give 575 g (62% yield) of 3(S)-4-(4-((pyrid-4-yl)oxy)benzenesulfonyl)-2,2-dimethyl-tetrahydro-2H-1,4-thiazine-3-carboxylic acid as a light pink solid: mp dec. >235° C.; $^1$H NMR (300 MHz, CDCl3): δ8.60 (dd, J=1.5, 5 Hz, 2H), 7.86 (d, J=8.5, 2H), 7.39 (d, J=9 Hz, 2H), 7.11 (dd, J=1.5, 5 Hz, 2H), 4.3 (s, 1H), 4.03 (d, J=12.5 Hz, 1H), 3.75 (ddd, J=2.2, 13, 13 Hz, 1H), 3.02 (ddd, J=3, 12.5, 13 Hz, 1H), 2.62 (d, J=14 Hz, 1H), 1.52 (s, 3H), 1.35 (s, 3H).

Step 8. Preparation of 3(S)-N-hydroxy-4-(4-((pyrid-4-yl)oxy)benzenesulfonyl)-2,2-dimethyl-tetrahydro-2H-1,4-thiazine-3-carboxamide A suspension of 3(S)-4-(4-((pyrid-4-yl)oxy) benzenesulfonyl)-2,2-dimethyl-tetrahydro-2H-1,4-thiazine-3-carboxylic acid (700 g, 1.71 mol) in dichloromethane (7 L) was cooled to −65° C. Oxalyl chloride (179 mL, 2.05 mol) was added rapidly. The cooling bath was removed and the mixture was stirred at 20° C. for 15 hours. The resulting solution was added over 1.25 hours to a solution of hydroxylamine (1.05 L of 50% aqueous solution, 17.15 mol) in tetrahydrofuran (3.5 L) and tert-butyl alcohol (1.8 L), keeping the temperature between 5 and 20° C. The resulting mixture was stirred at 20° C. for 15 hours then poured into 1 M aqueous sodium hydroxide (10 L) at 5° C. The phases were separated and the aqueous was extracted with tert-butyl methyl ether (4 L). The aqueous layer was filtered through Celite and the pH adjusted to 8.5 by adding saturated aqueous ammonium chloride and concentrated hydrochloric acid. The resulting suspension was stirred for 3 hours. The solid was collected by filtration, washed with water, and dried to give 665 g (92% yield) of crude product. The crude material was recrystallized from a mixture of ethanol, water, and dichloromethane to give 466 g (70% recovery) of 3(S)-N-hydroxy-4-(4-((pyrid-4-yl)oxy)benzenesulfonyl)-2,2-dimethyl-tetrahydro-2H-1,4-thiazine-3-carboxamide as a white, crystalline solid: mp 184–186° C. with gas evolution; $^1$H NMR (300 MHz, DMSO-d6): δ10.69 (d, J=1.5 Hz, 1H), 8.93 (d, J=1.5 Hz, 1H), 8.57 (dd, J=1.5, 4.5 Hz, 2H), 7.83 (dd, J=2, 7 Hz, 2H), 7.37 (dd, J=2, 7 Hz,2H), 7.11 (dd, J=1.5, 4.5 Hz, 2H), 4.06 (s, 1H), 4.07 (ddd, J=2.5, 12.5, 12.5 Hz, 1H), 3.91 (ddd, J=3, 2.2, 12 Hz, 1H), 2.98 (ddd, J=3.7, 13, 13.5 Hz, 1H), 2.7–2.55 (m,1H), 1.49 (s, 3H), 1.22 (s, 3H).

EXAMPLE 1(b)

Via t-Butyl 3(S)-2,2-dimethyl-tetrahydro-2H-1,4-thiazine-3-carboxylate

Step 4A. 3(S)-2,2-Dimethyl-tetrahydro-2H-1,4-thiazine-3-carboxylic acid 11

To a stirred suspension of D-penicillamine (14.92 g), in 1,2-dichloroethane (300 mL) and N,N-dimethylformamide (2 mL) at 0° C. was added 1,8-diazabicyclo[5.4.0]undec-7-ene (22.4 mL), followed by trimethylsilyl chloride (19.0 mL). The reaction mixture was stirred for 3 hours, slowly warming to room temperature. To the homogeneous solution 1,8-diazabicyclo[5.4.0]undec-7-ene (29.9 mL) was added over 10 minutes and the reaction warmed to 47° C. The reaction mixture was cooled to room temperature and was stirred an additional 17.5 hours. Methanol (10 mL) was added to the reaction mixture and a precipitate formed after stirring for 10 minutes. The reaction mixture was filtered and the precipitated material rinsed with a minimum amount of methanol. The solid was dried under vacuum at 50° C. for 6 hours to yield 3(S)-2,2-dimethyl-tetrahydro-2H-1,4-thiazine-3-carboxylic acid (16.18 g) as a white powdery solid: mp dec.>212° C.; $^1$H NMR (300 MHz, D20): δ3.71(s, 1H), 3.68–3.60 (m, 1H), 3.27–3.01 (m, 2H), 2.78–2.64 (m, 1H), 1.45 (s, 3H), 1.42 (s, 3H).

Step 4a was also performed as follows:

To a stirred suspension of D-penicillamine (14.92 g), in 1,2-dichloroethane (150 mL) and dimethyl formamide (15 mL) at room temperature, was added trimethyl silyl chloride (19.0 mL) over 30 minutes and the reaction warmed to 43° C. To the resulting vixcous suspension 1,8-diazabicyclo [5.4.0.]undec-7-ene (22.4 mL) was added at a constant rate over 4 hours, and during the addition the reaction warmed to 48° C. The reaction mixutre slowly cooled to room temperature and was stirred an additional 2 hours. Isopropanol (75 mL) was added to the reaction mixture and this mixture was stirred for 3 hours while a precipitate formed. The reaction mixture was filtered and the precipitated material rinsed with isopropanol (100 mL). The solid was dried under vacuum at 50° C. for 6 hours, to yield the product 3(S)-2, 2-Dimethyl-thiomorpholine-3-carboxylic acid (15.47 g) as a white powdery solid.

Step 5A. Preparation of t-butyl 3(S)-2,2-dimethyl-tetrahydro-2H-1,4-thiazine-3-carboxylate.

A single neck 2.0 L flask was charged with dioxane (320 mL) and 3(S)-2,2-dimethyl-tetrahydro-2H-1,4-thiazine-3- carboxylic acid (28.0 g, 0.16 mol.). The suspension was cooled to 0° C. before adding concentrated sulfuric acid (32 mL, 0.6 mol.) via addition funnel over 10 minutes. Cooling was removed and liquid isobutylene (200 mL, 2.2 mol.) was added to the suspension. (Isobutylene was condensed in a separate graduated cylinder at −20° C. from a 400 g lecture bottle.) The gas was refluxed at room temperature with a double jacket condenser using −50° C. ethanol from a recirculating cryobath. Stirring was continued for 19 hours before work-up. The reaction was poured into a cold, biphasic mixture containing ethyl acetate (400 mL) and 2 M sodium bicarbonate solution (1 L). The organics were isolated and the aqueous was back extracted with ethyl acetate (200 mL). The combined organics were washed with brine and dried over sodium sulfate. After filtration, the solvent was concentrated under vacuum to give t-butyl 3(S)-2,2-dimethyl-tetrahydro-2H-1,4-thiazine-3-carboxylate as an oil that solidified on standing. (32.7 g, 89% yield): 1H NMR (300 MHz, CDCl3) 3.42 (s, 1H), 3.2–3.35 (m,1H), 2.7–2.85 (m, 2H), 2.05–2.2 (m, 1H), 1.37 (s, 6H), 1.3 (s, 3H), 1.2 (s,3H).

Step 6. t-Butyl 3(S)-4-(4-((pyrid-4-yl)oxy) benzenesulfonyl)-2,2-dimethyl-tetrahydro-2H-1,4-thiazine-3-carboxylate 3(S)-t-Butyl 2,2-dimethyl-tetrahydro-2H-1,4-thiazine-3-carboxylate (2.31 g, 0.01 mol) was combined with methylene chloride (25 mL) and 4-methylmorpholine (2.42 mL, 0.022 mol) to form a solution. To this solution was added 4-[(pyrid-4-yl)oxy]benzenesulfonyl chloride hydrochloride (3.22 g, 0.0105 mol). The reaction became an orange suspension accompanied by a mild exotherm. The reaction was poured into ethyl acetate (300 mL) after stirring 4 hours at room temperature. The organics were washed with 2N sodium hydroxide (50 mL) and brine solution (50 mL) before drying over sodium sulfate. The solution was filtered then concentrated under vacuum to give t-butyl 3(S)-4-(4-((pyrid-4-yl)oxy)benzenesulfonyl)-2,2-dimethyl-tetrahydro-2H-1,4-thiazine-3-carboxylate as a yellow solid (4.4 g, 94% yield). 1H NMR (300 mHz, CDCl3) 8.55 (d, 2H), 7.80 (dd, 2H), 7.17 (dd, 2H), 6.92 (dd, 2H), 4.37 (s, 1H), 4.07 (dd, 1H), 3.89 (dt, 1H), 3.15 (dt, 1H), 2.45 (d, 1H), 1.63 (s, 3H), 1.36 (s, 3H), 1.33 (s, 9H).

Step 7. Preparation of 3(S)-4-(4-((pyrid-4-yl)oxy) benzenesulfonyl)-2,2-dimethyl-tetrahydro-2H-1,4-thiazine-3-carboxylic acid hydrochloride A 100 mL flask was charged with dioxane (20 mL) and 3(S)-t-Butyl 4-(4-((pyrid-4-yl)oxy)benzenesulfonyl)-2,2-dimethyl-tetrahydro-2H-1,4-thiazine-3-carboxylate (4.37 g, 0.0094 mol). To this was added 4 M hydrogen chloride in dioxane (20 mL, 0.08 mol) and the mixture was heated to reflux. After 4 hours at reflux, the reaction mixture was cooled and filtered to give 3(S)-4-(4-((pyrid-4-yl)oxy) benzenesulfonyl)-2,2-dimethyl-tetrahydro-2H-1,4-thiazine-3-carboxylic acid hydrochloride (3.6 g, 81%) as a white solid. 1H NMR (300 mHz, CDCl3) 8.82 (d, 2 H), 8.15 (d, 2 H), 7.5–7.6 (m, 4 H), 4.4 (s, 1 H), 4.15 (dd, 1 H), 3.85 (dt, 1 H), 3.16 (dt, 1 H), 2.55 (d, 1 H), 1.64 (s, 3 H), 1.39 (s, 3 H).

EXAMPLE 1(c)

Via Methyl 3(S)-2,2-dimethyl-tetrahydro-2H-1,4-thiazine-3-carboxylate

Step 5. Preparation of methyl 3(S)-2,2-dimethyl-tetrahydro-2H-1,4-thiazine-3-carboxylate To a stirred solution of 1,2-dibromoethane (1.03 mL) in 10 mL of dry N,N-dimethylformamide at 25° C. was added over one hour via cannula, a solution D-penicillamine methyl ester hydrochloride (2.0 g), and 1,8-diazabicyclo [5.4.0]undec-7-ene (4.5 mL) in 20 mL of dry N,N-dimethylformamide. The reaction was stirred for 2 hours, then poured into sodium bicarbonate solution and extracted with ethyl acetate (3×100 mL), the organic fractions were combined, dried over sodium sulfate, filtered, isooctane added and the solvent removed. The residue was placed under vacuum for 24 hours to give methyl 3(S)-2,2-dimethyl-tetrahydro-2H-1,4-thiazine-3-carboxylate (1.41 g) as a slightly yellow oil: $^1$H NMR (300 MHz, CDCl3): δ3.68(s, 1H), 3.67(s, 3H), 3.39–3.30(m, 1H), 2.95–2.80(m, 2H), 2.31–2.18(m, 1H), 1.38(s, 3H), 1.27(s, 3H).

Step 6. Preparation of methyl 3(S)-4-(4-((pyrid-4-yl)oxy)benzenesulfonyl)-2,2-dimethyl-tetrahydro-2H-1,4-thiazine-3-carboxylate To a solution of methyl 3(S)-2,2-dimethyl-tetrahydro-2H-1,4-thiazine-3-carboxylate (0.756 g) in dichloromethane (20 mL) at room temperature was added 4-methylmorpholine (0.44 mL), followed by 4-[(pyrid-4-yl)oxy]benzenesulfonyl chloride hydrochloride 4a (1.28 g). The reaction was stirred for 24 hours then poured into pH 7 buffer (100 mL) and extracted with ethyl acetate (3×100 mL). The combined organic extracts were dried over sodium sulfate, filtered, and the solvent removed under vacuum. The residue was chromatographed on silica, eluting with 40% ethyl acetate in dichloromethane. The product-containing fractions were combined and the solvent removed. A minimum of dichloromethane was added followed by hexanes. The solvent was slowly removed which caused crystallization of methyl 3(S)-4-(4-((pyrid-4-yl)oxy)benzenesulfonyl)-2,2-dimethyltetrahydro-2H-1,4-thiazine-3-carboxylate (1.06 g) as a crystalline white solid: mp 151° C.; $^1$H NMR (300 MHz, CDCl$_3$): δ8.55(dd, J=1.5, 5 Hz, 2H), 7.76 (dd, J=2, 6.5 Hz, 2H), 7.17 (dd, J=2, 6.5 Hz, 2H), 6.89 (dd, J=1.5, 5 Hz, 2H), 4.47 (s, 1H), 4.10 (ddd, J=1.5, 1.7, 12.5 Hz, 1H), 3.79 (ddd, J=3, 12.5, 12.5 Hz, 1H), 3.46 (s, 3H), 3.18 (ddd, J=4, 13, 13.5 Hz, 1H), 2.48 (ddd, J=2.5, 3, 14 Hz, 1H), 1.65 (s, 3H), 1.29 (s, 3H).

Step 7. Preparation of 3(S)-4-(4-((pyrid-4-yl)oxy) benzenesulfonyl)-2,2-dimethyl-tetrahydro-2H-1,4-thiazine-3-carboxylic acid A solution of methyl 3(S)-4-(4-((pyrid-4-yl)oxy) benzenesulfonyl)-2,2-dimethyl-tetrahydro-2H-1,4-thiazine-3-carboxylate (15 g, 35.5 mmol) in 6 M aqueous hydrochloric acid (74 mL) was heated at reflux for 15 hours. The mixture was cooled slightly and the pH adjusted to 6 by addition of 3 M aqueous sodium hydroxide and 50% aqueous sodium hydroxide. The resulting suspension was cooled to 20° C. and the precipitate collected by filtration, washed with water (200 mL), and dried to give 3(S)-4-(4-((pyrid-4-yl)oxy)benzenesulfonyl)-2,2-dimethyl-tetrahydro-2H-1, 4-thiazine-3-carboxylic acid (9) as a white solid weighing 13.3 g (92% yield).

EXAMPLE 1(d)

Via Allyl 3(S)-2,2-dimethyl-tetrahydro-2H-1,4-thiazine-3-carboxylate

Step 5a. Preparation of allyl 3(S)-2,2-dimethyl-tetrahydro-2H-1,4-thiazine-3-carboxylate 7

A 50 mL flask was equipped with heating mantle, Dean-Stark trap, and reflux condenser and charged with 3(S)-2, 2-dimethyl-tetrahydro-2H-1,4-thiazine-3-carboxylic acid 11 (0.87 g, 0.005 mol). To this was added benzene (20 mL), p-toluenesulfonic acid monohydrate (0.856 g, 0.0045 mol), and sulfuric acid (0.14 mL, 0.0025 mol). The reaction was refluxed for 16 hours to give an amber solution while 0.2 ml of water was azeotroped. Heating was removed, and the reaction was poured into water (25 mL). The aqueous layer was separated and combined with methylene chloride (25 mL). The pH was adjusted from 1 to 9 with 1N sodium hydroxide solution. The organic was dried and the solvent removed under vacuum to give allyl 3(S)-2,2-dimethyl-tetrahydro-2H-1,4-thiazine-3-carboxylate as a colorless oil (0.47 g, 44% yield). 1H NMR (300 MHz, CDCl$_3$) 1.24 (s, 3H), 1.42 (s, 3 H), 2.3–2.36 (d, 1H), 2.8–2.9 (dt, 1H), 2.92–3.1 (dt, 1H), 3.3–3.4 (m, 1H), 3.65 (s, 1H), 4.7 (d, 2H), 5.3–5.5 (m, 2H), 5.8–6.1 (m, 1H).

Step 6. Preparation of allyl 3(S)-4-(4-((pyrid-4-yl) oxy)benzenesulfonyl)-2,2-dimethyl-tetrahydro-2H-1, 4-thiazine-3-carboxylate 4-[(4-Pyridyl)oxy]benzenesulfonyl chloride hydrochloride 4a (610 mg, 2.0 mmol) was suspended in dry acetonitrile (10 mL) and potassium carbonate (550 mg, 4.0 mmol) was added After stirring for 30 minutes, a solution of allyl 3(S)-2,2-dimethyl-tetrahydro-2H-1,4-thiazine-3-carboxylate (430 mg, 2.0 mmol) in acetonitrile (5 mL) was added dropwise over 15 minutes. The mixture was stirred at 20° C. for 24 hours. The reaction was quenched into pH 7 buffer and the pH adjusted to 7 with 2 M hydrochloric acid. The mixture was extracted with methylene chloride (2×25 mL). The combined organic layers were washed with brine, dried over sodium sulfate, and filtered. The solvent was removed under vacuum, giving allyl 3(S)-4-(4-((pyrid-4-yl) oxy)benzenesulfonyl)-2,2-dimethyl-tetrahydro-2H-1,4-thiazine-3-carboxylate as a yellow solid weighing 700 mg (78% yield). $^1$HNMR (300 MHz, CDCl$_3$) 8.53 (d, J=5 Hz, 2H), 7.78 (d, J=8 Hz, 2H), 7.15 (d, J=8 Hz, 2H), 6.90 (d, J=8 Hz, 2H), 5.84–5.71 (m, 1H), 5.30–5.22 (m, 2H), 4.49 (s, 1H), 4.35 (d, J=5 Hz, 2H), 4.10 (ddd, J=1.5,1.5,9 Hz, 1H), 3.78 (ddd, J=1.5, 12, 12 Hz, 1 H), 3.18 (ddd, J=1.5, 12, 12 Hz, 1H), 2.43 (ddd, J=1.5, 1.5, 12 Hz, 1H), 1.65 (s, 3H), 1.31 (s, 3H).

Step 7. Preparation of 3(S)-4-(4-((pyrid-4-yl)oxy) benzenesulfonyl)-2,2-dimethyl-tetrahydro-2H-1,4-thiazine-3-carboxylic acid To a solution of allyl 3(S)-4-(4-((pyrid-4-yl)oxy) benzenesulfonyl)-2,2-dimethyl-tetrahydro-2H-1,4-thiazine-3-carboxylate (0.150 g) in ethyl acetate (3 mL) at 0° C., was added N-methylaniline (0.071 mL) followed by tetrakis (triphenylphosphine)palladium(0) (0.0076 g). The reaction mixture was stirred for 2 hours at 0° C., hexanes added (4 mL), and the solid filtered off and dried in vacuo to give 3(S)-4-(4-((pyrid-4-yl)oxy)benzenesulfonyl)-2,2-dimethyl-tetrahydro-2H-1,4-thiazine-3-carboxylic acid (0.085 g) as a white solid.

EXAMPLE 2

Preparation of Intermediates of Formula 15

(a) 4-Phenoxybenzenesulfonyl chloride

To a stirred solution of 42.5 g (0.25 mol) of phenyl ether in 200 mL of dichloromethane at −20° C. under argon was slowly added 23.3 g (0.20 mol) of chlorosulfonic acid. After the addition was complete, the reaction was allowed to slowly warm to room temperature. After 16 hours, 150 mL of isooctane was added and the solution was concentrated to an oily residue. Redissolution in 200 mL of 1:3 dichloromethane/isooctane and reconcentration with cooling to about 100 mL gave a solid. The supernatant was decanted, and the solid triturated with additional isooctane and then dried in vacuo to give 55.2 g of crude 4-phenoxybenzene sulfonic acid. The crude acid was dissolved in 200 mL of dichloromethane, and 22 mL (32 g, 0.25 mol) of oxalyl chloride was added, followed by 2.5 mL of N,N-dimethylformamide. After 2 days, the reaction solution was poured into 200 mL of ice water, and extracted with 400 mL of hexane. The organic layer was washed with 100 mL of water and 100 mL of brine, dried over magnesium sulfate, and concentrated. Recrystallization of the residue from dichloromethane/isooctane gave 38.5 g of 4-phenoxybenzenesulfonyl chloride as a white solid: mp 41.5° C.; $^1$H-NMR (CDCl$_3$) δ7.10 (apparent t, 4 H, J=7 Hz), 7.28 (t, 1H, J=7 Hz), 7.46 (t, 2H, J=8 Hz), 7.98 (d, 2H, J=8.8 Hz).

(b) 4-(4-Methylphenoxy)benzenesulfonyl chloride

To a solution of 1.84 g (10.0 mmol) of 4-methyldiphenyl ether (see J. Chem Soc., Perkin Trans. 1, 1992, 407–408) with 2 mL of dichloromethane in an ice-bath was added a solution of chlorosulfonic acid (0.73 mL, 11.0 mmol) in 2 mL of dichloromethane dropwise. The resulting mixture was stirred at 0° C. to room temperature for 2 hours, and then oxalyl chloride (11.14 mL, 13.0 mmol) was added dropwise, followed by 0.15 mL of DMF. The resulting mixture was heated to 40° C. for 1 hour and then allowed to cool to room tempereature over a 2 hour period. The reaction mixture was poured into ice-pH 7 phosphate buffer (50 mL), then extracted with EtOAc:Hexane (4:3) (3×150 mL). The combined organic layers were washed with brine (75 mL). The aqueous layer was extracted with EtOAc/Hexane(4:3) (150 mL). The organic layer was dried over Na$_2$SO$_4$, then evaporated by vacuum to give crude product as white solid. This solid was triturated with hexane and collected by filtration, then dried under high vacuum to give 1.555 g (57%) of 4-(4-methylphenoxy)benzenesulfonyl chloride as white solid: mp 295–300° C. $^1$H-NMR (DMSO-d6) δ2.34 (s, 3H), 6.91–6.99 (dd, J=7.7,8.4 Hz, 4H), 7.24–7.27 (d, J=8.4 Hz, 2H), 7.61–7.63 (d, J=8.1 Hz, 2H).

Anal. calc. for $C_{13}H_{11}O_3SCl$: C, 55.22; H, 3.92; S, 11.34; Cl, 12.71. Found: C, 55.06; H, 3.95; S, 11.28; Cl, 12.71.

The following were prepared in a similar fashion:

(c) 4-(4-Bromophenoxy)benzenesulfonyl chloride

Prepared from 4-bromobiphenyl ether (Aldrich), mp 81° C.

(d) 4-(4-Chlorophenoxy)benzenesulfonyl chloride

Prepared from 4-chlorobiphenyl ether (Transworld), mp 61° C.

(e) 4-(4-Fluorophenoxy)benzenesulfonyl chloride

Prepared from 4-fluorobiphenyl ether (Riedel-de Haen), mp 76° C.

(f) 4-(4-Cyanophenoxy)benzenesulfonyl chloride

Prepared from 4-cyanobiphenyl ether (Transworld).

(g) 4-(4-Methoxyphenoxy)benzenesulfonyl chloride

Prepared from 4-methoxybiphenyl ether (which was prepared from 4-hydroxybiphenyl ether by methylation with methyl iodide and potassium carbonate in refluxing acetone).

(h) 4-(Pyrid-2-yl)oxybenzenesulfonyl chloride

Prepared from 2-phenoxypyridine (ICN): 1H NMR (CDCl3) d 8.25 (m, 1H), 8.05 (d, 2H, J=9 Hz), 7.81 (t, 1H, J=8 Hz), 7.34 (d, 2H, J=9 Hz), 7.15 (dd, 1 H, J=7 & 5 Hz), 7.06 (d, 1H, J=8 Hz).

EXAMPLE 3

(a) 3(S)-N-hydroxy-4-(4-(4-(imidazol-1-yl)phenoxy) benzenesulfonyl)-2,2-dimethyl-tetrahydro-2H-1,4-thiazine-3-carboxamide This compound was prepared in a manner similar to the procedure described in Example 1(d), except that 4-(imidazol-1-yl)biphenyl ether (prepared by the procedure described in U.S. Pat. No. 4,006,243, the disclosure of which is incorporated herein by reference) was used in place of 4-phenoxypyridine: mp 148–150° C.

(b) 3(S)-N-hydroxy-4-(4-(4-chlorophenoxy) benzenesulfonyl)-2,2-dimethyl-tetrahydro-2H-1,4-thiazine-3-carboxamide This compound was prepared in a manner similar to the procedure described in Example 1(d), except that 4-(4-chlorophenoxy)benzenesulfonyl chloride (Example 2(d)) was employed in place of 4-[(4-pyridyl)oxy] benzenesulfonyl chloride hydrochloride in step 6: mp 178–180° C.

Anal. Calcd for $C_{19}H_{21}N_2O_5S_2Cl \cdot 0.3H_2O$: C, 49.94; H, 4.63; N, 6.13; S, 14.03; Cl, 7.76. Found: C, 48.34, H, 4.77; N, 6.96; S, 13.35; Cl, 7.46

(c) 3(S)-N-hydroxy-4-(4-((pyrid-4-yl)sulfanyl) benzenesulfonyl)-2,2-dimethyl -tetrahydro-2H-1,4-thiazine-3-carboxamide This compound was prepared in a manner similar to the procedure described in Example 1(d), except that thiophenol was employed in place of phenol (in example 1(a), step 1): mp 129–131° C. with gas evolution; $^1$H NMR (300 MHz, DMSO-d6) δ10.70 (s, 1H), 8.92 (s, 1H), 8.48 (dd, J=1.5, 6 Hz, 2H), 7.83 (d, J=8.5 Hz, 2H), 7.74 (d, J=8.5 Hz, 2H), 7.25 (dd, J=1.5, 6 Hz, 2H), 4.15–4.00 (m, 1H), 4.06 (s, 1H), 3.97–3.85 (m, 1H).

EXAMPLE 4

2(R/S)-N-hydroxy-1-(4(4-bromophenoxy) benzenesulfonyl)-4-(t-butoxycarbonyl)-piperazine-2-carboxamide Step 1. A solution of 2(R/S)-piperazine-2-carboxylic acid dihydrochloride (1.06 g, 5.23 mmol) in 8 mL of 1:1 dioxane:water was brought to pH 11 with 10% aqueous sodium hydroxide and then cooled to 0° C. To this solution was added a solution of di-t-butyldicarbonate (1.37 g, 6.28 mmol) in 3 mL of dioxane, and the reaction mixture was allowed to warm slowly to room temperature overnight. The reaction mixture was then re-cooled to 0° C., and triethylamine (4.0 mL) and 4-(4-bromophenoxy)benzenesulfonyl chloride (2.00 g, 5.75 mmol, as a solution in 3 mL of dioxane) was added. The reaction mixture was stirred for 5 hours at 0° C. to room temperature, and then acidified to pH 2.5 with 2 N hydrochloric acid. The mixture was extracted with ethyl acetate (3×100 mL) and the combined organic layers were washed with 1 N aqueous sodium hydrogen sulfate and brine, dried over sodium sulfate, and concentrated. The residue was purified by chromatography on 200 g of silica, eluting with 1:10:1 ethyl acetate:hexane:acetic acid, to give 1.07 g (38%) of 2(R/S)-1-(4-(4-bromophenoxy) benzenesulfonyl)-4-(t-butoxycarbonyl)-piperazine-2-carboxylic acid: mp 112.8° C.

Step 2. To a solution of 2(R/S)-1-(4-(4-bromophenoxy) benzenesulfonyl)-4-(t-butoxycarbonyl)-piperazine-2-carboxylic acid (2.42 g, 4.47 mmol) in 15 mL of anhydrous dichloromethane at 0° C. was added O-(t-butyl-dimethylsilyl)hydroxylamine (998 mg, 6.71 mmol), followed by a solution of EDC methiodide (1.99 g, 6.71 mmol) in 20 mL of dichloromethane. The resulting mixture was stirred for 16 hours at 0° C. to room temperature, and then concentrated in vacuo. The residue was partitioned between ethyl acetate and water, and the organic layer was washed with water, saturated aqueous sodium bicarbonate, and brine. After drying over sodium sulfate, the organic layer was concentrated, and the residue was purified by rapid filtration through a pad of silica gel, eluting with 1:1 ethyl acetate:hexane. After concentration of the filtrate, the residue was triturated with hexane, filtered, and dried under vacuum to give, in two crops, 1.78 g (61%) of 2(R/S)-N-(t-butyl-dimethylsilyloxy)-1-(4-(4-bromophenoxy)benzene-sulfonyl)-4-(t-butoxycarbonyl)-piperazine-2-carboxamide as a white solid: mp 163.6° C.

Step 3. To a solution of 2(R/S)-N-(t-butyldimethylsilyloxyl)-1-(4-(4-bromophenoxy) benzenesulfonyl)-4-(t-butoxycarbonyl)-piperazine-2-carboxamide (1.599 g, 2.38 mmol) in 8 mL of anhydrous THF was added a 1 M solution of tetrabutylammonium fluoride in THF (3.6 mL). After 0.5 hours, the reaction mixture was concentrated and the residue was partitioned between ethyl acetate and water. The organic layer was washed with saturated aqueous sodium bicarbonate and brine, dried over sodium sulfate, and concentrated. Trituration of the residue with t-butyl methyl ether:hexane gave a precipitate which was filtered and dried under vacuum to give 1.320 g (99%) of 2(R/S)-N-hydroxy-1-(4-(bromophenoxy)benzenesulfonyl)-4-(t-butoxycarbonyl)-piperazine-2-carboxamide: mp 112.4° C. Anal. calc. for $C_{22}H_{26}BrN_3O_7S$: C, 47.49; H, 4.71; N, 7.55; Found: C, 47.56; H, 5.01; N, 7.42.

EXAMPLE 5

(a) 2(R/S)-N-hydroxy-1(4-(4-bromophenoxy) benzenesulfonyl)-piperazine-2-carboxamide hydrochloride 2(R/S)-N-hydroxy-1-(4-(4-bromophenoxy) benzenesulfonyl)-4-(t-butoxycarbonyl)-piperazine-2-carboxamide (999.1 mg, 1.80 mmol) was dissolved in 40 mL of 4:3:1 ethyl acetate/dichloro-methane/methanol with gentle heating. The resulting clear solution was allowed to cool to room temperature, and 5 mL of 4 M hydrogen chloride in dioxane was added. After 5 hours, the reaction mixture was partially concentrated under reduced pressure, and then diluted with ethyl acetate:ethyl ether. The precipitate was collected by filtration, washed with ethyl acetate and ethyl ether, and dried under vacuum to give 548.8 mg (62%) of 2(R/S)-N-hydroxy-1-(4-(4-bromophenoxy) benzenesulfonyl)-piperazine-2-carboxamide hydrochloride as a white solid: mp 186.6° C.

Anal. calc. for $C_{17}H_{19}ClBrN_3O_5S$: C, 41.43; H, 3.89; N, 8.53; Found: C, 41.47; H, 3.96; N, 8.38

The following compound was prepared in a similar manner:

(b) 2(R/S)-N-hydroxy-1-(4-phenoxybenzenesulfonyl)-piperazine-2-carboxamide mp 160.4° C.;

Anal. calc. for $C_{17}H_{19}N_3O_5S$: C, 54.10; H, 5.07; N, 11.13; S, 8.50; Found: C, 54.04; H, 5.09; N, 11.06; S, 8.44

EXAMPLE 6

(a) 2(R/S)-N-hydroxy-1-(4-(4-chlorophenoxy)benzenesulfonyl)-4-(N-methylcarbamoyl)-piperazine-2-carboxamide Step 1. To a suspension of 1.20 g of 2(R/S)-4-(benzyloxycarbonyl)-piperazine-2-carboxylic acid (obtained according to the method of M. E. Freed and J. R. Potoski, U.S. Pat. No. 4,032,639 (1977), the disclosure of which is herein incorporated by reference) in dichloromethane (2.5 mL) at 0° C. was added 0.63 mL of trimethylsilyl chloride. After 10 minutes, triethylamine (1.55 mL) was added, followed by addition of 1.37 g of 4-(4-chlorophenoxy)benzene-sulfonyl chloride. After 3 hours, the mixture was partitioned between dichloromethane and pH 4 citrate buffer. The organic layer was washed with water, dried over sodium sulfate, and concentrated. The residue was purified by chromatography, eluting with 0.5% acetic acid in 95:5 dichloromethane/ethanol, to provide 2.05 g (85%) of 2(R/S)-1-(4-(4-chlorophenoxy)benzenesulfonyl)-4-(benzyloxycarbonyl)-piperazine-2-carboxylic acid: mp 104.2° C.

Anal. calc. for $C_{25}H_{23}ClN_2O_7S$: C, 56.55; H, 4.37; N, 5.28; S, 6.04; Found: C, 56.65; H, 4.41; N, 5.22; S, 6.10.

Step 2. A solution of 2(R/S)-1-(4-(4-chlorophenoxy)benzenesulfonyl)-4-(benzyloxycarbonyl)-piperazine-2-carboxylic acid (2.21 g) in 18:1:1 ethanol:ethyl acetate:water was hydrogenated at 1 atm over 10% Pd/C (0.22 g) for 1 day. The catalyst was removed by filtration and the solution concentrated to give 2(R/S)-1-(4-(4-chlorophenoxy)benzenesulfonyl)-piperazine-2-carboxylic acid of ca. 95% purity, which was used without further purification.

Step 3. To a solution of 2(R/S)-1-(4-(4-chlorophenoxy)benzenesulfonyl)-piperazine-2-carboxylic acid (0.987 g) and triethylamine (0.41 mL) in 20 mL of anhydrous DMF was added methyl isocyanate (0.16 mL). After 6 hours, the reaction was partitioned between dichloromethane and 1 N sodium bisulfate. The aqueous layer was extracted twice more with dichloromethane, and the combined organic layers were dried (sodium sulfate) and concentrated. The residue was purified by chromatography, eluting with 85:15 dichloromethane:ethanol containing 0.5% acetic acid, to provide 0.918 g (81%) of 2(R/S)-1-(4-(4-chlorophenoxy)benzenesulfonyl)-4-(N-methylcarbamoyl)-piperazine-2-carboxylic acid: mp 212.7° C. Anal. calc. for $C_{19}H_{20}ClN_3O_6S$: C, 50.27; H, 4.44; N, 9.26; S, 7.06; Found: C, 50.56; H, 4.40; N, 9.38; S, 6.93.

Step 4. To a solution of O-(t-butyldimethylsilyl)hydroxylamine (0.282 g ) in 12 mL of 5:1 dichloromethane:DMF at 0° C. was added 0.580 g of 1-(4-(4-chlorophenoxy) benzenesulfonyl)-4-(N-methylcarbamoyl)-2R/S-piperazinecarboxylic acid followed by EDC hydrochloride (0.294 g) and the reaction mixture was stirred for 15 minutes at 0° C. and then allowed to warm to room temperature. After 1.5 hours, the reaction was partitioned between ethyl acetate and aqueous sodium bicarbonate. The organic layer was washed with water and brine, dried over sodium sulfate, and concentrated. The residue was crystallized by slow evaporation from dichloromethane/t-butyl methyl ether/isooctane to provide 0.643 g (86%) of 2(R/S)-N-(t-butyl-dimethylsilyloxy)-1-(4-(4-chlorophenoxy)benzenesulfonyl)-4-(N-methylcarbamoyl)-piperazine-2-carboxamide as a white solid: mp 171.0° C.

Anal. calc. for $C_{25}H_{35}ClN_4O_6SSi$: C, 51.49; H, 6.05; N, 9.61; S, 5.50; Found: C, 51.59; H, 6.06; N, 9.67; S, 5.58.

Step 5. To a solution of 2(R/S)-N-(t-butyldimethylsilyloxyl)-1-(4-(4-chlorophenoxy)benzenesulfonyl)-4-(N-methylcarbamoyl)-piperazine-2-carboxamide in 20 mL of methanol at 25° C. was added 0.5 mL of trifluoroacetic acid. After 30 minutes, 20 mL of toluene was added and the solution was concentrated. The residue was recrystallized from dichloromethane/t-butyl methyl ether/isooctane to give 781 mg (99%) of 2(R/S)-N-hydroxy-1-(4-(4-chlorophenoxy)-benzenesulfonyl)-4-(N-methylcarbomoyl)-piperazine-2-carboxamide as a white solid: mp 133.2° C.

Anal. calc. for $C_{19}H_{21}ClN_4O_6S$: C, 48.66; H, 4.51; N; 11.95; S, 6.84; Found C, 48.74; H, 4.53; N; 11.90; S, 6.91.

The following compounds can be prepared in a similar manner:

(b) 2(R)-N-hydroxy-1-(4-(4-fluorophenoxy)benzenesulfonyl)-4-(N-methylcarbamoyl)-piperazine-2-carboxamide (c) 2(R)-N-hydroxy-1-(4-(4-methoxyphenoxy)benzenesulfonyl)-4-(N-methylcarbamoyl)-piperazine-2-carboxamide; and (d) 2(R/S)-N-hydroxy-1-(4-(4-chlorophenoxy)benzenesulfonyl)-4-(N-isopropylcarbamoyl)-piperazine-2-carboxamide

EXAMPLE 7

(a) 2(R/S)-N-hydroxy-1-(4-phenoxybenzenesulfonyl)-4-acetyl-piperazine-2-carboxamide Step 1. To a stirred solution of 42.5 g (0.25 mol) of phenyl ether in 200 mL of dichloromethane at −20° C. under argon was slowly added 23.3 g (0.20 mol) of chlorosulfonic acid. After the addition was complete, the reaction was allowed to slowly warm to room temperature. After 16 hours, 150 mL of isooctane was added and the solution was concentrated to an oily residue. Redissolution in 200 mL of 1:3 dichloromethane/isooctane and reconcentration with cooling to about 100 mL gave a solid. The supernatant was decanted, and the solid triturated with additional isooctane and then dried in vacuo to give 55.2 g of crude 4-phenoxybenzene sulfonic acid. The crude acid was dissolved in 200 mL of dichloromethane, and 34 g (0.25 mol) of oxalyl chloride was added, followed by 2.5 mL of DMF. After 2 days, the reaction solution was poured into 200 mL of ice water, and extracted with 400 mL of hexane. The organic layer was washed with 100 mL of water and 100 mL of brine, dried over magnesium sulfate, and concentrated. Recrystallization of the residue from dichloromethane/isooctane gave 38.5 g of 4-phenoxybenzenesulfonyl chloride as a white solid: mp 41.5° C.

Step 2. To a stirred solution of 2(R/S)-piperazine-2-carboxylic acid (1.30 g, 10.0 mmol) and triethylamine (3.6 mL) in 25 mL of 2:2:1 dioxane/water/acetonitrile at −20° C.

was added dropwise 1.13 mL (1.22 g, 12.0 mmol) of acetic anhydride. After 2 hours at −20° C., an additional 1.5 mL of triethylamine was added, followed by 2.69 g (10 mmol) of 4-phenoxybenzenesulfonyl chloride. The reaction mixture was allowed to warm slowly to room temperature. After 18 hours, the reaction was partitioned between 100 mL of 0.5 N potassium dihydrogen phosphate and 100 mL of ethyl acetate. The aqueous layer was acidified with 10 mL of 2 M sulfuric acid, and extracted with an additional 100 mL of ethyl acetate. The combined organic layers were dried over sodium sulfate and concentrated. The residue was dissolved in 100 mL of 1:1 toluene/methanol, and trimethylsilyldiazomethane (2 M solution in hexane) was added dropwise until the yellow color no longer dissipated (about 15 mL). After addition of 2 drops of acetic acid to consume excess trimethylsilyl-diazomethane, the solution was concentrated and the residue was purified by chromatography on 150 g of silica gel, eluting with a 80% ethyl acetate/hexane to ethyl acetate gradient. Concentration of the product-containing fractions gave an oil which solidified upon trituration with t-butyl methyl ether/hexane to give 1.86 g (44%) of methyl 2(R/S)-1-(4-phenoxybenzenesulfonyl)-4-acetyl-piperazine-2-carboxylate: mp 118° C.

Anal. calc. for $C_{20}H_{22}N_2O_6S$: C, 57.41; H, 5.30; N, 6.69; S, 7.66; Found: C, 57.38; H, 5.29; N, 6.75; S, 7.72.

Step 3. To a solution of methyl 2(R/S)-1-(4-phenoxybenzenesulfonyl)-4-acetyl-piperazine-2-carboxylate (1.672 g) in 12 mL of THF and 6 mL of methanol was added in a dropwise manner 4 mL of 2 N aqueous lithium hydroxide. After 1 hour, the reaction solution was partitioned between 100 mL of ethyl acetate and 25 mL of 1 N aqueous sodium bisulfate. The organic layer was washed with brine, dried over sodium sulfate, and concentrated. The residue was triturated with t-butyl methyl ether and filtered to give 1.544 g (96%) of 2(R/S)-1-(4-phenoxybenzenesulfonyl)-4-acetyl-piperazine-2-carboxylic acid as a white solid: mp 213° C.

Anal. calc. for $C_{19}H_{20}N_2O_6S$: C, 56.43; H, 4.98; N, 6.93; S, 7.93; Found: C, 56.50; H, 4.96; N, 6.90; S, 8.01.

Step 4. To a solution of O-(t-butyldimethylsilyl) hydroxylamine (0.575 g) in 13 mL of dichloromethane at 0° C. was added 1.212 g of 2(R/S)-1-(4-phenoxybenzenesulfonyl)-4-acetyl-piperazine-2-carboxylic acid. To this mixture was added 2.0 mL of DMF, resulting in a clear solution. After about 3 minutes, EDC hydrochloride (0.634 g) was added in one portion, and the reaction was stirred for 15 minutes at 0° C. and then allowed to warm to room temperature. After 2 hours, the reaction was partitioned between 100 mL of 3:1 ethyl acetate/hexane and 50 mL of water. The organic layer was washed with saturated aqueous sodium bicarbonate, 1 N aqueous sodium bisulfate, and pH 7 phosphate buffer/brine, dried and concentrated. Trituration of the residue with t-butyl methyl ether/hexane and filtration gave 1.351 g (84%) of 2(R/S)-N-(t-butyldimethylsilyloxy)-1-(4-phenoxy-benzenesulfonyl)-4-acetyl-piperazine-2-carboxamide as a white solid: mp 146° C.

Anal. calc. for $C_{24}H_{35}N_2O_6SSi$: C, 56.26; H, 6.61; N, 7.87; S, 6.01; Found: C, 56.33; H, 6.66; N, 7.94; S, 6.09.

Step 5. To a solution of 2(R/S)-N-(t-butyldimethylsilyloxy)-1-(4-phenoxybenzenesulfonyl)-4-acetyl-piperazine-2-carboxamide (1.200 g, 2.25 mmol) in 20 mL of methanol at 25° was added 0.5 mL of trifluoroacetic acid. After 1 hours, 20 mL of toluene was added and the solution was concentrated. The residue was recrystallized from dichloromethane/t-butyl methyl ether to give 850 mg (84%) of 2(R/S)-N-hydroxy-1-(4-phenoxybenzenesulfonyl)-4-acetyl-piperazine-2-carboxamide as a white solid: mp 171° C. (decomp).

Anal. calc. for $C_{19}H_{21}N_3O_6S \cdot 0.25\ C_5H_{12}O$ (t-BuOMe) •0.25 $H_2O$: C, 54.63; H, 5.55; N, 9.44; S, 7.20; Found: C, 54.62; H, 5.45; N; 9.38; S, 7.20.

The following compounds can be prepared in a similar manner from enantiomerically pure 2(R)-piperazine-2-carboxylate:

(b) 2(R)-N-hydroxy-1-(4-(4-chlorophenoxy) benzenesulfonyl-4-acetyl-piperazine-2-carboxamide (c) 2(R)-N-hydroxy-1-(4-phenoxybenzenesulfonyl)-4-(methoxyacetyl)-piperazine-2-carboxamide (d) 2(R)-N-hydroxy-1-(4-phenoxybenzenesulfonyl)-4-(isobutyryl)-piperazine-2-carboxamide (e) 2(R)-N-hydroxy-1-(4-(pyrid-4-yl) oxybenzenesulfonyl)-4-acetyl-piperazine-2-carboxamide (f) 2(R)-N-hydroxy-1-(4-(4-fluorophenoxy) benzenesulfonyl)-4-acetyl-piperazine-2-carboxamide; and (g) 2(R)-N-hydroxy-1-(4-(4-chlorophenoxy) benzenesulfonyl)-4-(dimethylaminoacetyl)-piperazine-2-carboxamide

EXAMPLE 8

(a) 3(R)-N-hydroxy-4-(4-(4-chlorophenoxy) benzenesulfonyl)-morpholine-3-carboxamide Step 1. To mixture of D-serine methyl ester hydrochloride (11.20 g) and N-methylmorpholine (16.5 mL) in 385 mL of 10:1 dichloromethane DMF at −10° C. was added, in portions over a 2 hour period, 18.18 g of 4-(4-chlorophenoxy)benzenesulfonyl chloride. The mixture was stirred an additional 2.5 hours at −10° C., and then partitioned between 1 M aqueous sodium bisulfate (200 mL) and 4:1 ethyl acetate:hexane (400 mL). The aqueous layer was extracted with additional ethyl acetate:hexane (200 mL) and the combined organic layers were washed with water, 1 M aqueous sodium bisulfate, saturated aqueous sodium bicarbonate, and brine. After drying over sodium sulfate, the solution was concentrated almost to dryness, and the residue was crystallized from t-butyl methyl ether:dichloromethane:isooctane to give two crops of 18.09 g and 3.20 g. Total yield of N-(4-(4-chlorophenoxy)benzenesulfonyl)-D-serine methyl ester was 21.29 g: mp 103.9° C.

Step 2. To a stirred solution of N-(4-(4-chlorophenoxy) benzenesulfonyl)-D-serine methyl ester (8.3 g) and triphenyl phosphine (6.79 g) in 150 mL of THF was added diethyl azodicarboxylate (4.07 mL) in 2.5 mL THF. After 18 hours, the reaction was partitioned between 1:1 ethyl acetate:hexane and water, and the organic layer was washed with brine, dried over sodium sulfate, and concentrated. Chromatography of the residue (20% ethyl acetate:hexane) provided 7.05 g (89%) of methyl 2(R)-1-(4-(4-chlorophenoxy)benzenesulfonyl)aziridine-2-carboxylate as a thick syrup.

Step 3. To a stirred solution of methyl 2(R)-1-(4-(4-chlorophenoxy)benzenesulfonyl)aziridine-2-carboxylate (6.81 g) in 13 mL of 2-bromoethanol at 0° C. was added dropwise 1.85 mL of boron trifluoride etherate. The reaction was stirred for 30 minutes at 0° C. and for 6 hours at room temperature, and then partitioned between 200 mL of 0.1 N pH 7 phosphate buffer and 250 mL of 2:1 ethyl acetate:hexane. The organic layer was washed with water and brine, dried over sodium sulfate, and concentrated. Recrystallization of the residue from t-butyl methyl ether/isooctane gave 3.69 g of a slightly impure solid, which was again recrystallized from t-butyl methyl ether/isooctane to yield 2.35 g of fine white needles. The combined filtrates were concentrated and the residue was chromatographed on 150 g of silica gel with 40% to 50% t-butyl methyl ether in hexane. The product-containing fractions were partially concentrated to ca. 50 mL volume, and the crystalline solid isolated by filtration to provide an additional 1.11 g of product. Total yield of N-(4-(4-chlorophenoxy)benzenesulfonyl)-O-(2-bromoethyl)-D-serine methyl ester was 4.36 g (51%): mp 98° C.

Step 4. To a solution of N-(4-(4-chlorophenoxy)benzenesulfonyl)-O-(2-bromoethyl)-D-serine methyl ester (3.94 g) in 40 mL of anhydrous DMF at 0° C. was added 4.0 g of powdered potassium carbonate. After the addition, the ice bath was removed, and the mixture was stirred vigorously as the reaction was allowed to warm to room temperature. After 1 hour, the mixture was partitioned between 200 mL of water and 200 mL of 1:1 ethyl acetate:hexane. The organic layer was washed with 200 mL of 0.1 N pH 7 phosphate buffer, 50 mL of water, and 50 mL of brine, dried over sodium sulfate, and concentrated. The resulting thick syrup (3.86 g) was dissolved in 60 mL of 4:1:1 dioxane:methanol:water at 0° C. and 10 mL of 2N aqueous lithium hydroxide was added. The mixture was stirred for 30 minutes at 0° C. and then allowed to warm to room temperature. After an additional hour, the reaction was partitioned between 250 mL of 2:1 ethyl acetate:hexane and 100 mL of 0.5 N aqueous sodium bisulfate. The aqueous layer was extracted with an additional 50 mL of ethyl acetate:hexane, and the combined organic layers were washed with brine, dried over sodium sulfate, and concentrated. The residue was chromatographed on 150 g of silica with 70% ethyl acetate:hexane containing 0.5% acetic acid. The product-containing fractions were concentrated to provide 2.98 g (94%) of 3(R)-4-(4-(4-chlorophenoxy)benzenesulfonyl)-morpholine-3-carboxylic acid as a syrup which solidified on standing: mp 161.8° C.

Step 5. To a solution of 3(R)-4-(4-(4-chlorophenoxy)benzenesulfonyl)-morpholine-3-carboxylic acid (3.06 g) in 35 mL of 6:1 dichloromethan:DMF at 0° C. was added O-(t-butyldimethysilyl)-hydroxylamine (1.47 g) followed by EDC hydrochloride (1.77 g). The solution was stirred for 30 min at 0-C. and then allowed to warm to room temperature. After 2 hours, the reaction was partitioned between 150 mL of 1:1 ethyl acetate:hexane and 100 mL of water. The organic layer was washed with cold 0.1 N aqueous sodium bisulfate (25 mL), 0.1 N aqueous sodium bicarbonate (25 mL), and brine, dried ever sodium sulfate, and concentrated to an oil which solidified upon standing. Trituration with hexane and filtration gave 3.46 g (85%) of 3(R)-N-(t-butyldimethylsilyloxy)-4-(4-(4-chlorophenoxy)benzenesulfonyl)-morpholine-3-carboxamide as a white solid: mp 129.6° C.

Step 6. To a suspension of 3(R)-N-(t-butyldimethylsilyloxy)4-(4-(4-chlorophenoxy)benzenesulfonyl)-morpholine-3-carboxamide (3.35 g) in 25 mL of methanol at 25° C. was added 0.3 mL of trifluoroacetic acid. After 1 hour, 20 mL of toluene was added and the solution was concentrated to a volume of about 10 mL. Upon addition of an additional 10 mL of toluene, a solid precipitated. After a few minutes, 20 mL of hexane was added and the solid was collected by filtration and dried in vacuo to give 2.65 g (95%) of 3(R)-N-hydroxy-4-(4-(4-chlorophenoxy)benzenesulfonyl)-morpholine-3-carboxamide ծ0.33 toluene as a white solid: mp 104-C. Anal. cal. for $C_{17}H_{17}ClN_2O_6S.0.33\ C_7H_8$: C, 52.32; H, 4.47; N, 6.32; Cl, 8.00; S, 7.23; Found: C, 52.31; H, 4.47; N, 6.26; Cl, 7.97; S, 7.38.

The following compounds can be prepared in similar manner:

(b) 3(R)-N-hydroxy-4-(4-phenoxybenzenesulfonyl)-morpholine-3-carboxamide (c) 3(R)-N-hydroxy-4-(4-(4-methoxyphenoxy)benzenesulfonyl)-morpholine-3-carboxamide (d) 3(R)-N-hydroxy-4-(4-(pyrid4-yl)oxybenzenesulfonyl)-morpholine-3-carboxamide (e) 3(R)-N-hydroxy-4-(4-(4-fluorophenoxy)benzenesulfonyl)-morpholine-3-carboxamide; and (f) 3(R)-N-hydroxy-4-(4-(4-(imidazol-2-yl)phenoxy)benzenesulfonyl)-morpholine-3-carboxamide

EXAMPLE 9

(a) 2(R)-N-hydroxy-1-(4-(4-chlorophenoxy)benzenesulfonyl)-4-(t-butoxycarbonyl)-piperazine-2-carboxamide Step 1. To a solution of 2(R)-piperazine-2-carboxylic acid (1.30 g) and triethylamine (3.50 mL) in 25 mL of 3:2 acetonitrile:water at −15° C. was added BOC-ON (2.70 g) in one portion. The mixture was allowed to warm slowly to 25° C. overnight, and then concentrated to a volume of ca. 10 mL. The resulting mixture was partitioned between 25 mL of water and 50 mL of 4:1 ethyl acetate:hexane. The aqueous layer was further washed with dichloromethane (3×10 mL) and then concentrated. The semi-solid residue was triturated with ethanol and filtered to give 1.18 g of 2(R)-4-(t-butoxycarbonyl)-piperazine-2-carboxylate. Concentration of the filtrate gave a second crop of 0.58 g: total yield of 2(R)4-(t-butoxycarbonyl)-piperazine-2-carboxylic acid was 1.76 g (76%).

Step 2. To a stirred suspension of 2(R)-4-(t-butoxycarbonyl)-piperazine-2-carboxylic acid (4.62 g) and N-methylmorpholine (5.5 mL) in 90 mL of 2:1 dichloromethane:DMF was added dropwise trimethylsilyl chloride (2.79 mL) with cooling in a 15° C. water bath. After 1 hour, diisopropylethylamine (3.5 mL) was added and the mixture was stirred for another hour, at which point little solid remained. Additional trimethylsilyl chloride (0.20 mL) was added, and after 30 minutes, the reaction was a homogenous solution, and 4-(4-chlorophenoxy)benzenesulfonyl chloride (6.67 g) was added in one portion. The reaction was stirred for 2 hours, and then quenched with ca. 10 mL of water. After 30 minutes, the mixture was partitioned between 300 mL of 2:1 ethyl acetate:hexane and 100 mL of 0.5 N aqueous sodium bisulfate. The organic layer was washed with 100 mL each of 0.2 N and 0.05 N sodium bisulfate and with 50 mL of brine, dried (sodium sulfate), and concentrated. The residue was purified by chromatography on 200 g of silica, eluting with a gradient of 30% to 40% to 50% ethyl acetate:hexane containing 0.5% acetic acid, to give 9.33 g of 2(R)-4-(t-butoxycarbonyl)-1-(4-(4-chlorophenoxy)-benzenesulfonyl)-piperazine-2-carboxylic acid as a solid foam containing traces of solvent.

Step 3. To a solution of 2(R)-4-(t-butoxycarbonyl)-1-(4-(4-chlorophenoxy)benzenesulfonyl)-piperazine-2-charboxylic acid (995 mg) in 12 mL of dichloromethane at 0° C. was added O-(t-butyl-dimethylsilyl)hydroxylamine (430 mg) followed by EDC hydrochloride (460 mg). After 20 minutes, the reaction was allowed to warm to 25° C. After 2 hours, the reaction was partitioned between water and 1:1 ethyl acetate:hexane. The organic layer was washed with water and cold 0.1 N aqueous sodium bisulfate, and finally with pH 7 phosphate buffer/brine. The organic layer was dried over sodium sulfate, and concentrated to a solid. Dissolution in dichloromethane, dilution with isooctane, and partial concentration gave a heavy precipitate, which upon filtration and drying provided 1.107 g (88%) of 2(R)-N-(t-butyldimethylsilyloxy)-4-(t-butoxycarbonyl)-1-(4-(4-chlorophenoxy)benzenesulfonyl)-piperazine-2-carboxamide: mp 181.6° C.

Anal. calc for $C_{28}H_{40}ClN_3O_7SSi$: C, 53.70; H, 6.44; N, 6.71; S, 5.12; Found: C, 53.79; H, 6.46; N, 6.72; S, 5.19.

Step 4. To a solution of 2(R)-N-(t-butyldimethylsilyloxy)-4-(t-butoxy-carbonyl)-1-(4-chlorophenoxy)benzenesulfonyl)-piperazine-2-carboxamide (100 mg) in methanol (4 mL) was added TFA (0.2 mL). After 1 hour, toluene (20 mL) was added and the solution was concentrated to a solid residue, which was recrystallized from methanol to give 48 mg of 2(R)-N-hydroxy-1-(4-(4-chlorophenoxy)-benzenesulfonyl)4-(t-butoxycarbonyl)-piperazine-2-carboxamide as fine white needles: mp 94.6° C.

The following compounds were prepared in a similar manner:

(b) 2(R)-N-hydroxy-1-(4-(4-fluorophenoxy)benzenesulfonyl)-4-(t-butoxycarbonyl)-piperazine-2-carboxamide mp 151.2° C.;

(c) 2(R/S)-N-hydroxy-1-(4-(4-cyanophenoxy)benzenesulfonyl)-4-(t-butoxycarbonyl)-piperazine-2-carboxamide mp 131.3° C.; and (d) 2(R/S)-N-hydroxy-1-(4-(pyrid-2-yl)oxybenzenesulfonyl)-4-(t-butoxycarbonyl)-piperazine-2-carboxamide mp 133.5° C.;

Anal. calc. for $C_{21}H_{26}N_4O_7S$: C, 52.71; H, 5.48; N, 11.71; S, 6.70; Found: C, 5.54; H, 5.48; N, 11.61; S, 6.75.

EXAMPLE 10

(a) 2(R)-N-hydroxy-1-(4-(4-chlorophenoxy)benzenesulfonyl)-piperazine-2-carboxamide hydrochloride To a solution of 2(R)-N-(t-butyldimethylsilyloxy)-4-(t-butoxycarbonyl)-1-(4-(4-chlorophenoxy)benzenesulfonyl)-piperazine-2-carboxamide (313 mg) in 7 mL of 6:1 dichloromethane:methanol was added 2.0 mL of 4M HCl in dioxane. After 1 hour, the solution was partially concentrated to ca. 2 mL, diluted with 5 mL of ethyl acetate, and reconcentrated to near dryness. The residue was triturated with ethyl acetate, filtered, and dried in vacuo to provide 198 mg (88%) of 2(R)-N-hydroxy-1-(4-(4chlorophenoxy)benzenesulfonyl)-piperazine-2-carboxamide hydrochloride as a white solid: mp 169° C.

Anal. calc. for $C_{17}H_{19}Cl_2N_3O_5S$: C, 45.54; H, 4.27; N, 9.37; Cl, 15.82; S, 7.15; Found: C, 45.59; H, 4.25; N, 9.20; Cl, 15.66; S, 7.02.

The following compound was prepared in a similar manner:

(b) 2(R)-N-hydroxy-1-(4-(4-fluorophenoxy)benzenesulfonyl)-piperazine-2-carboxamide hydrochloride:

mp 150.8° C.

The following compounds can be prepared in a similar manner:

(c) 2(R)-N-hydroxy-1-(4-(4-methoxyphenoxy)benzenesulfonyl)-piperazine-2-carboxamide hydrochloride (d) 2(R)-N-hydroxy-1-(4-(4-methylphenoxy)benzenesulfonyl-piperazine-2-carboxamide hydrochloride; and (e) 2(R)-N-hydroxy-1-(4-(pyrazol-3-yl)benzenesulfonyl)-piperazine-2-carboxamide hydrochloride

EXAMPLE 11

(a) 2(R)-N-hydroxy-1-(4-(4-chlorophenoxy)benzenesulfonyl)-4-methyl-piperazine-2-carboxamide hydrochloride To a solution of 313 mg of 2(R)-N-(t-butyldimethylsilyloxy)-4-(t-butoxycarbonyl)-1-(4-(4-chlorophenoxy)benzenesulfonyl)-piperazine-2-carboxamide in 2 mL of dichloromethane was added 1 mL of trifluoroacetic acid. After 2 hours, 2 mL of methanol was added and the solution was stirred for 15 minutes and then diluted with 5 mL of toluene. Concentration gave an oily residue, which partitioned between brine/saturated sodium bicarbonate and ethyl acetate. The aqueous layer was extracted with two additional portions of ethyl acetate, and the combined organic layers were dried over sodium sulfate and concentrated to give 231 mg of slightly impure 2(R)-N-hydroxy-1-(4-(4-chlorophenoxy)benzenesulfonyl)-piperazine-2-carboxamide. To a solution of 186 mg of this solid and diisopropylethylamine (0.15 mL) in 3.5 mL of 6:1 acetonitrile:DMF was added iodomethane (0.031 mL). After 1.5 hours at 25° C., the reaction was diluted with ca. 5 mL of ethyl acetate and concentrated. The residue was partitioned between 0.5 M aqueous sodium bicarbonate and ethyl acetate. The aqueous phase was extracted with a second portion of ethyl acetate, and the combined organic layers were washed with brine, dried over sodium sulfate, and concentrated. The residue was chromatographed on 10 g of silica gel, eluting with gradient of 6% to 8% to 10% methanol in dichloromethane. The product-containing fractions were concentrated, and the residue was dissolved in 5 mL of ethyl acetate:dichloromethane (4:1). To this solution was added 0.4 mL of 1 M HCl in ethanol, and the mixture was concentrated to a white residue, which was triturated with ethyl acetate and filtered to give 115 mg of 2(R)-N-hydroxy-1-(4-(4-chlorophenoxy)benzenesulfonyl)-4-methyl-piperazine-2-carboxamide hydrochloride as a white solid: mp 152° C. (decomp).

Anal. calc. for $C_{18}H_{21}Cl_2N_3O_5S$: C, 46.76; H, 4.58; N, 9.09; Cl, 15.34; S, 6.93; Found: C, 46.65; H, 4.65; N, 8.98; Cl, 15.18; S, 6.84.

The following compounds were prepared in a similar manner:

(b) 2(R)-N-hydroxy-1-(4-phenoxybenzenesulfonyl)-4-methyl-piperazine-2-carboxamide mp 127.7° C.;

Anal. calc. for $C_{18}H_{21}N_3O_5S_1 3 0.5$ hexane: C, 56.71; H, 5.98; N, 10.18;

Found: C, 56.70; H, 5.99; N, 10.05;

(c) 2(R)-N-hydroxy-1-(4-(4-chlorophenoxy) benzenesulfonyl)-4-(ethoxycarbonylmethyl)-piperazine-2-carboxamide hydrochloride mp 163.7° C.;

Anal. calc. for $C_{21}H_{25}Cl_2N_3O_7S$: C, 47.20; H, 4.72; N, 7.86; S, 6.00;

Found: C, 47.09; H, 4.77; N, 7.93; S, 5.90; and (d) 2(R)-N-hydroxy-1-(4-(4-fluorophenoxy) benzenesulfonyl)-4-methyl-piperazine-2-carboxamide Anal. calc. for $C_{18}H_{20}FN_3O_5S$: C, 52.80; H, 4.92; N, 10.26; S, 7.83; Found: C, 52.66; H, 4.95; N, 10.01; S, 7.56.

The following compound can be prepared in a similar manner:

(e) 2(R)-N-hydroxy-1-(4-(4-fluorophenoxy) benzenesulfonyl)-4-(cyclopropylmethyl)-piperazine-2-carboxamide hydrochloride

EXAMPLE 12

(a) 2(R)-N-hydroxy-1-(4-(4-chlorophenoxy) benzenesulfonyl)-4-(methanesulfonyl)-piperazine-2-carboxamide Step 1. To a suspension of 1.00 g of 2(R)-N-(t-butyldimethylsilyloxy)-4-(t-butoxycarbonyl)-1-(4-(4-chlorophenoxy)benzenesulfonyl)-piperazine-2-carboxamide in 4 mL of dichloromethane was added 3 mL of trifluoroacetic acid, resulting in a clear solution. After 2 hours at 25° C., the solution was concentrated to near dryness, and the residue was dissolved in 10 mL of methanol. After 10 minutes, the solution was reconcentrated, the residual syrup was dissolved in 50 mL of methanol, and ca. 15 mL of IRA-68 weakly basic resin was added. The mixture was stirred gently for 2 hours, and then the resin was removed by filtration. The filtrate was concentrated to a white solid, which was triturated with hot t-butyl methyl ether, and after cooling to −20° C., filtered to provide 2(R)-N-hydroxy-1-(4-(4-chlorophenoxy)benzenesulfonyl)-piperazine-2-carboxamide (0.552 g) as a white solid: mp 147.0° C.

Step 2. To a suspension of 2(R)-N-hydroxy-1-(4-(4-chlorophenoxy)-benzenesulfonyl)-piperazine-2-carboxamide (1.03 g) in 20 mL of dichloromethane was added 0.70 mL of triethylamine, 0.41 mL of N-methylmorpholine, and, in a dropwise manner, 0.67 mL of trimethyl-chlorosilane. After 1.5 hours, the mixture was cooled to 0° C. and methanesulfonyl chloride (0.20) was added dropwise. The mixture was stirred for 30 minutes at 0° C. and then allowed to warm to 25° C. After an additional 45 minutes, the mixture was partitioned between 12.5 mL of 4:1 ethyl acetate:hexane and 50 mL of 0.2 M aqueous sodium bisulfate. The organic layer was washed with an additional 50 mL of aqueous sodium bisulfate, and then with 2.5 mL of 1 M phosphate buffer (pH 7) and finally with brine. The organic layer was dried over sodium sulfate and concentrated, and the residue was purified by chromatography (75 g of silica gel, eluting with 40% to 50% ethyl acetate:dichloromethane containing 1% acetic acid). First to elute were several mixed fractions, followed by pure product fractions, which were pooled and concentrated. The residue was re-concentrated from toluene (to remove residual acetic acid), and finally from dichloromethane:t-butyl methyl ether to give a white solid. Trituration with 2:1 t-butyl methyl ether:hexane (ca. 15 mL) and filtration gave 2(R)-N-hydroxy-1-(4-(4-chlorophenoxy)benzenesulfonyl)-4-(methanesulfonyl)-piperazine-2-carboxamide (0.646 g) as a white powder.

Anal. Calcd for $C_{18}H_{20}ClN_3O_7S_2.0.35$ hexane: C, 46.41; H, 4.83; N, 8.08; S, 12.33. Found: C, 46.43, H, 4.93; N, 8.04; S, 12.25.

The following compounds were prepared in a similar manner:

(b) 2 R)-N-hydroxy-1-(4-(4-fluorophenoxy) benzenesulfonyl)-4-(methanesulfonyl)-piperazine-2-carboxamide mp 102.5° C.

(c) 2 (R/S)-N-hydroxy-1-(4-(4-methoxyphenoxy) benzenesulfonyl-4-(methanesulfonyl)-piperazine-2-carboxamide Anal. calc. for $C_{19}H_{32}N_3O_8S_2$: C, 47.00; H, 4.78; N, 8.65; S, 13.21; Found: C, 47.09; H, 4.81; N, 8.57; S, 13.11.

(d) 2 (R)-N-hydroxy-1-(4-(4-chlorophenoxy) benzenesulfonyl)-4-(1-methylimidazole-4-sulfonyl)-piperazine-2-carboxamide mp 186° C. (decomp); $^1H$ NMR (DMSO-d6): δ9.05 (brs, 1H), 7.9–7.7 (m, 4H), 7.57 (dd, J=2, 6.6 Hz, 2H), 7.24 (dd, J=2, 6.6 Hz, 2H), 7.15 (d, J=6.6, 2H), 4.47 (s, 1H), 3.85 (d, J=12 Hz, 1H), 3.77 (s, 3H), 3.75–3.35 (m, 3H), 2.45 (dd, J=4.4, 12.5 Hz, 1H), 2.25–2.16 (m, 1H). Anal. calc. for $C_{21}H_{22}N_5O_7S_2Cl.0.5H_2O$: C, 44.64; H, 4.10; N, 12.40; S, 11.35. Found: C, 44.57; H, 4.08; N, 12.39; S, 11.37.

The following compounds can be prepared in a similar manner:

(e) 2(R)-N-hydroxy-1-(4-(pyrid-4-yl) oxybenzenesulfonyl)-4-(methanesulfonyl)-piperazine-2-carboxamide (f) 2(R)-N-hydroxy-1-(4-(4-(pyrazol-3-yl)phenoxy) benzenesulfonyl)-4-(methanesulfonyl)-piperazine-2-carboxamide; and (g) 2(R)-N-hydroxy-1-(4-(4-(imidazol-2-yl) phenoxy)benzenesulfonyl)-4-(methanesulfonyl)-piperazine-2-carboxamide

EXAMPLE 13

(a) 3(R/S)-N-hydroxy-4-(4-bromophenoxybenzenesulfonyl)-tetrahydro-2H-1,4-thiazine-3-carboxamide Step 1. To a solution of t-butyl-1,2-dibromopropionate (*J.C.S. Perkin I*, p. 1321 (1973); 10.85 g, 37.7 mmol) in chloroform (28 mL) and benzene (20 mL) was added a hot solution of 2-mercaptoethylamine (2.9 g, 37.7 mmol) in chloroform, benzene and triethylamine (11 mL, 79 mmol). This mixture was stirred for 3 days after which it was washed with water and brine. The organic phase was dried ($Na_2SO_4$), evaporated, and the remaining oil chromatographed on silica (1:1 ethyl acetate/hexane) to give tert-butyl 3(R/S)-tetrahydro-2H-1,4-thiazine-3-carboxylate.

Anal. calc. for $C_9H_{17}NO_2S$: C, 53.17; H, 8.43; N, 6.89; S, 15.77; Found: C, 53.30; H, 8.41; N, 6.96; S, 15.85.

Step 2. A solution of tert-butyl tetrahydro-2H-1,4-thiazine-3-carboxylate (1.02 g, 5 mmol), 4-(4-bromophenoxy)benzenesulfonyl chloride (1.58 g, 5 mmol), and triethylamine (0.84 mL, 6 mmol) in methylene chloride (10 mL) was stirred at room temperature for 20 hours after which it was diluted with methylene chloride and washed with 3 N HCl. The organic phase was dried ($Na_2SO_4$) and the solvent evaporated. The remaining orange residue was purified by silica gel chromatography (25% ethyl acetate/hexane) to give t-butyl 3(R/S)-4-(4-(4-bromophenoxy)benzenesulfonyl)-tetrahydro-2H-1,4-thiazine-3-carboxylate.

Anal. calc. for $C_{21}H_{24}NO_5S_2Br$: C, 49.03; H, 4.70; N, 2.72; Br, 15.53;
Found: C, 48.94; H, 4.67; N, 2.76; Br, 15.62.

Step 3. A solution of t-butyl 3(R/S)-4-(4-(4-bromophenoxy)benzene-sulfonyl)-tetrahydro-2H-1,4-thiazine-3-carboxylate (0.5 g, 0.97 mmol) and trifluoroacetic acid (0.5 mL) in methylene chloride (11 mL) was stirred at room temperature for 1 hour, after which it was concentrated to give 3(R/S)-4-(4-(4-bromophenoxy)benzenesulfonyl-tetrahydro-2H-1,4-thiazine-3-carboxylic acid, which was used in the next step without further purification.

Step 4. To a solution of 3(R/S)-4-(4-(4-bromophenoxy)benzenesulfonyl)-tetrahydro-2H-1,4-thiazine-3-carboxylic acid (0.62 g, 1.4 mmol) and O-t-butyldimethylsilyl hydroxylamine (0.27 g, 1.8 mmol) in 6 ml of 5:1 dichloromethane:DMF at 0° C. was added EDC (0.52 g, 2.6 mmol). The mixture was stirred at 0° C. for 30 minutes and at room temperature for 22 hours and then partitioned between ethyl acetate and water. The organic phase was washed with brine, dried ($Na_2SO_4$), and concentrated. Purification of the residue by chromatography provided 3(R/S)-N-(t-butyldimethylsilyl)oxy-4-(4-(4-bromophenoxy)-benzenesulfonyl)-tetrahydro-2H-1,4-thiazine-3-carboxamide.

Step 5. A solution of 3(R/S)-N-(t-butyldimethylsilyl)oxy-4-(4-(4-bromophenoxy)benzenesulfonyl)-tetrahydro-2H-1,4-thiazine-3-carboxamide (0.3 g, 0.51 mmol), trifluoroacetic acid (2.5 ml), and methanol (5.5 mL) in methylene chloride (10 mL) was stirred at room temperature for 1 hour. The solvents were evaporated to leave a solid residue which was washed onto filter paper with ether to give 3(R/S)-N-hydroxy-4-(4-(4-bromophenoxy)benzenesulfonyl-tetrahydro-2H-1,4-thiazine-3-carboxamide.

Anal. calc. for $C_{17}H_{17}N_2O_5Br$: C, 43.14; H, 3.62; N, 5.92; S, 13.55; Found: C, 43.21; H, 3.66; N, 5.83; S, 13.45.

The following compounds were prepared in a similar manner:

(b) 3(R/S)-N-hydroxy-4-(4-phenoxybenzenesulfonyl)-tetrahydro-2H-1,4-thiazine-3-carboxamide Anal. calc. for $C_{17}H_{18}N_2O_5S_2$: C, 51.76; H, 4.60; N, 7.10; S, 16.26; Found: C, 51.81; H, 4.56; N, 7.17; S, 16.18; and (c) 3(R/S)-N-hydroxy-4-(4-(4-fluorophenoxy)benzenesulfonyl)-tetrahydro-2H-1,4-thiazine-3-carboxamide Anal. calc. for $C_{17}H_{17}N_2O_5Br$: C, 49.50; H, 4.15; N, 6.79; S, 15.55; Found: C, 49.40; H, 4.12; N, 6.72; S. 15.48.

EXAMPLE 14

(a) 1(R/S),3(R/S)-N-hydroxy-1-oxo-4-(4-(4-bromophenoxy)benzene-sulfonyl)-tetrahydro-2H-1,4-thiazine-3-carboxamide Step 1. A solution of t-butyl 3(R/S)-4-(4-(4-bromophenoxy)benzenesulfonyl)-tetrahydro-2H-1,4-thiazine-3-carboxylate (0.3 g, 0.38 mmol) and sodium perborate (0.11 g, 0.73 mmol) in acetic acid (3 mL) was stirred at 35° C. for 5 hours, after which it was quenched with saturated aqueous sodium bicarbonate and extracted with ethyl acetate. The organic layer was dried ($Na_2SO_4$) and concentrated to give a foam which was purified by silica gel chromatography (ethyl acetate) to give t-butyl 1(R/S),3(R/S)-4-(4-(4-bromophenoxy)-benzenesulfonyl)-1-oxo-tetrahydro-2H-1,4-thiazine-3-carboxylate: MS (FAB) found 530 $(M+H)^+$.

Step 2. To a solution of t-butyl 1(R/S),3(R/S)-4-(4-(4-bromophenoxy)-benzenesulfonyl)-1-oxo-tetrahydro-2H-1,4-thiazine-3-carboxylate (0.18 g, 0.34 mmol) in methylene chloride (4 mL) was added 1.8 mL of of trifluoroacetic acid. After 4 hours, the solution was concentrated to give 1(R/S),3(R/S)-4-(4-(4-bromophenoxy)benzenesulfonyl)-1-oxo-tetrahydro-2H-1,4-thiazine-3-carboxylic acid, which was used without further purification.

Step 3. To a solution of 1(R/S),3(R/S)-4-(4-(4-bromophenoxy)benzene-sulfonyl)-1-oxo-tetrahydro-2H-1,4-thiazine-3-carboxylic acid (0.08 g, 0.17 mmol) and O-t-butyldimethylsilyl hydroxylamine (0.037 g, 0.25 mmol) in 6:1 dichloromethane:DMF (3.5 mL) at 0-C. was added EDC (0.06 g, 0.34 mmol). The mixture was stirred at 0° C. for 30 minutes followed by room temperature for 3.5 hours and then partitioned between ethyl acetate and water. The organic phase was washed with brine, dried ($Na_2SO_4$) and concentrated. The residue was purified by chromatography (ethyl acetate) to give 1(R/S),3(R/S)-N-(t-butyl-dimethylsilyl)-oxy-1-oxo-4-(4-(4-bromophenoxy)benzenesulfonyl)-tetrahydro-2H-1,4-thiazine-3-carboxamide.

Step 4. A solution of 1(R/S),3(R/S)-N-(t-butyldimethylsilyl)oxy-1-oxo-4-(4-(4-bromophenoxy)benzenesulfonyl)-tetrahydro-2H-1,4-thiazine-3-carboxamide (0.069 g, 0.11 mmol) and trifluoroacetic acid (0.5 ml) in 2 mL of 1:1 methanol:methylene chloride was stirred at room temperature for 1 hour. The solvents were evaporated to leave a solid residue which was washed onto filter paper with ether and hexane to give 1(R/S),3(R/S)-N-hydroxy-1-oxo-4-(4-(4-bromophenoxy)benzenesulfonyl)-tetrahydro-2H-1,4-thiazine-3-carboxamide.

Anal. calc. for $C_{17}H_{17}N_2O_6S_2Br$: C, 41.72; H, 3.50; N, 5.72; S, 13.10; Br, 16.33;
Found: C, 41.81; H, 3.46; N, 5.65; S, 13.01; Br, 16.44.

The following compound was prepared in a similar manner:

(b) 1(R/S),3(R/S)-N-hydroxy-1-oxo-4-(4-(4-fluorophenoxy)benzene-sulfonyl)-tetrahydro-2H-1,4-thiazine-3-carboxamide Anal. calc. for $C_{17}N_2O_6S_2F$: C, 47.66; H, 4.00; N, 6.54; S, 14.97; Found: C, 47.70; H, 4.09; N, 6.45; S, 14.86.

EXAMPLE 15

(a) 6(R)-(N-hydroxycarbamoyl)-1-(4-phenoxy)benzenesulfonyl-tetrahydropyrimidin-4-one Step 1. To a solution of D-asparagine (15.0 g) in 400 mL of water at 45° C. was added 8.25 mL of 37% formalin. After 1 hour at 45° C., the solution was cooled to −5° C. to give a slurry. The slurry was allowed to warm to 0° C., and the precipitate collected by filtration to give, following drying in vacuo, 2.26 g of 6(R)-carboxy-tetra-hydropyrimidin-4-one as a white crystalline solid: $^1$H NMR (D$_2$O, 300 MHz) δ4.70 and 4.58 (AB quartet, 2H, J=11 Hz), 4.22 (dd, 1H, J=6 and 9 Hz), 3.04 (dd, 1H, J=6 and 16 Hz), 2.82 (dd, 1H, J=9 and 16 Hz).

Step 2. To a solution of 6(R)-carboxy-tetrahydropyrimidin-4-one in 8 mL of water and 4 mL of dioxane was added 1.5 mL of N-methyl-morpholine, followed by a solution of 4-phenoxybenzenesulfonyl chloride (1.88 g) in 4 mL of dioxane. The mixture was stirred for 6 hours and then poured into pH 4.0 citrate buffer and extracted with ethyl acetate (2×50 mL). The organic layer was dried over sodium sulfate and concentrated, and the residue chromatographed (15% methanol in dichloromethane containing 1% acetic acid) to give R-carboxy-1-(4-phenoxy) benzenesulfonyl-tetrahydropyrimidin-4-one as a white solid: $^1$H NMR (D$_2$O, 300 MHz) δ7.86 (d, 2H, J=9 Hz), 7.48 (t, 2H, J=8 Hz), 7.29 (t, 1H, J=7 Hz), 7.11–7.18 (m, 4H), 5.03 (d, 1H, J=14 Hz), 4.68 (d, 1H, J=14 Hz), 4.31 (t, 1H, J=7 Hz), 2.68 (dd, 1H, J=17 and 7 Hz), 2.47 (dd, 1H, J=17 and 8 Hz).

Step 3. To a solution of 215 mg of 6(R)-carboxy-1-(4-phenoxy)benzenesulfonyl-tetrahydro-pyrimidin-4-one in 5.5 mL of 10:1 dichloromethane:DMF was added O-(t-butyldimethylsilyl)hydroxylamine (126 mg) followed by EDC hydrochloride (131 mg). After 4 hours, the reaction was partitioned between 1:1 ethyl acetate:hexane and aqueous sodium bicarbonate. The organic layer was dried over sodium sulfate, concentrated, and the residue was rapidly chromatographed with 20% ethyl acetate in dichloromethane to give 6(R)-(N-(t-butyldimethylsilyl) oxycarbamoyl)-1-(4-phenoxy)benzenesulfonyl-tetrahydropyrimidin-4-one as a solid, which, without further purification, was dissolved in 5 mL of methanol and 0.2 mL of trifluoroacetic acid. After 1 hour, 5 mL of toluene was added and the solution was concentrated. The residue was purified by rotary chromatography (65:20:15 dichloromethane:ethyl acetate:ethanol containing 0.5% acetic acid) to give 6(R)-(N-hydroxycarbamoyl)-1-(4-phenoxy) benzenesulfonyl-tetrahydropyrimidin-4-one (31 mg) as a white solid: $^1$H NMR (methanol-d$_4$, 300 MHz)_7.90 (d, 2H, J=9 Hz), 7.47 (t, 2H, J=8.7 Hz), 7.27 (t, 1H, J=7 Hz), 7.09–7.16 (m, 4H), 5.02 (d, 1H, J=14 Hz), 4.80 (d, 1H, J=14 Hz), 4.37 (t, 1H, J=7Hz), 2.77 (dd, 1H, J=17 and 7 Hz), 2.72 (dd, 1H, J=17 and 8 Hz).

The following compound was prepared in a similar manner:

(b) 6(R)-(N-hydroxycarbamoyl)-1-(4-(4-fluorophenoxy)benzene-sulfonyl)-tetrahydropyrimidin-4-one Anal. calc. for C$_{17}$H$_{16}$FN$_3$O$_6$S: C, 49.87; H, 3.94; N, 10.26; S, 7.83; Found: C, 49.84; H, 3.95; N, 10.18; S, 7.73;

The following compounds can be prepared in a similar manner:

(c) 6(R)-(N-hydroxycarbamoyl)-1-(4-(4-chlorophenoxy)benzene-sulfonyl)-tetrahydropyrimidin-4-one (d) 6(R)-(N-hydroxycarbamoyl)-1-(4-(4-methoxyphenoxy)benzene-sulfonyl)-tetrahydropyrimidin-4-one; and (e) 6(R)-(N-hydroxycarbamoyl)-1-(4-(4-(fur-2-yl) phenoxy)-benzenesulfonyl)-tetrahydropyrimidin-4-one

EXAMPLE 16

(a) 3(S)-N-hydroxy-4-(4-(4-bromophenoxy) benzenesulfonyl)-2,2-dimethyl-tetrahydro-2H-1,4-thiazine-3-carboxamide Step 1. A suspension of D-penicillamine (0.5 g, 3.35 mmol) in methanol was cooled to 0° C. and powdered sodium hydroxide (0.28 g, 7.04 mmol) was added in one portion to give a colorless solution. 2-Bromo-ethanol (0.24 mL, 3.35 mmol) was added and the reaction mixture stirred at 0° C. for 25 minutes and room temperature for an additional 80 minutes. The solvent was evaporated and the solid residue was treated with water, brought to pH 3 with 6N HCl and reconcentrated. The resulting oily residue was dissolved in water (6 mL) and stirred with DMF, sodium carbonate (1.17 g, 11.04 mmol) and 4-(4-bromophenoxy) benzenesulfonyl chloride (1.28 g, 3.68 mmol) for 17 hours. The solution was diluted with water and washed with ethyl acetate. The aqueous layer was acidified to pH 1.5 with concentrated HCl and extracted with ethyl acetate. The organic extracts were combined, washed with water and brine and dried. The solution was filtered, evaporated and azeotroped from benzene to give the crude acid as a viscous oil (0.807 g; 48% yield).

Step 2. A portion of this oil was dissolved in DMA (3 mL), treated with potassium carbonate (2.4 g, 17.5 mmol), benzyltriethylammonium chloride (0.15 g, 0.67 mmol) and t-butyl bromide (3.7 mL, 32 mmol). The reaction mixture was stirred vigorously for 18.5 hours at 55° C., after which it was diluted with ethyl acetate, washed with water, dried and evaporated to give a viscous oil which was purified by silica gel chromatography (50% ethyl acetate:hexane) to give 2(S)-3-(2-hydroxyethylsulfanyl)-3-methyl-2-(4-(4-bromophenoxy)-benzenesulfonylamino)-butyric acid tert-butyl ester as a colorless, viscous glass.

Anal. calc. for C$_{23}$H$_{30}$NO$_6$S$_2$Br: C, 49.28; H, 5.39; N, 2.50; S, 11.44; Br, 14.25;

Found: C, 49.21; H, 5.25; N, 2.46; S, 11.37; Br, 14.31.

Step 3. To a solution of 2(S)-3-(2-hydroxyethylsulfanyl)-3-methyl-2-(4-(4-bromophenoxy)benzenesulfonylamino)-butyric acid tert-butyl ester (0.17 g, 0.30 mmol) in THF (5 mL) was added triphenylphosphine (0.102 g, 0.39 mmol) and diethylazodicarboxylate (0.61 mL, 0.39 mmol). After stirring at room temperature for 20 minutes, the solvent was evaporated and the product purified on silica gel (40% ethyl acetate:hexane) to give tert-butyl 3(S)-4-(4-(4-bromophenoxy)-benzenesulfonyl)-2,2-dimethyl-tetrahydro-2H-1,4-thiazine-3-carboxylate as a light yellow oil.

Anal. calc. for C$_{23}$H$_{28}$NO$_5$S$_2$Br: C, 50.92; H, 5.20; N, 2.50; S, 11.82;

Found: C, 51.03; H, 5.18; N, 2.95; S, 11.33.

Step 4. A solution of tert-butyl 3(S)-4-(4-(4-bromophenoxy)-benzenesulfonyl)-2,2-dimethyl-tetrahydro-2H-1,4-thiazine-3-carboxylate (0.12 g, 0.22 mmol) in dichloromethane (2 mL) and TFA (1 mL) was stirred at room temperature for 50 minutes, after which the solvents were evaporated and the residue azeotroped from benzene to give 3(S)-4-(4-(4-bromophenoxy)benzenesulfonyl)-2,2-dimethyl-tetrahydro-2H-1,4-thiazine-3-carboxylic acid as a white solid, which was next used without further purification.

Step 5. A solution of 3(S)-4-(4-(4-bromophenoxy) benzenesulfonyl)-2,2-dimethyl-tetrahydro-2H-1,4-thiazine-3-carboxylic acid (0.11 g, 0.22 mmol), O-t-butyldimethlsilyl hydroxylamine (0.049 g, 0.33 mmol) and EDC (0.085 g, 0.44 mmol) in dichloromethane (2 mL) was stirred at room temperature for 30 minutes, after which the reaction mixture was diluted with dichloromethane (30 mL), washed with 5% citric acid and saturated sodium bicarbonate, dried and evaporated to give crude 3(S)-N-(t-butyldimethylsilyl)oxy-4-(4-(4-bromophenoxy)-benzenesulfonyl)-2,2-dimethyl-tetrahydro-2H-1,4-thiazine-3-carboxamide, which was next used without further purification.

Step 6. A solution of 3(S)-N-(t-butyldimethylsilyl)oxy-4-(4-(4-bromophenoxy)benzenesulfonyl)-2,2-dimethyl-tetrahydro-2H-1,4-thiazine-3-carboxamide (0.12 g, 0.19 mmol) and trifluoroacetic acid (2 mL) in dichloromethane (2 mL) was stirred at room temperature for 1 hour, after which the solvents were evaporated and the residue was azeotroped from benzene. The product was triturated with diethyl ether, filtered and washed with diethyl ether to give 3(S)-N-hydroxy-4-(4-(4-bromophenoxy)benzensulfonyl)-2,2-dimethyl-tetrahydro-2H-1,4-thiazine-3-carboxamide.

Anal. calc. for $C_{19}H_{21}N_2O_5S_2Br$: C, 45.51; H, 4.22; N, 5.59; S, 12.79; Br, 15.94;

Found: C, 45.31; H, 4.17; N, 5.50; S, 12.69; Br, 16.09.

The following compound can be prepared in a similar manner:

(b) 3(S)-N-hydroxy-2,2-dimethyl-4-(4-(4-fluorophenoxy)benzene-sulfonyl)-tetrahydro-2H-1,4-thiazine-3-carboxamide

EXAMPLE 17

(a) 1(R),3(S)-N-hydroxy-4-(4-(4-bromophenoxy)benzenesulfonyl)-2,2-dimethyl-1-oxo-tetrahydro-2H-1,4-thiazine-3-carboxamide Step 1. A solution of t-butyl 3(S)-4-(4-(4-bromophenoxy)benzene-sulfonyl)-2,2-dimethyl-tetrahydro-2H-1,4-thiazine-3-carboxylate (0.65 g, 1.2 mmol) in acetic acid (2 mL) was treated with $NaBO_3.4H_2O$ (0.23 g, 1.5 mmol) and stirred at room temperature for 2 hours, after which the reaction mixture was diluted with ethyl acetate, washed with water and saturated sodium bicarbonate, dried over sodium sulfate and evaporated. The foamy residue was twice chromatographed on silica gel (20% hexane:ethyl acetate) to give t-butyl 1(R),3(S)-4-(4-(4-bromophenoxy)benzenesulfonyl)-2,2-dimethyl-1-oxo-tetrahydro-2H-1,4-thiazine-3-carboxylate as a white foam.

Anal. calc. for $C_{23}H_{28}NO_6S_2Br$: C, 49.46; H, 5.05; N, 2.51; S, 11.48; Br, 14.31;

Found: C, 49.44; H, 5.11; N, 2.53; S, 11.55; Br, 14.21.

Step 2. A solution of t-butyl 1(R),3(S)-4-(4-(4-bromophenoxy)benzenesulfonyl)-2,2-dimethyl-1-oxo-tetrahydro-2H-1,4-thiazine-3-carboxylate (0.37 g, 0.66 mmol) in dichloromethane (4 mL) and TFA (4 mL) was stirred at room temperature for 7 hours, after which the solvents were evaporated and the residue azeotroped from benzene. The product was triturated with a warm 50% diethyl ether:hexane solution and filtered to give 1(R),3(S)-4-(4-(4-bromophenoxy)benzenesulfonyl)-2,2-dimethyl-1-oxo-tetrahydro-2H-1,4-thiazine-3-carboxylic acid as a white solid.

Anal. calc. for $C_{19}H_{20}NO_6S_2Br$: C, 45.42; H, 4.01; N, 2.79; S, 12.76; Br, 15.90;

Found: C, 45.51; H, 4.08; N, 2.84; S, 12.66; Br, 15.83.

Step 3. A solution of 1(R),3(S)-4-(4-(4-bromophenoxy)benzenesulfony1-2,2-dimethyl-1-oxo-tetrahydro-2H-1,4-thiazine-3-carboxylic acid (0.32 g, 0.64 mmol) in dichloromethane (3 mL) and DMF (1 mL) was cooled to 0° C. and treated with O-t-butyldimethylsilyl hydroxylamine (0.11 g, 0.76 mmol) immediately followed by EDC (0.183 g, 0.96 mmol). The resulting reaction mixture was stirred at 0° C. for 80 minutes, after which additional O-t-butyldimethylsilyl hydroxylamine (0.094 g, 0.64 mmol) and EDC (0.15 g, 0.76 mmol) were added, and the mixture was stirred at 0° C. for an additional hour and at room temperature for 1 hour. The reaction mixture was diluted with ethyl acetate and washed with 5% citric acid, water and saturated sodium bicarbonate, to give 1(R),3(S)-N-(t-butyldimethylsilyl)oxy-4-(4-(4-bromophenoxy)benzenesulfonyl)-2,2-dimethyl-1-oxo-tetrahydro-2H-1,4-thiazine-3-carboxamide, which was next used without further purification.

Step 4. A solution of 1(R),3(S)-N-(t-butyldimethylsilyl)oxy-4-(4-(4-bromophenoxy)benzenesulfonyl)-2,2-dimethyl-1-oxo-tetrahydro-2H-1,4-thiazine-3-carboxylic acid O-t-butyldimethylsilyl hydroxamide (0.13 g, 0.21 mmol) in dichloromethane (2 mL) and TFA (1 mL) was stirred at room temperature for 2 hours, after which the solvents were evaporated and the residue was azeotroped from benzene. The resulting white solid was filtered and washed with diethyl ether to give 1(R),3(S)-N-hydroxy-4-(4-(4-bromophenoxy)-benzenesulfonyl)-2,2-dimethyl-1-oxo-tetrahydro-2H-1,4-thiazine-3-carboxamide.

Anal. calc. for $C_{19}H_{21}N_2O_6S_2Br$: C, 44.10; H, 4.09; N, 5.41; S, 12.39;

Found: C, 43.84; H, 4.20; N, 5.37; S, 12.25.

The following compound can be prepared in a similar manner:

(b) 1(R),3(S)-N-hydroxy-1-oxo-2,2-dimethyl-4-(4-(4-fluorophenoxy) benzenesulfonyl)-tetrahydro-2H-1,4-thiazine-3-carboxamide

EXAMPLE 18

(a) 3(S)-N-hydroxy-4-(4-((pyrid-4-yl)oxy)benzenesulfonyl)-2,2-dimethyl-tetrahydro-2H-1,4-thiazine-3-carboxamide Step 1. To a stirred solution of D-penicillamine in 20 mL of dry DMF was added diisopropylethylamine (1.74 mL) followed by, in a dropwise manner, trimethylsilyl chloride (1.52 mL). After 30 minutes, diazabicyclo[4.2.0]undecane (4.48 mL) was added to the clear solution, and the resulting solution was slowly transferred via cannula over a 1 hour period to a solution of 1,2-dibromoethane (0.95 mL) in 20 mL of dry DMF at 50° C. After the addition was complete, the solution was heated for an additional 1 hour at 50° C., and then cooled to 0° C. To the stirred solution was added N-methylmorpholine (1.00 mL), followed by 9-fluorenylmethoxycarbonyl chloride (2.84 g), and the solution was kept at −20° C. for 16 hours. An additional 0.50 g of 9-fluorenylmethoxycarbonyl chloride was added, and the solution was stirred for an additional 1 hour at 0° C. and then quenched with 1 mL of water. The reaction was partitioned between 3:1 ethyl acetate:hexane (200 mL) and 0.2 N aqueous sodium bisulfate (200 mL). The organic layer was washed with additional 0.2 N aqueous sodium bisulfate solution (150 mL) and with brine (50 mL), dried over sodium sulfate and concentrated. The residue was purified by chromatography on 150 g of silica gel, eluting with 25% to 35% ethyl acetate:hexane containing 0.5% acetic acid. The product-containing fractions were concentrated to give a syrup, which was twice concentrated from toluene, and finally from t-butyl methyl ether:isooctane, to give 2.84 g of 3(S)-4-(9-fluorenylmethoxy-carbonyl)-2,2-dimethyl-tetrahydro-2H-1,4-thiazine-3-carboxylic acid as a white solid.

Step 2. To a solution of 3(S)-4-(9-fluorenylmethoxycarbonyl)-2,2-dimethyl-tetrahydro-2H-1,4-thiazine-3-carboxylic acid (2.98 g) in 20 mL of dichloromethane at 0° C. was added O-(t-butyldiphenyl-silyl)

hydroxylamine (2.71 g) followed by EDC hydrochloride (1.58 g). The reaction was stirred at 0° C. to 25° C. for 16 hours and then partitioned between 1:1 ethyl acetate:hexane (200 mL) and 0.2 N pH 7 phosphate buffer (100 mL). The organic layer was washed with brine, dried over sodium sulfate and concentrated. The residue was purified by chromatography on 150 g of silica gel, eluting with 20% to 30% ethyl acetate:hexane, to provide, after concentration from dichloromethane:isooctane, 3(S)-N-(t-butyldiphenylsilyl)oxy-4-(9-fluorenylmethoxycarbonyl)-2,2-dimethyl-tetrahydro-2H-1,4-thiazine-3-carboxamide (4.42 g) as a white solid.

Step 3. To a solution of 3(S)-N-(t-butyldiphenylsilyl)oxy-4-(9-fluorenylmethoxycarbonyl)-2,2-dimethyl-tetrahydro-2H-1,4-thiazine-3-carboxamide (4.33 g) in THF (10 mL) was added diethylamine (5 mL). After 1 hour, the solution was concentrated and the residue was chromatographed on 75 g of silica gel, eluting with ethyl acetate, to give 3(S)-N-(t-butyldiphenylsilyl)oxy-2,2-dimethyl-tetrahydro-2H-1,4-thiazine-3-carboxamide (2.11 g) as a sticky solid foam.

Step 4. To a solution of 4-phenoxypyridine (6.84 g) in 20 mL of 1,2-dichloroethane at 0° C. was added 8.0 mL of chlorosulfonic acid in a dropwise manner. After 10 minutes, the ice bath was removed and the solution was allowed to warm to 25° C. After an additional 1 hour, the solution was heated to 40° C. for 3 hours, and then cooled to 25° C., and oxalyl chloride (4.4 mL) was added. The solution was heated to 50° C. for 16 hours, and then an additional 2.2 mL of oxalyl chloride was added. After 5 hours more at 5° C., the solution was cooled to 25° C., and poured with rapid stirring into 250 mL of diethyl ether. After 1 minute, the solids were allowed to settle and the supernatant was decanted. The residue was suspended in 3:1 toluene:dichloromethane (250 mL) at about 5° C. and 50 mL of 1.6 M aqueous $K_3PO_4$ was added with stirring. After about 30 seconds, the mixture was transferred to a separatory funnel and the layers were separated. The organic layer was washed with 25 mL of 1 N pH 7 phosphate buffer and with 10 mL of brine, and the combined aqueous layers were extracted with 50 mL of toluene. The combined organic layers were dried over sodium sulfate then filtered through a glass-fiber filter. To the filtrate was immediately added 11 mL of 4 M HCl in dioxane and the solution was then concentrated. Partial concentration from dichloromethane:t-butyl methyl ether and filtration gave 2.11 g of 4-((pyrid-4-yl)oxy)benzenesulfonyl chloride hydrochloride.

Step 5. To a solution of 3(S)-N-(t-butyldiphenylsilyl)oxy-2,2-dimethyl-tetrahydro-2H-1,4-thiazine-3-carboxamide (2.11 g) in dichloromethane (20 mL) at 0° C. was added N-methylmorpholine (1.35 mL) followed by 4-((pyrid4-yl)oxy)benzenesulfonyl chloride hydrochloride (1.71 g). The solution was stirred at 0° C. for 3 hours, and then at 25° C. for 4 hours. The reaction was partitioned between 3:1 ethyl acetate:hexane (150 mL) and 0.5 N pH 7 phosphate buffer (50 mL). The organic layer was washed with additional buffer and with brine, dried over sodium sulfate and concentrated. The residue was chromatographed on 150 g of silica gel, eluting with 30% to 50% ethyl acetate:dichloromethane to give, after partial concentration from dichloromethane:isooctane, 3(S)-N-(t-butyldiphenylsilyl)oxy-4-(4-((pyrid4-yl)oxy)benzenesulfonyl)-2,2-dimethyl-tetrahydro-2H-1,4-thiazine-3-carboxamide (2.36 g) as a pale yellow solid.

Step 6. To a solution of 3(S)-N-(t-butyldiphenylsilyl)oxy-4-(4-((pyrid4-yl)oxy)benzenesulfonyl)-2,2-dimethyl-tetrahydro-2H-1,4-thiazine-3-carboxamide (2.25 g) in methanol (10 mL) was added 5 mL of a 10% solution of concentrated HCl in methanol. After 1 hour at 25° C., the solution was diluted with methanol (50 mL) and treated with Amberlite IRA-68 weakly basic resin (about 15 mL) until the pH measured 7.2. The resin was removed by filtration and washed well with methanol, and then the filtrate was concentrated to about 10 mL. Addition of 20 mL of t-butyl methyl ether gave a voluminous precipitate, which was collected by filtration to give 1.19 g of an off-white solid. The solid was dissolved in 50 mL of 10% methanol in ethyl acetate and filtered through a 0.45 µm syringe filter to remove trace particles. The filtrate was partially concentrated to about 20 mL, diluted with additional ethyl acetate and reconcentrated to about 20 mL. The crystalline precipitate was collected by filtration and dried in vacuo to give 3(S)-N-hydroxy-4-(4-((pyrid-4-yl)oxy)benzenesulfonyl)-2,2-dimethyl-tetrahydro-2H-1,4-thiazine-3-carboxamide (0.97 g) as a white solid: mp 149.8° C.

Anal. calc. for $C_{18}H_{21}N_3O_5S_2.0.5\ H_2O$: C, 49.47; H, 5.19; N, 9.62; S, 14.62;

Found: C, 49.49; H, 5.15; N, 9.37; S, 14.41.

The following compound was prepared in a similar manner:

(b) 3(S)-N-hydroxy-4-(4-((pyrid-2-yl)oxy)benzenesulfonyl)-2,2-dimethyl-tetrahydro-2H-1,4-thiazine-3-carboxamide HRMS (FAB) calc. for $(M+Cs)^+$: 556.9977; found: 556.9963.

Anal. calc. for $C_{18}H_{21}N_3O_5S2.0.75\ H_2O$: C, 49.47; H, 5.19; N, 9.62; S, 14.67;

Found: C, 49.22; H, 4.81; N, 9.57; S, 14.69;

The following compound can be prepared in a similar manner:

(c) 3(S)-N-hydroxy-4-(4-(4-(imidazol-2-yl)phenoxy)benzenesulfonyl)-2,2-dimethyl-tetrahydro-2H-1,4-thiazine-3-carboxamide

EXAMPLE 19

(a) 1(S), 3(S)-N-hydroxy-4-(4-((pyrid-4-yl)oxy)benzenesulfonyl)-2,2-dimethyl-1-oxotetrahydro-2H-1,4-thiazine-3-carboxamide and 1(R), 3(S)-N-hydroxy-4-(4-((pyrid-4-yl)oxy)benzenesulfonyl)-2,2-dimethyl-1-oxotetrahydro-2H-1,4-thiazine-3-carboxamide To a solution of 3(S)-N-hydroxy-4-(4-((pyrid-4-yl)oxy)benzenesulfonyl)-2,2-dimethyl-tetrahydro-2H-1,4-thiazine-3-carboxamide (0.423 g, 1.00 mmol) in 30 mL of 5:1 dichloromethane:methanol at −10° C. was added 0.15 g (0.85 mmol) of m-chloroperbenzoic acid in portions over a 2 hour period. The solution was diluted with 60 mL of methanol and then passed through 10 mL of Amberlite IRA-68 weakly basic resin to remove the byproduct m-chlorobenzoic acid. The filtrate was concentrated and the residue was chromatographed with 6% to 12% methanol in dichloromethane. Eluting first was 1(S), 3(S)-N-hydroxy-4-(4-((pyrid-4-yl)oxy)benzenesulfonyl)-2,2-dimethyl-1-oxotetrahydro-2H-1,4-thiazine-3-carboxamide (200 mg): $^1$H NMR (300 MHz, DMSO-$d_6$): δ10.92 (s, 1H), 9.04 (s, 1H), 8.57 (m, 2H), 7.90 (d, J=8.5 Hz, 2H), 7.39 (d, J=8.5 Hz, 2H), 7.12 (d, J=4.5 Hz, 2H), 4.39 (s, 1H), 4.33–4.20 (m, 1H), 3.94–3.86 (m, 1H), 3.21–3.10 (m, 1H), 3.02 (d, J=15 Hz, 1H), 1.42 (s, 3H), 1.25 (s, 3H);

Anal. calc. for $C_{18}H_{21}N_3O_6S_2.0.15H_2O$, 0.1EtOAc: C, 49.00; H, 4.94; N, 9.32; S, 14.22. Found: C, 48.99; H, 4.97; N, 9.27; S, 14.32.

Continued elution provided 1(R), 3(S)-N-hydroxy-4-(4-((pyrid-4-yl)oxy)benzenesulfonyl)-2,2-dimethyl-1-oxotetrahydro-2H-1,4-thiazine-3-carboxamide (50 mg): $^1$H NMR (300 MHz, DMSO-d$_6$): δ10.98 (s, 1H), 9.20 (s, 1H), 8.58 (d, J=6 Hz, 2H), 7.89 (d, J=9 Hz, 2H), 7.40 (d, J=9 Hz, 2H), 7.12 (d, J=6 Hz, 2H), 4.40 (s, 1H), 4.10–3.90 (m, 2H), 3.45–3.35 (m, 1H), 2.70–2.50 (m, 1H), 1.27 (s,3H), 1.25 (s, 3H); LSIMS: m/e expected for $C_{18}H_{21}N_3O_6S_2+H^+$=440; m/e observed=440.

Anal. calc. for $C_{18}H_{21}N_3O_6S_2 \cdot 0.2H_2O$, 0.3EtOAc: C, 49.11; H, 5.11; N, 8.95; S, 13.66. Found: C,49.21; H, 4.98; N, 8.99; S, 13.60.

The following compound was prepared in a similar manner:

(b) 1(R), 3(S)-N-hydroxy-4-(4-(4-chlorophenoxy)benzenesulfonyl)-2,2-dimethyl-1-oxo-tetrahydro-2H-1,4-thiazine-3-carboxamide mp 145–147° C. Anal. Calcd for $C_{19}H_{21}ClN_2O_6S_2 \cdot 0.8H2O$: C, 48.3; H, 4.48; N, 5.93; S, 13.55; Cl, 7.41. Found: C, 46.96; H, 4.69; N, 5.64; S, 13.01; Cl, 7.30.

EXAMPLE 20

3(S)-4-(4-(4-(furan-3-yl)phenoxy)benzenesulfonyl-N-hydroxy-tetrahydro-2H-1,4-thiazine-3-carboxamide Step 1. To a suspension of D-penicillamine (0.75 g, 5 mmol) in 10 mL of dry DMF was added 0.87 mL (5 mmol) of diisopropylethylamine, followed by 0.75 mL (6 mmol) of trimethylsilyl chloride. After twenty minutes, 1,8-diazabicyclo [5.4.0]undec-7-ene (2.24 mL, 15 mmol) was added to the homogeneous solution and the solution was transferred to an addition funnel and then added dropwise over a 1 hour period to a stirred solution of 0.50 mL (5.8 mmol) of 1,2-dibromoethane in 10 mL of DMF at 50° C. After an additional 30 minutes after the addition was complete, the solution was cooled to 0° C. and 0.55 mL (5 mmol) of N-methylmorpholine was added, followed by the dropwise addition of a solution of 4-(4-bromophenoxy)benzenesulfonyl chloride (1.94 g, 5.5 mmol) in 5 mL of DMF over a 15 minute period. The reaction was stirred for 2 hours at 0° C. and then allowed to warm to room temperature. After an additional 2 hours, 0.3 g more of 4-(4-bromophenoxy)benzenesulfonyl chloride was added. After an additional 15 minutes, the reaction was partitioned between 0.2 N aq. sodium bisulfate and 1:1 ethyl acetate:hexane. The aqueous layer was extracted twice with 1:1 ethyl acetate:hexane, and the combined organic layers were washed with 0.2 N aq. sodium bisulfate and with brine, dried over sodium sulfate, and concentrated. The residue was purified by chromatography on silica gel, eluting with a gradient from dichloromethane to 8% methanol in dichloromethane, to provide, after rotary evaporation from dichloromethane/t-butyl methyl ether, 3(S)-4-(4-(4-bromophenoxy)benzenesulfonyl-tetrahydro-2H-1,4-thiazine-3-carboxylic acid (0.84 g, 37%) as a solid foam: $^1$H NMR (CDCl$_3$): δ7.70 (d, 2H, J=9.19 Hz), 7.50 (d, 2H, J=8.82 Hz), 7.01 (d, 2H, J=8.83 Hz), 6.94 (d, 2H, J=8.82 Hz), 4.50 (s, 1H), 4.01 (d, 1H, J=13.24 Hz), 3.7–3.6 (m, 1H), 3.2–3.1 (m ,1H), 2.42 (d, 1H, J=13.98 Hz), 1.61 (s, 3H), 1.39 (s, 3H)

Step 2. A mixture of 0.45 g (1.0 mmol) of 3(S)-4-(4-(4-bromophenoxy)benzenesulfonyl-tetrahydro-2H-1,4-thiazine-3-carboxylic acid and 0.11 g (1.0 mmol) of 3-furan boronic acid (*J. Org. Chem.* 1984, 49, 5237–5243) in 2 mL of benzene, 2 mL of 2M aq. sodium carbonate, and 1.5 mL of ethanol was deoxygenated with a stream of argon for 15 minutes, and then 115 mg (0.1 mmol) of tetrakis (triphenylphosphine)palladium was added and the mixture was heated at 80° C. for six days. After cooling to room temperature, the mixture was partitioned between ethyl acetate and pH 4 citrate buffer. The aqueous layer was extracted twice with ethyl acetate, and the combined organic layers were washed with brine, dried over sodium sulfate, and concentrated. The residue was purified by chromatography on silica gel, eluting with a gradient from dichloromethane to 5% methanol in dichloromethane, to provide 3(S)-4-(4-(4-(furan-3-yl)phenoxy)benzenesulfonyl-tetrahydro-2H-1,4-thiazine-3-carboxylic acid (0.317 g, 67%) as a sticky solid foam. FAB$^+$MS Calcd for M+Cs$^+$= 606.0021. Obs 606.0036; $^1$H NMR (CDCl$_3$) δ7.72–7.43 (m, 6H), 7.04 (d, 2H, J=8.46 Hz), 7.00 (d, 2H, J=8.82 Hz), 6.67 (s, 1H), 4.51 (s, 1H), 4.1–3.9 (bm, 1H), 3.7–3.6 (bm, 1H), 3.2–3.1 (bm, 1H), 2.42 (bd, 1H, J=12.87 Hz), 1.61 (s, 3H), 1.38 (s, 3H)

Step 3. To a solution of 3(S)-4-(4-(4-(furan-3-yl)phenoxy)benzenesulfonyl-tetrahydro-2H-1,4-thiazine-3-carboxylic acid (293 mg, 0.62 mmol) and O-(tert-butyldiphenylsilyl) hydroxylamine (0.22 g, 0.8 mmol) in 5 mL of dichloromethane was added EDC (132 mg, 0.69 mmol). After 18 hours at 25° C., the mixture was partitioned between 1 N aq. sodium bisulfate and dichloromethane. The aqueous layer was extracted twice with dichloromethane, and the combined organic layers were washed with brine, dried over sodium sulfate, and concentrated. The residue was purified by chromatography on silica gel, eluting with a gradient from dichloromethane to 5% methanol in dichloromethane, to provide 3(S)-N-(tert-butyldiphenylsilyl)oxy-4-(4-(4-(furan-3-yl)phenoxy)benzenesulfonyl-tetrahydro-2H-1,4-thiazine-3-carboxamide (40 mg, 8%). FAB$^+$MS Calcd for M+Cs$^+$=859.1308 Obs 859.1274; $^1$HNMR (d$_6$-DMSO): δ10.81 (s, 1H), 8.17 (s, 1H), 7.74 (s, 1H), 7.67–7.61 (m, 8H), 7.45–7.30 (m, 6H), 7.10 (d, 2H, J=8.83 Hz), 7.00 (d, 2H, J=8.46 Hz), 6.94 (s, 1H), 4.06 (s, 1H), 3.95–3.89 (bm, 1H), 3.77–3.73 (bm, 1H), 2.87–2.78 (bm, 1H), 1.28 (s, 3H), 0.99 (s, 9H), 0.61 (s, 3H)

Step 4. To a 25° C. solution of 3(S)-N-(tert-butyldiphenylsilyl)oxy-4-(4-(4-(furan-3-yl)phenoxy)benzenesulfonyl-tetrahydro-2H-1,4-thiazine-3-carboxamide (35 mg) in 2 mL of THF was added 0.060 mL of 2M tetrabutylammonium fluoride in THF. After 30 minutes, the solution was partitioned between 1 M pH 7 phosphate buffer and ethyl acetate. The aqueous layer was extracted once with ethyl aceate, and the combined organic layers were washed with brine, dried over sodium sulfate, and concentrated. The residue was triturated with hexane and the resulting solid was collected by filtration to yield 3(S)-4-(4-(4-(furan-3-yl)phenoxy)benzenesulfonyl-N-hydroxy-tetrahydro-2H-1,4-thiazine-3-carboxamide (22 mg). $^1$H NMR (CDCl$_3$): δ9.69 (bs, 1H), 7.24 (d, 2H, J=8.82 Hz), 7.51 (d, 2H, J=8.46 Hz), 7.05 (t, 4H, J=9.37 Hz), 6.69 (s, 1H), 4.57 (s, 1H), 4.02 (d, 1H, J=12.5 Hz), 3.28–3.12 (m, 2H), 2.50 (d, 1H, J=12.87 Hz), 1.61 (s, 3H), 1.31 (s, 3H).

EXAMPLE 21

Step 1. To a stirred mixture of 2(R/S)-(tert-butoxycarbonyl)amino-3,3-dimethyl-4-pentenoic acid (3.6 g, 15 mmol) and anhydrous sodium bicarbonate (3.78 g, 45 mmol) in 25 mL of DMF was added methyl iodide (1.03 mL, 17 mmol) dropwise. The mixture was stirred for 27 hours at room temperature, and then poured into water (100 mL). The mixture was extracted with 2:1 ethyl acetate:hexane (3×50 mL), and the combined organic layers were washed with 5% aq. sodium thiosulfate solution, water, sat. aq. sodium bicarbonate, and finally with brine. The organic layer was dried over magnesium sulfate, and concentrated to provide methyl 2(R/S)-(tert-butoxycarbonyl)amino-3,3-dimethyl-4-pentenoate (3.37 g, 87%) as a syrup which was used without further purification.

Step 2. To a solution of methyl 2(R/S)-(tert-butoxycarbonyl)amino-3,3-dimethyl-4-pentenoate (4.97 g, 19.3 mmol) in 50 mL of dichloromethane at 0° C. was added 16.5 mL of trifluoroacetic acid. After 2 hours, the solution was concentrated and the residue was dissolved in 100 mL of dichloromethane and washed with sat. aq. sodium bicarbonate (50 mL). The organic layer was dried over sodium sulfate and concentrated to give methyl 2(R/S)-amino-3,3-dimethyl-4-pentenoate (2.30 g), which was dissolved in 50 mL of dichloromethane and cooled to 0° C. Triethylamine (8.1 mL, 58 mmol) was added, followed by addition of 4-(4-fluorophenoxy)benzenesulfonyl chloride (6.71 g, 21.3 mmol). The reaction was allowed to warm to room temperature and stirred for 18 hours and then washed 3 N hydrochloric acid (125 mL), dried over sodium sulfate and concentrated. The residue was purified by chromatography on silica gel, eluting with 20% ethyl acetate in hexane, to yield 4.41 g (61%) of methyl 2(R/S)-[4-(4-fluorophenoxy)benzenesulfonyl]amino-3,3-dimethyl-4-pentenoate as a white solid.

Anal. Calcd for $C_{20}H_{22}FNO_5S$: C, 58.96; H, 5.44; N, 3.44; S, 7.87. Found: C, 59.01; H, 5.47; N, 3.50; S, 7.95.

Step 3. A mixture of methyl 2(R/S)-[4-(4-fluorophenoxy)benzenesulfonyl]amino-3,3-dimethyl-4-pentenoate (4.31 g, 10.6 mmol) and potassium carbonate (3.65 g, 26.4 mmol) was stirred vigorously in 25 mL of DMF at 65° C. as ethyl bromoacetate was added dropwise. After 16 hours, an additional 1.82 g of potassium carbonate and 4.1 mL of ethyl bromoaceate was added. After an additional 3 hours at 65° C., 6.0 mL of ethyl bromoaceate was added and stirring was continued for another 4 hours. After cooling to room temperature, the solvent was removed in vacuo (~1 torr), and the residue was partitioned between ethyl acetate and water. The organic layer was washed with water and with brine, dried over sodium sulfate, and concentrated. The residue was chromatographed on silica, eluting with a gradient of 10% to 20% ethyl acetate in heaxane to provide 4.05 g (78%) of methyl 2(R/S)-[4-(4-fluorophenoxy)benzenesulfonyl][(ethoxycarbonyl)methyl]amino-3,3-dimethyl-4-pentenoate.

Anal. Calcd for $C_{24}H_{28}FNO_7S$: C, 58.42; H, 5.72; N, 2.84; S, 6.50. Found: C, 58.34; H, 5.75; N, 2.90; S, 6.40.

Step 4. To a mixture of methyl 2(R/S)-[4-(4-fluorophenoxy)benzenesulfonyl][(ethoxycarbonyl)methyl]amino-3,3-dimethyl-4-pentenoate (3.52 g, 7.13 mmol) in 40 mL of 2:2:3 carbon tetrachloride:acetonitrile:water was added 0.037 g (0.18 mmol) of ruthenium trichloride monohydrate and 7.78 g (36.4 mmol) of sodium periodate. The mixture was stirred vigorously at room temprature for 22 hours, then diluted with 150 mL of water and extracted with dichloromethane (3×50 mL). The combined organic layers were dried over sodium sulfate and concentrated. The residue was purified by chromatography on silica gel, eluting with a gradient from 1:1 ethyl acetate:hexane to ethyl acetate, to yield 2(R/S)-[4-(4-fluorophenoxy)benzenesulfonyl][(ethoxycarbonyl)methyl]amino-3,3-dimethyl-butanedioic acid, 1-methyl ester (2.27 g, 62%) as an off-white solid.

Step 5. To a solution of methyl 2(R/S)-[4-(4-fluorophenoxy)benzenesulfonyl][(ethoxycarbonyl)methyl]amino-3,3-dimethyl-butanedioic acid (2.00 g, 3.91 mmol) and triethylamine (0.6 mL, 4.30 mmol) in 50 mL of benzene at 80° C. was added diphenyylphosphoryl azide (0.93 mL, 4.3 mmol). After 4 hours, benzyl alcohol (1.62 mL, 15.6 mmol) was added. After an additional 20 hours, the reaction was cooled to room temperature and partitioned between ethyl acetate and 10% aq. citric acid. The organic layer was washed with sat. aq. sodium bicarbonate, dried over sodium sulfate, and concentrated. The excess benzyl alcohol was removed by kugelrohr distillation at 0.28 torr, 70° C., and the residue was purified by chromatography on silica, eluting with 30% ethyl acetate in hexane, to give methyl 2(R/S)-[4-(4-fluorophenoxy)benzenesulfonyl][(ethoxycarbonyl)methyl]amino-3-(benzyloxycarbonyl)amino-3-methylbutanoate (1.81 g, 75%) as a colorless, viscous oil.

Anal. Calcd for $C_{29}H_{33}FN_2O_9S$: C, 58.34; H, 5.55; N, 4.54; S, 5.19. Found: C, 58.50; H, 5.43; N, 4.60; S, 5.16.

Step 7. A solution of methyl 2(R/S)-[4-(4-fluorophenoxy)benzenesulfonyl][(ethoxycarbonyl)methyl]amino-3-(benzyloxycarbonyl)amino-3-methylbutanoate (1.89 g, 3.06 mmol) in 50 mL of ethanol was hydrogenated over 0.19 g of 10% palladium on carbon under 1 atm of hydrogen for 1 hour at room temperature. The catalyst was removed by filtration, and the filtrate was concentrated. The residue was triturated with 50 mL of warm diethyl ether and filtered to give 1.07 g (80%) of methyl 2(R/S)-1-[4-(4-fluorophenoxy)benzenesulfonyl]-3,3-dimethyl-5-oxo-piperazine-2-carboxylate as an off-white solid.

Anal. Calcd for $C_{20}H_{21}FN_2O_6S$: C, 55.04; H, 4.85; N, 6.42; S, 7.35. Found: C, 55.15; H, 4.95; N, 6.33; S, 7.20.

Step 8. A solution of methyl 2(R/S)-1-[4-(4-fluorophenoxy)benzenesulfonyl]-3,3-dimethyl-5-oxo-piperazine-2-carboxylate (0.20 g, 0.46 mmol) and 0.123 g (0.92 mmol) of lithium iodide in 8.8 mL of freshly-distilled 2,6-lutidine was heated at 120° C. After 1.25 hours at 120° C., an additional 0.123 g of lithium iodide was added. After an additional 3 hours, more lithium iodide (0.123 g) was added and the reaction was stirred for another 2 hours. After cooling to room temperature, the reaction was poured into water (75 mL) and extracted with 3×40 mL of ethyl acetate (to remove 2,6-lutidine). The aqueous layer was then acidified and extracte with ethyl acetate (2×50 mL). The combined organic layers were dried over sodium sulfate, treated with decolorizing carbon, filtered, and concentrated. The oily residue was triturated with diethyl ether (5 mL) and hexane (2 mL). The solid was collected by filtration and washed with diethyl ether to provide 121 mg (62%) of 2(R/S)-1-[4-(4-fluorophenoxy)benzenesulfonyl]-3,3-dimethyl-5-oxo-piperazine-2-carboxylic acid as a beige solid.

Anal. Calcd for $C_{19}H_{19}FN_2O_6S$: C, 54.02; H, 4.53; N, 6.63; S, 7.59. Found: C, 54.13; H, 4.59; N, 6.54; S, 7.47.

Step 9. To a stirred solution of 2(R/S)-1-[4-(4-fluorophenoxy)benzenesulfonyl]-3,3-dimethyl-5-oxo-piperazine-2-carboxylic acid (50 mg, 0.12 mmol) and N-methyl morpholine (0.10 mL) in DMF (0.5 mL) at 25° C. was added 92 mg (0.18 g) of PyBOP followed by addition of 33 mg (0.47 mmol) of hydroxylamine hydrochloride. After 22.5 hours, the reaction was partitioned between ethyl acetate and 10% aqueous citric acid, and the organic layer was washed with water, sat. aq. sodium bicarbonate, water, and brine. The organic layer was dried over sodium sulfate and concentrated, and the residue was redissolved in 20 mL of diethyl ether and partially concentrated to provide 0.23 g of a white solid which was somewhat impure accoring to TLC analysis. Purification by chromatography on silica, eluting with 0.5% acetic acid in ethyl acetate, provided 7.1 mg of 2(R/S)-1-[4-(4-fluorophenoxy)benzenesulfonyl]-3,3-dimethyl-N-hydroxy-5-oxo-piperazine-2-carboxamide: FAB HRMS calcd. for $C_{19}H_{21}FN_3O_6S$ $(M+H)^+$: 438.1135. Found: 438.1145.

Anal. Cal. for $C_{19}H_{20}N_3O_6SF.0.25H_2O$: C, 51.63; H, 4.68; N, 9.51; S, 7.26. Found: C, 51.58; H, 4.70; N, 9.42; S, 7.1.7.

EXAMPLE 22

2(R/S)-3-acetyl-1-4-(4-fluorophenoxy)benzenesulfonyl-N-hydroxy-hexahydropyrimidine-2-carboxamide Step 1. To a stirred solution of 1,3-diaminopropane (6.7 mL) in 100 mL of dichloromethane at −10° C. was slowly added over a 2 hour period a solution of 4-(4-fluorophenoxy)benzenesulfonyl chloride (5.7 g, 20 mmol) in 50 mL of dichloromethane. The reaction was stirred for 15 minutes after the addition was complete, and then partitioned between ethyl acetate and water. The resulting emulsion was cleared by addition of dichloromethane, and the organic layer was separated. The aqueous layer was extracted with dichloromethane and the combined organic layers were extracted with 0.5 N aq. sodium bisulfate. The aqueous phase was brought to pH 8 with sodium bicarbonate and then extracted with dichloromethane (3×100 mL). The combined organic layers were dried over sodium sulfate and concentrated to a volume of about 50 mL. Addition of hexane resulting in formation of a precipitate, which was collected by filtration to provide N-(3-aminopropyl)-4-(4-fluorophenoxy)benzenesulfonamide (4.27 g) as a white solid: mp 184° C. (softens), 237° C. (melts) $^1$H NMR (300 MHz, DMSO-$d_6$): δ7.84 (d, J=9 Hz, 2H), 7.38–7.21 (m, 4H), 7.12 (d, J=9 Hz, 2H), 3.6–3.2 (br s, 3H), 2.80 (dd, J=7, 7 Hz, 2H), 2.77 (dd, J=7, 7 Hz, 2H), 1.72–1.60 (m, 2H).

Step 2. To a solution of N-(3-aminopropyl)-4-(4-fluorophenoxy)benzenesulfonamide (3.24 g, 10 mmol) in 100 mL of dichloromethane was added 2.26 mL of a 50% solution of ethyl glyoxalate in toluene. After 2 hours, 10 g of 3 A molecular sieves were added. After 18 hours, an additonal 2.26 mL of ethyl glyoxalate was added portionwise while monitoring the reaction progress by TLC. After 4 hours, the reaction was filtered through Celite 545, and the filtrate was concentrated. The residue was purified by chromatography on silica, eluting first with 2:2:1 hexane:dichloromethane:ethyl acetate and then with 1:3 ethyl acetate:dichloromethane, to give 1.2 g of a mixture of two compounds by TLC analysis, which was employed without further purification in the next reaction.

Step 3. To a solution of the product (1.1 g) from the previous paragraph in 25 mL of dichloromethane was added 0.67 mL of 4 M hydrogen chloride in dioxane. After 1 hour at room temperature, the solution was cooled to −20° C., and acetyl chloride (0.19 mL) was added, followed by addition of N-methyl morpholine (0.89 mL). After 2 hours at −20 ° C. and 1.5 hours at room temprature, the reaction was partitioned between water and ethyl acetate. The organic layer was dried over sodium sulfate, concentrated, and the residue was purified by chromatography, eluting with 40% acetone in hexane, to yield ethyl 2(R/S)-3-acetyl-1-4-(4-fluorophenoxy)benzenesulfonyl-hexahydropyrimidine-2-carboxylate (0.24 g) as a clear syrup: LSI MS m/e expected for $C_{21}H_{24}FN_2O_6S$ $(M+H)^+$: 451. Found: 451.

Step 4. A solution of ethyl 2(R/S)-3-acetyl-1-4-(4-fluorophenoxy)benzenesulfonyl-hexahydropyrimidine-2-carboxylate (0.225 g) and hydroxylamine (0.10 mL of a 50% aqueous solution) in 5 mL of ethanol was stirred at 25° C. for 18 hours, and then at 55° C. for 24 hours. The reaction solution was concentrated and chromatographed, eluting first with 40% ethyl acetate in dichloromethane and then with 54:40:5:1 dichloromethane:ethyl acetate:methanol:acetic acid, to yield 37 mg (17%) of 2(R/S)-3-acetyl-1-4-(4-fluorophenoxy)benzenesulfonyl-N-hydroxy-hexahydropyrimidine-2-carboxamide as a white foam after concentration from dichloromethane/isooctane: mp 79° C.; $^1$H NMR (300 MHz, DMSO-$d_6$) δ11.0 (br s, 1H), 9.05 (br s, 1H), 7.79 (d, J=9 Hz, 2H), 7.39–7.30 (m, 2H), 7.28–7.21 (m, 2H), 7.12 (d, J=9 Hz, 2H), 6.77 (s, 1H), 3.73 (d, J=14.5 Hz, 1H), 3.58 (d, J=13 Hz, 1H), 3.33–3.13 (m, 2H), 1.93 (s, 3H), 1.44–1.35 (m, 1H), 1.17–1.07 (m, 1H); HRMS (FAB) (+Cs)+expected: 570.0111. Found 570.0122.

Anal. calc. for $C_{19}H_{20}FN_3O_6S.0.1$ $CH_2Cl_2.0.25$ isooctane: C, 52.05; H, 4.97; N, 9.06; S, 6.91. found: C, 52.03; H, 5.00; N, 9.05; S, 6.85.

Anal. calc. for $C_{21}H_{23}N_2O_6SF$/*.0.4$H_2O$, 0.3 hexane, 0.1 toluene: C, 52.72; H, 5.01; N, 9.09; S, 6.93. Found: C, 52.75; H, 4.96; N, 9.03; S, 6.78.

The results obtained during biological testing of some preferred embodiments of the inventive compounds are described below.

Biological Data

Enzyme Assays

Stromelysin enzymatic activity was measured using a modified version of a resonance energy transfer fluorogenic assay as desribed in *FEBS*, vol. 296(3), p. 263 (1992), the disclosure of which is incorporated herein by reference. The MCA-peptide substrate is shown below. The fluorescent MCA group is quenched by resonance energy transfer to the 2,4-dinitrophenyl group. Matrix metalloproteinases cleave this substrate at the Gly-Leu bond. Cleavage results in the loss of energy transfer and a large increase in fluorescence of the MCA group.

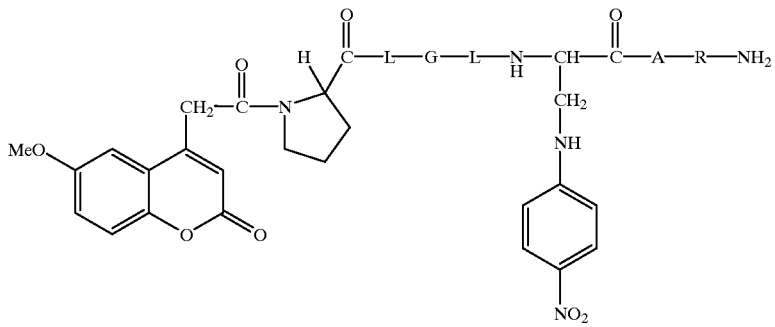

7-methoxycoumarin-4-yl-acetyl-pro-leu-gly-leu-3-(2,4-dinitrophenyl)-L-2-3-diaminoproprionyl-ala-arg-$NH_2$ The MCA assay was performed at 37° C. in buffer containing 50 mM Tricine (pH 7.5), 10 mM $CaCl_2$, 200 mM NaCl, and 1% DMSO with the following concentrations of matrix metalloproteinases: 1.4 nM stromelyin, 0.063 nM matrilysin, and 0.030 nM gelatinase A. The concentration of MCA substrate was 10 or 20 μM in a final volume of 1.6 mL. Fluorescence data was collected with Perkin-Elmer LS-5B and LS-5B spectrofluorimeters with $\lambda_{excitation}$=328 nm and $\lambda_{emission}$=393 nm. Spectrofluorimeters were interfaced with IBM-compatible microcomputer systems.

Competitive Inhibition Analyses

The $K_m$ for the MCA peptide substrate with the matrix metalloproteinases is quite high and exceeds its solubility under assay conditions. Consequently, the apparent $K_i$ ($K_{i,app}$) was determined to describe the strength of inhibition. However, in this case, $K_{i,app}$ would be essentially equal to $K_i$ since [S]<<$K_m$. For the determination of $K_{i,app}$, the concentration of the inhibitor was varied at a constant and low concentration of substrate and the steady-state rates of fluorescence change determined. In most cases absorptive quench due to the presence of ligand was not observed. For slow-binding inhibitors, onset of inhibition curves were collected for at least 45 minutes so that equilibrium was established. Steady-state rates of fluorescence change were obtained by fitting a curve to an equation for a single exponential decay containing a linear phase. The fitted value of the linear phase was taken as the steady-state rate. The steady-state rates were fitted to the Michaelis equation describing competitive inhibition by non-linear methods. Data resulting from tight-binding inhibition was analyzed, and $K_{i,app}$ determined by fitting the data to the tight-binding equation of Morrison See (Biochem. Biophys. Acta, vol. 185, pp. 269–286 (1969)) by non-linear methods.

The results of the above-described tests are presented below in Table 1.

TABLE 1

Enzyme Inhibition Constants ($K_i$) nM

I-a

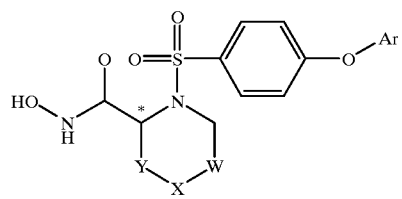

| | | Variable | | | | | | Enzyme | | |
|---|---|---|---|---|---|---|---|---|---|---|
| * | W | X | Y | Z | Ar | HSLN | Matr. | HFC | HG72kD | Coll3 |
| R/S | $CH_2$ | N—$CO_2C(CH_3)_3$ | $CH_2$ | O | 4-bromophenyl | 0.730 | 378.00 | 60.00 | 0.025 | 0.070 |
| R/S | $CH_2$ | N—H (HCl salt) | $CH_2$ | O | 4-bromophenyl | 1.800 | 263.00 | 68.00 | 0.770 | 1.100 |
| R/S | $CH_2$ | N—$COCH_3$ | $CH_2$ | O | phenyl | 0.640 | 113.00 | — | 0.110 | 0.050 |
| R/S | $CH_2$ | N—$CH_3$ | $CH_2$ | O | 4-bromophenyl | 1.400 | 1860.00 | 257.00 | 0.035 | 0.022 |
| R/S | $CH_2$ | N—$CONHCH_3$ | $CH_2$ | O | 4-chlorophenyl | 0.406 | 109.00 | — | 0.034 | 0.016 |
| R/S | $CH_2$ | S | $CH_2$ | O | 4-bromophenyl | 0.333 | 169.00 | — | 0.040 | — |
| R/S | $CH_2$ | N—H | $CH_2$ | O | phenyl | 6.200 | 560.00 | — | 0.864 | — |
| R/S | $CH_2$ | S | $CH_2$ | O | phenyl | 0.647 | 201.00 | — | 0.025 | 0.029 |
| R/S | $CH_2$ | N—$SO_2CH_3$ | $CH_2$ | O | 4-chlorophenyl | 0.150 | 44.00 | 5.50 | 0.022 | 0.015 |
| R | $CH_2$ | N—$CO_2C(CH_3)_3$ | $CH_2$ | O | 4-chlorophenyl | 0.310 | 142.00 | — | 0.007 | 0.006 |
| S | $CH_2$ | S | $CMe_2$ | O | 4-(furan-3-yl)phenyl | 0.06 | 0.7 | 1.4 | 0.0017 | 0.002 |
| S | $CH_2$ | S | $CMe_2$ | O | 4(imidaz-1-yl)phnyl | 0.25 | 5 | 15 | 0.011 | 0.017 |
| R | $CH_2$ | N—SO-(1-methyl-imidaz-1-yl) | $CH_2$ | O | 4-chlorophenyl | 0.09 | 40 | 7 | 0.004 | 0.006 |
| S | $CH_2$ | *S=O(*R) | $CH_2$ | O | pyrid-4-yl | 1.4 | | 32 | 0.094 | 0.13 |
| S | $CH_2$ | *S=O(*S) | $CMe_2$ | O | pyrid-4-yl | 2.3 | | 31 | 0.49 | 0.16 |
| R/S | C=O | NH | $CMe_2$ | O | 4-fluorophenyl | 0.84 | | 5.9 | 0.066 | 0.068 |
| R/S | $CH_2$ | $CH_2$ | N—$COCH_3$ | O | 4-fluorophenyl | 4.4 | | | 0.077 | 0.088 |

TABLE 1-continued

Enzyme Inhibition Constants ($K_i$) nM

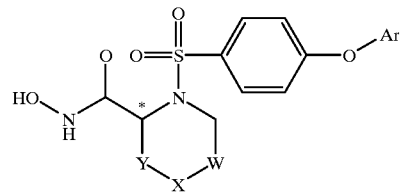

I-a

| * | W | X | Y | Z | Ar | HSLN | Matr. | HFC | HG72kD | Coll3 |
|---|---|---|---|---|---|---|---|---|---|---|
| S | $CH_2$ | S | $CMe_2$ | O | 4-chlorophenyl | 0.059 | | 1.3 | 0.017 | 0.001 |
| S | $CH_2$ | S=O | $CMe_2$ | O | 4-chlorophenyl | 2.5 | | | 0.018 | |
| S | $CH_2$ | S | $CMe_2$ | S | pyrid-4-yl | | | | | |
| R/S | $CH_2$ | N—$CH_3$ | $CH_2$ | O | phenyl | 6.300 | 2177.00 | — | 0.101 | 0.158 |
| R | $CH_2$ | O | $CH_2$ | O | 4-chlorophenyl | 0.093 | 77.00 | 8.90 | 0.031 | 0.021 |
| R | $CH_2$ | N—$CH_3$ (HCl salt) | $CH_2$ | O | 4-chlorophenyl | 0.670 | 993.00 | 130.00 | 0.025 | 0.020 |
| R | $CH_2$ | N—H (HCl salt) | $CH_2$ | O | 4-chlorophenyl | 1.000 | 171.00 | 34.00 | 0.413 | 0.363 |
| R | $CH_2$ | N—$SO_2CH_3$ | $CH_2$ | O | 4-chlorophenyl | 0.043 | 28.00 | 2.50 | 0.003 | 0.002 |
| R/S | $CH_2$ | S=O | $CH_2$ | O | 4-bromophenyl | 0.410 | 109.00 | 23.00 | 0.013 | 0.017 |
| R/S | $CH_2$ | N—$CO_2C(CH_3)_3$ | $CH_2$ | O | 4-cyanophenyl | 14.000 | 3570.00 | 580.00 | 0.696 | 1.97 |
| R/S | $CH_2$ | N—$CO_2C(CH_3)_3$ | $CH_2$ | O | 2-pyridyl | 17.000 | 2850.00 | 550.00 | 0.716 | 1.640 |
| R/S | $CH_2$ | S | $CH_2$ | O | 4-fluorophenyl | 0.530 | 313.00 | 40.00 | 0.028 | 0.035 |
| R/S | $CH_2$ | S=O | $CH_2$ | O | 4-fluorophenyl | 0.790 | 306.00 | 28.00 | 0.034 | 0.016 |
| R | $CH_2$ | N—$CO_2C(CH_3)_3$ | $CH_2$ | O | 4-fluorophenyl | 0.490 | 220.00 | 18.00 | 0.026 | — |
| R | $CH_2$ | N—H (HCl salt) | $CH_2$ | O | 4-fluorophenyl | 0.980 | 365.00 | 44.00 | 0.232 | 0.257 |
| R | $CH_2$ | N—$SO_2CH_3$ | $CH_2$ | O | 4-fluorophenyl | 0.130 | 52.00 | 4.70 | 0.007 | 0.005 |
| R | N—H | C=O | $CH_2$ | O | phenyl | 4.600 | 1300.00 | 210.00 | 0.057 | 0.124 |
| S | $CH_2$ | S | $CMe_2$ | O | 4-bromophenyl | 0.017 | 2.80 | 0.56 | 0.003 | 0.001 |
| S | $CH_2$ | S=O | $CMe_2$ | O | 4-bromophenyl | 0.056 | 11.0 | 3.6 | 0.009 | 0.010 |
| R | $CH_2$ | N—$CH_2CO_2CH_2CH_3$ (HCl salt) | $CH_2$ | O | 4-chlorophenyl | 0.250 | 240.00 | 48.00 | — | — |
| R | $CH_2$ | N—$SO_2CH_3$ | $CH_2$ | O | 4-methoxyphenyl | 0.190 | 74.00 | 16.00 | — | — |
| R | N—H | C=O | $CH_2$ | O | 4-fluorophenyl | 5.100 | 1840.00 | 187.00 | 0.152 | — |
| S | $CH_2$ | S | $CMe_2$ | O | 4-pyridyl | 0.170 | 54.00 | 8.20 | 0.083 | 0.038 |
| R | $CH_2$ | N—H | $CH_2$ | O | 4-fluorophenyl | 1.900 | 2060.00 | 176.00 | 0.410 | 0.013 |
| S | $CH_2$ | S | $CMe_2$ | O | 2-pyridyl | 0.510 | 70.00 | 12.00 | 0.202 | 0.074 |

Tumor Models

Primary subcutaneous tumors were established in female $BDF_1$ mice by trocar innoculation of the murine Lewis lung carcinoma (NIH) tumor line. This tumor line produces spontaneous lung metastases which arise from the primary tumor. Primary tumor growth was monitored by measuring the length and width of the subcutaneous tumor using calipers; lung metastases were counted at the end of the experiment (22 days after tumor implantation) by removing the lungs and counting the lesions using a dissecting microscope. The test compound was administered daily, i.p., beginning 24 hours after tumor implantation (day 1) and continuing through day 21. Primary tumor volumes and number of lung metastases were compared to control animals using an ANOVA followed by a comparison of means using the F statistic. For example, the compound of example 9(a), at a dosage of 50 mg/kg, produced a statistically significant (p<0.025) tumor growth delay, calculated as the delay in reaching 1000 $mm^3$ tumor volume between control and treated animals, and in the number of lung metastases (p<0.05) relative to the control. All drugs were administered at 50 mg/kg, i.p., daily, Day 1–Day 21. The results are presented in Table 2 below.

TABLE 2

| Example No. | Tumor Growth Delay | % Inhibition-Lung Metastases |
|---|---|---|
| 5(a) | 2.0 days | 13.6% |
| 8(a) | −0.1 days | 7.5% |
| 7(a) | 0.0 days | 16.1% |
| 9(a) | 7.2 days (p < 0.025) | 77.6% (p < 0.05) |

Arthritis Model

Previously frozen bovine nasal cartilage plugs weighing approximately 20 mg were embedded in polyvinyl sponges impregnated with Myobacterium tuberculosis and implanted subcutaneously in female Lewis rats. Dosing was begun 9 days after implantation and the plugs were harvested about one week later. The plugs were weighed and then hydrolyzed and the hydroxyproline content measured. Efficaciousness was determined by the comparison of the compound-treated groups with vehicle-treated controls. The results are presented in Table 3.

TABLE 3
| Example No. | dose p.o. (mg/kg/day) | weight loss % inhibition | hydroxyproline % protection |
|---|---|---|---|
| 3(a) | 25 | 97.5 | n.d. |
| 2(b) | 25 | 81.1 | n.d. |
| 5(a) | 10 | 59.6 | 72.5 |
| 7(a) | 10 | 77.4 | 86.7 |
p < 0.01 for all entries; n.d. = not determined
We claim:
1. A compound of formula 3a:
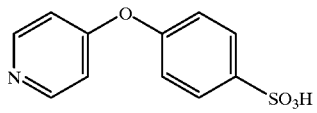
(3a)
or a salt thereof.
2. A compound of formula 3b:
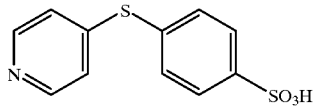
(3b)
or a salt thereof.
3. A salt of formula 4a:
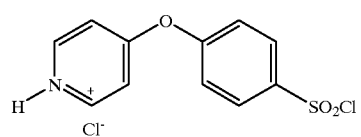
(4a)
or a salt thereof.
4. A salt of formula 4b:
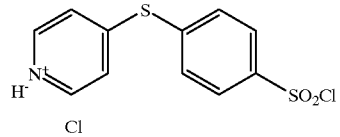
(4b)
or a salt thereof.
* * * * *